(12) United States Patent
Kaspar et al.

(10) Patent No.: US 7,723,314 B1
(45) Date of Patent: May 25, 2010

(54) METHODS AND COMPOSITIONS FOR TREATING PACHYONYCHIA CONGENITA

(75) Inventors: Roger L. Kaspar, Santa Cruz, CA (US); Robyn P. Hickerson, Santa Cruz, CA (US); Frances J. D. Smith, Dundee (GB); W. H. Irwin McLean, Perthshire (GB)

(73) Assignee: Transderm, Inc., Salt Lake City, UT (US)

( * ) Notice: Subject to any disclaimer, the term of this patent is extended or adjusted under 35 U.S.C. 154(b) by 76 days.

(21) Appl. No.: 11/510,503

(22) Filed: Aug. 24, 2006

Related U.S. Application Data

(60) Provisional application No. 60/731,566, filed on Oct. 28, 2005.

(51) Int. Cl.
*A01N 43/04* (2006.01)
*A61K 31/70* (2006.01)
(52) U.S. Cl. ........................................ 514/44
(58) Field of Classification Search .................... 514/44
See application file for complete search history.

(56) References Cited

U.S. PATENT DOCUMENTS

| 6,506,559 | B1 | 1/2003 | Fire et al. |
| 2002/0086356 | A1* | 7/2002 | Tuschl et al. ............... 435/69.1 |
| 2003/0139363 | A1 | 7/2003 | Kay et al. |
| 2003/0153519 | A1 | 8/2003 | Kay et al. |
| 2003/0170630 | A1* | 9/2003 | Alsobrook et al. ............. 435/6 |
| 2004/0087480 | A1 | 5/2004 | Rane et al. |
| 2005/0026286 | A1 | 2/2005 | Chi et al. |
| 2007/0031844 | A1* | 2/2007 | Khvorova et al. ............... 435/6 |

FOREIGN PATENT DOCUMENTS

| WO | WO 03/010180 | 2/2003 |
| WO | WO 2004078950 | 9/2004 |

OTHER PUBLICATIONS

Scherer et al. (Nat. Biotechnol., 2003, 21(12), pp. 1457-1465).*
Mahato et al. (Expert Opinion on Drug Delivery, Jan. 2005, vol. 2, No. 1, pp. 3-28).*
Macron (RNAi, startup believes siRNAs can treat extremely rare skin disorder [online], pp. 4-5, 2005, [retrieved on May 7, 2008], Retrieved from the Internet:< URL:http://www.mainews.com>.*
Tuschl et al. (Nature Biotech. 22: 326-330 2004).*
Terrinoni et al. (Invest. Dermatol. 117: 1391-1396, 2001).*
Smith et al. (Human Molecular Genetics 7:1143-1148, 1998).*

(Continued)

*Primary Examiner*—Brian Whiteman
(74) *Attorney, Agent, or Firm*—Thorpe North & Western LLP

(57) ABSTRACT

A method for treating pachyonychia congenita (PC) by identifying a genetic mutation contributing to PC, preparing a siRNA sequence that inhibits expression of the identified mutation, and administering the siRNA to a cell of a subject afflicted with PC. The siRNA treatment can include silencing of both the mutated and associated wildtype genes for a specific keratin. Specific mutations and inhibitory sequences are identified.

40 Claims, 11 Drawing Sheets

Left footpad, NSC4 siRNA
Right footpad, N171K.12 siRNA

OTHER PUBLICATIONS

Lin et al. (Exp. Dermatol 1998 8: 115-119).*

Mahajan et al. IJDVL [serial online] 2003 {retrieved on Jun. 11, 2008]; 69: 338-9. Available from: http://www.ijdvl.com/text.asp?2003/69/5/338/5748.*

Soutschek et al. (Nature 432: 173-178, 2004).*

IPPC 2004 meeting, Feb. 2004, [retrieved on May 8, 2008], Retrieved from the Internet< URL: http://www.pachyonychia1.org/IPCC/IPCC.program.AtaGlance-2004.pdf>.*

McLean et al., Insights into Genotype-Phenotype Correlation in Pachyonchia Congenita from the Human Intermediate Filament Mutation Database, J. Investig Dermatol Symp Proc 10, 2005, pp. 31-36, The Society for Investigative Dermatology, Inc.

Smith et al., The Genetic Basis of Pachyonchia Congenita, J. Investig Dermatol Symp Proc 10, 2005, pp. 21-30, The Society for Investigative Dermatology, Inc.

Leachman, et al, Clinical and Pathological Features of Pachyonychia Congenita, J. Investig Dermatol Symp Proc 10, 2005, pp. 3-17, The Society for Investigative Dermatology, Inc.

Milstone et al., Treatment of Pachyonchia Congenita, J. Investig Dermatol Symp Proc 10, 2005, pp. 18-20, The Society for Investigative Dermatology, Inc.

Jiang Chen and Dennis R. Roop, Mouse Models in Preclinical Studies for Pachyonychia Congenita, J. Investig Dermatol Symp Proc 10, 2005, pp. 37-46, The Society for Investigative Dermatology, Inc.

Lewin et al., Gene Therapy for Autosomal Dominant Disorders of Keratin, J. Investig Dermatol Symp Proc 10, 2005, pp. 47-61, The Society for Investigative Dermatology, Inc.

Leachman et al., Preface to Pachyonychia Congenita Symposium Proceedings, J. Investig Dermatol Symp Proc 10, 2005, pp. 1-2, The Society for Investigative Dermatology, Inc.

Kaspar, Roger L., Challenges in Developing Therapies for Rare Diseaes Including Pachyonychia Congenita, J. Investig Dermatol Symp Proc 10, pp. 62-66, 2005, The Society for Investigative Dermatology.

Wang et al., Small Hairpin RNAs Efficiently Inhibit Hepatitis C IRES—Mediated Gene Expression in Human Tissue Culture Cells and a Mouse Model, Sep. 2005, pp. 562-568, vol. 12, No. 3, Molecular Therapy.

* cited by examiner

Screening for effective K6a N171 siRNA inhibitors

| | | |
|---|---|---|
| K6A WT | AACAGATCAAGACCCTCAACAACAAGTTTGCCTCCTTC | SEQ ID NO: 627 |
| K6A N171K | AACAGATCAAGACCCTCAAaAACAAGTTTGCCTCCTTC | SEQ ID NO: 628 |

K6A N171K siRNA inhibitors

| | | | Activity Wt | Activity mut |
|---|---|---|---|---|
| N171K.1 | ACAGAUCAAGACCCUCAAaUU | SEQ ID NO: 629 | - | + |
| N171K.2 | CAGAUCAAGACCCUCAAaAUU | SEQ ID NO: 630 | + | ++ |
| N171K.3 | AGAUCAAGACCCUCAAaAAUU | SEQ ID NO: 631 | + | +++ |
| N171K.4 | GAUCAAGACCCUCAAaAACUU | SEQ ID NO: 632 | - | +++ |
| N171K.5 | AUCAAGACCCUCAAaAACAUU | SEQ ID NO: 633 | + | +++ |
| N171K.6 | UCAAGACCCUCAAaAACAAUU | SEQ ID NO: 634 | + | +++ |
| N171K.7 | CAAGACCCUCAAaAACAAGUU | SEQ ID NO: 635 | - | + |
| N171K.8 | AAGACCCUCAAaAACAAGUUU | SEQ ID NO: 636 | - | - |
| N171K.9 | AGACCCUCAAaAACAAGUUUU | SEQ ID NO: 637 | - | + |
| N171K.10 | GACCCUCAAaAACAAGUUUUU | SEQ ID NO: 638 | - | ++ |
| N171K.11 | ACCCUCAAaAACAAGUUUGUU | SEQ ID NO: 639 | - | + |
| N171K.12 | CCCUCAAaAACAAGUUUGCUU | SEQ ID NO: 640 | - | +++ |
| N171K.13 | CCUCAAaAACAAGUUUGCCUU | SEQ ID NO: 641 | - | - |
| N171K.14 | CUCAAaAACAAGUUUGCCUUU | SEQ ID NO: 642 | - | - |
| N171K.15 | UCAAaAACAAGUUUGCCUCUU | SEQ ID NO: 643 | - | - |
| N171K.16 | CAAaAACAAGUUUGCCUCCUU | SEQ ID NO: 644 | - | - |
| N171K.17 | AAaAACAAGUUUGCCUCCUUU | SEQ ID NO: 645 | - | - |
| N171K.18 | AaAACAAGUUUGCCUCCUUUU | SEQ ID NO: 646 | - | - |
| N171K.19 | aAACAAGUUUGCCUCCUUCUU | SEQ ID NO: 647 | + | ++ |

K6A WT siRNA inhibitors

| | | | Activity Wt | Activity mut |
|---|---|---|---|---|
| WT.1 | ACAGAUCAAGACCCUCAAcUU | SEQ ID NO: 664 | - | - |
| WT.2 | CAGAUCAAGACCCUCAAcAUU | SEQ ID NO: 665 | +++ | + |
| WT.3 | AGAUCAAGACCCUCAAcAAUU | SEQ ID NO: 666 | +++ | ++ |
| WT.4 | GAUCAAGACCCUCAAcAACUU | SEQ ID NO: 656 | ++ | - |
| WT.5 | AUCAAGACCCUCAAcAACAUU | SEQ ID NO: 667 | +++ | + |
| WT.6 | UCAAGACCCUCAAcAACAAUU | SEQ ID NO: 654 | +++ | +++ |
| WT.7 | CAAGACCCUCAAcAACAAGUU | SEQ ID NO: 668 | - | - |
| WT.8 | AAGACCCUCAAcAACAAGUUU | SEQ ID NO: 669 | + | - |
| WT.9 | AGACCCUCAAcAACAAGUUUU | SEQ ID NO: 670 | +++ | - |
| WT.10 | GACCCUCAAcAACAAGUUUUU | SEQ ID NO: 658 | ++ | - |
| WT.11 | ACCCUCAAcAACAAGUUUGUU | SEQ ID NO: 671 | ++ | - |
| WT.12 | CCCUCAAcAACAAGUUUGCUU | SEQ ID NO: 672 | +++ | - |
| WT.13 | CCUCAAcAACAAGUUUGCCUU | SEQ ID NO: 673 | - | - |
| WT.14 | CUCAAcAACAAGUUUGCCUUU | SEQ ID NO: 674 | - | - |
| WT.15 | UCAAcAACAAGUUUGCCUCUU | SEQ ID NO: 675 | - | - |
| WT.16 | CAAcAACAAGUUUGCCUCCUU | SEQ ID NO: 676 | + | + |
| WT.17 | AAcAACAAGUUUGCCUCCUUU | SEQ ID NO: 677 | - | - |
| WT.18 | AcAACAAGUUUGCCUCCUUUU | SEQ ID NO: 657 | +++ | ++ |
| WT.19 | cAACAAGUUUGCCUCCUUCUU | SEQ ID NO: 655 | +++ | +++ |

METHODS AND COMPOSITIONS FOR TREATING PACHYONYCHIA CONGENITA

This patent application claims the benefit of U.S. Provisional Patent Application Ser. No. 60/731,566 filed on Oct. 28, 2005 which is incorporated herein by reference.

This patent application hereby incorporates by reference in its entirety the material contained on the compact disc submitted to the USPTO in accordance with 37 C.F.R. §1.77(b)(4). The CD containing said material was created on Aug. 24, 2006, has a file size of 122 KB, and a file name of "Sequence Listing.ST25.txt".

FIELD OF THE INVENTION

The present invention is related generally to methods and compositions for treating pachyonychia congenita. More particularly, the present invention is related to the use of RNAi and in particular transdermally administered siRNA or shRNA to treat pachyonychia congenita.

BACKGROUND OF THE INVENTION

Pachyonychia congenita (PC) is a rare, autosomal dominant keratin disorder that typically affects the nails, skin, oral mucosa, larynx, hair, and teeth. Currently there are two distinct syndromes of PC that are recognized: PC-1 or Jadassohn-Lewandowsky type, and PC-2, or Jackson-Lawler type. The PC-1 clinical phenotype is associated with mutations in the genes encoding the K6a or K16 keratins whereas the PC-2 phenotype is associated with mutations in the genes encoding the K6b or K17 keratins. There are at least 20 known genetic mutations that cause PC and a high percentage of these are mononucleotide mutations, although other mutations can also cause the disorder. The most common symptoms associated with PC include thickened fingernails and toenails, plantar keratoderma (blisters and thick calluses on the soles of the feet), palmar keratoderma (blisters and thick calluses on the palms of the hands), oral leukokeratosis (thick white growth on tongue or cheeks), follicular keratosis (bumps formed around hair follicles), pilosebaceous cyst formation (including steatocystoma type), laryngeal involvement (hoarseness), hyperhidrosis (excessive sweating on feet or hands), and natal or prenatal teeth.

There are currently no known specific treatments for PC. Available treatments generally are directed at specific manifestations of the disorder but generally do not affect the underlying cause. As individual patients are generally troubled by different manifestations of the disease, no single treatment plan is effective for treating the disorder as a whole. Treatment options for PC fall into four broad categories, non-invasive (mechanical), invasive (surgical), chemical, and pharmacological. Currently no treatment options are available for PC which address the underlying cause of the disorder and therefore prevent the occurrence of symptoms.

SUMMARY OF THE INVENTION

The present invention provides methods and compositions for treating pachyonychia congenita (PC). In one embodiment a method of treating PC in a subject may include: 1) identifying a genetic mutation which contributes to PC, and; 2) administering an RNA sequence that inhibits expression of such genetic mutation to target cells in the subject.

In another embodiment, a method of treating PC in a subject may include administering to the subject, an RNA sequence which inhibits expression of the gene encoding for a keratin selected from the group consisting of K6a, K6b, K16, K17, and combinations thereof. Such inhibition can be either of the wildtype form of the target gene, the mutant form of the target gene, or of both the mutant and the wildtype form of the target gene.

In another embodiment, an RNA sequence which inhibits the expression of the gene encoding for K6a keratin can be selected from the group of: SEQ ID NOS:3-31, SEQ ID NOS:34-69, SEQ ID NOS:72-100, SEQ ID NOS:103-131, SEQ ID NOS:134-162, SEQ ID NOS:165-193, SEQ ID NOS:196-233, SEQ ID NOS:234-254, SEQ ID NOS:257-285, SEQ ID NOS:288-316, SEQ ID NOS:319-347, SEQ ID NOS:629-658, and SEQ ID NOS:661-663.

In yet another embodiment, an RNA sequence which inhibits the expression of the gene encoding for K6b keratin can be selected from the group of: SEQ ID NOS:350-378.

In still another embodiment, an RNA sequence which inhibits the expression of the gene encoding for K16 keratin can be selected from the group of SEQ ID NOS: 381-409, SEQ ID NOS:412-440, SEQ ID NOS:443-471, SEQ ID NOS:474-502, SEQ ID NOS:505-533, SEQ ID NOS:536-564.

In yet another embodiment an RNA sequence which inhibits the expression of the gene encoding for K17 keratin can be selected from the group SEQ ID NOS:567-595, and SEQ ID NOS:598-626.

In addition to the foregoing, the present invention encompasses formulations for administering the RNA sequences recited herein to target cells of a subject. Examples of such formulations include without limitation, topical formulations, including gels, lotions, crèmes, ointments, adhesives, and pastes, as well as transdermal patches, intradermal injections, iontophoretic mechanisms, etc.

Reference will now be made to the exemplary embodiments of the present invention, and specific language will be used herein to describe the same. It will nevertheless be understood that no limitation of the scope of the invention is thereby intended.

BRIEF DESCRIPTION OF THE DRAWINGS

FIG. 3 shows a sequence walk of siRNA inhibitors targeting the N171 site of K6a. A complete sequence walk was done for the N171K single nucleotide mutation (top half of FIG. 3) as well as the wildtype counterpart (bottom half). The amount of inhibition against the mutant target (perfect match) or wildtype control target (imperfect match) is shown for the N171K target on FIG. 3 top: (−) less than 25% inhibition; (+) 25-50% inhibition; (++) 50-75% inhibition; (+++) greater than 75% inhibition. A similar analysis was done for siRNAs targeting the wildtype K6a (FIG. 3, bottom half).

DETAILED DESCRIPTION OF THE INVENTION

Figure 1:
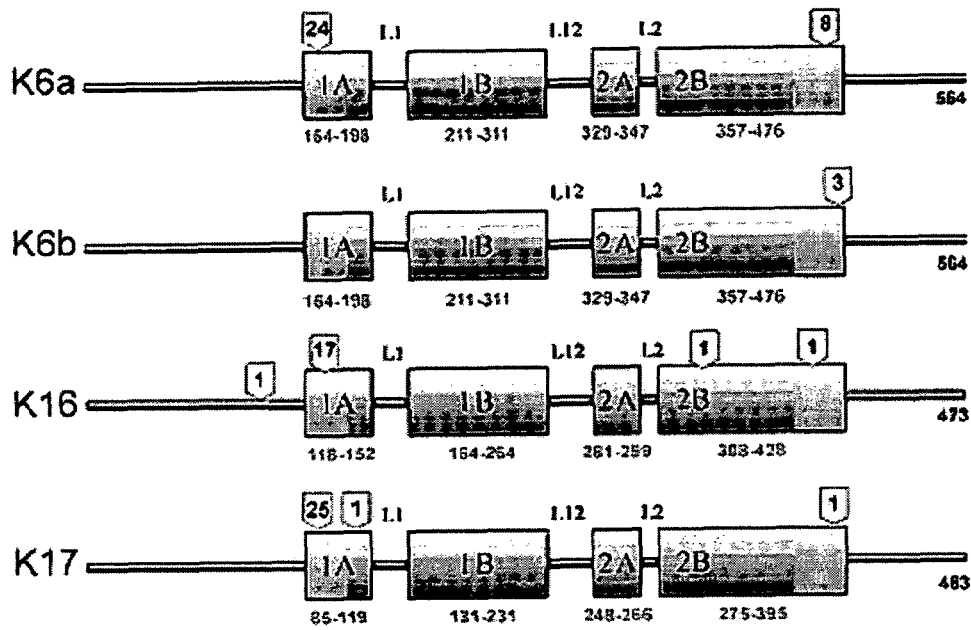
FIG. 1 shows a schematic diagram of protein structures of keratins K6a, K6b, K16, and K17, oriented from N-terminus (left) to C-terminus (right). Helical (1A, 1B, 2A, 2B) and non-helical domains are indicated. Locations of mutations and the number of families with those mutations are indicated by arrows. Helix boundary motifs are shown in gray at the N-terminal end of helical domain 1A (Helix Initiation Motif, 22 amino acids) and the C-terminal end of helical domain 2B (Helix Termination Motif, 30 amino acids). Amino acid position is numbered.

A new genetic disorder therapy which is being heavily researched is RNA interference (RNAi). RNAi is an evolutionarily conserved mechanism that results in specific gene inhibition. In the RNAi pathway, double stranded RNA can effectively induce potent gene silencing without inducing an immune response. RNAi is mediated by RNA-induced silencing complex (RISC), a sequence specific, multi-component nuclease that destroys messenger RNAs homologous to the silencing trigger. RISC is known to contain short RNAs (from 15-31 nucleotides in length) which are derived from double stranded RNA triggers. A more detailed discussion of the RNAi process in general may be found in *Gene Silencing by RNA Interference: Technology and Application* (Muhammad Sohail ed., 2005), which is incorporated herein by reference.

The present invention illustrates that diseases of the skin with well-described mechanisms are amenable to nucleic acid-based therapies. Although normal skin (and especially the stratum corneum) represents a formidable barrier to topical nucleic acid delivery, a number of methods have been used to successfully deliver nucleic acids to skin. The present invention uses a variety of delivery mechanisms to deliver key RNA inhibitors including intradermal injection and cream formulations.

Although the present invention illustrates the use of RNAi to treat PC, the ability to locally deliver specific robust siRNA-based gene inhibitors would be a boon to patients suffering from a number of monogenic skin disorders in addition to pachyonychia congenita such as epidermolysis bullosa, Hailey-Hailey, Darier's disease, loricrin keratoderma and epidermolytic hyperkeratosis, and as such, the general principles embodied herein may be applied for treatment of such conditions.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

DEFINITIONS

In describing and claiming the present invention, the following terminology will be used.

The singular forms "a," "an," and "the" include plural referents unless the context clearly dictates otherwise. Thus, for example, reference to "an RNA sequence" includes reference to one or more of such RNA sequences, and reference to "the genetic mutation" includes reference to one or more of such genetic mutation.

As used herein, "subject" refers to a mammal having pachyonychia congenita. In some aspects, such subject may be a human.

The term "gene" refers to a nucleic acid comprising an open reading frame encoding a polypeptide.

The term "sequence" when used with respect to RNA inhibitors refers to at a minimum, a single strand oligonucleotide of between about 15 and 31 base pairs (siRNA), which may hybridize with target mRNA and thereby inhibits the expression of the targeted gene. The sequence may be formed and delivered to a subject as double stranded RNA, the second strand being complimentary to the inhibitory sequence, or as small hairpin RNA (shRNA), the inhibitory sequence being attached through a loop sequence to a sequence complimentary to the inhibitory sequence. The sequence may also include 2 nucleotide overhangs.

As used herein, the terms "target cell" or "target cells", refer to cells that produce keratin proteins, the improper production of which contribute to PC. Such keratins include without limitation, those recited herein.

As used herein, the term "inhibition of" or "silencing of" with respect to genetic expression refers to the absence of, or at least an observable decrease in, the level of protein from a target gene.

The term "expression" with respect to a gene sequence refers to transcription of the gene and, as appropriate, translation of the resulting mRNA transcript to a protein.

"Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated analysis (FACS). For RNA-mediated inhibition in a whole organism or cell line, gene expression is conveniently assayed by use of a reporter or drug resistance gene whose protein product is easily assayed. Such reporter genes can include but are not limited to beta galactosidase (LACZ), beta glucoronidase (GUS), chloramphenicol acetyltransferase (CAT), green fluorescent protein (GFP), horseradish peroxidase (HRP), luciferase (LUC), etc.

As used herein, "effective amount" or "therapeutically effective amount" of an RNA refers to a sufficient amount of RNA to perform an intended task and achieve an intended result. For example, an effective amount of siRNA may be an amount which is sufficient to silence expression a mutated keratin gene. It is understood that various biological factors may affect the ability of a particular RNA sequence to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

As used herein, sequences, compounds, formulations, delivery mechanisms, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

INVENTION

As mentioned above, pachyonychia congenita is generally divided into two main subtypes, PC-1 and PC-2. Although some of the manifestations of the disease differ in the two forms of the disease, the general underlying cause in the disorder is the same, mutation of keratin encoding genes. Keratins are the type I and type II intermediate filament proteins, which form a cytoskeletal network within all epithelial cells. Mutations in these genes result in aberrant cytoskeletal networks, which present clinically as a variety of epithelial fragility phenotypes such as PC. Four keratin genes are presently known to be associated with PC, namely K6a, K6b, K16, and K17. FIG. 1 shows a schematic diagram of the protein structures of each of these four keratins oriented from N-terminus (left) to C-terminus (right). The locations of the mutations and the number of families with those mutations are shown indicated by arrows. There are several recurrent mutations, the predominant one for PC-1 being at the K6a N 171 site, which is either a 3 nucleotide deletion (171 del) or a single base mutation resulting in an amino acid change (e.g. N171K).

The present invention provides methods for treating PC by identifying a genetic mutation contributing to PC, preparing an RNA sequence that inhibits expression of the identified genetic mutation, and then administering the RNA sequence to a target cell in the subject having PC. As mentioned above, there are currently more than 20 known genetic mutations which cause PC, many of which have been identified previously in Smith et al, J. Investig. Dermatol Symp. Proc. 10:21-30, 2005, which is herein incorporated by reference in its entirety. Once the desired genetic mutation is identified, an inhibitory RNA sequence for that mutation is prepared. The prepared inhibitory sequences can vary in length but generally are from about 15 to 31 bases in length depending on the nature of the mutation being silenced (single nucleotide vs. 3 nucleotide deletion) and the particular sequence surrounding the mutation. These prepared sequences are generally considered to be small interfering siRNA. The RNA sequences of the present invention can include modifications to either the phosphate-sugar backbone or the base. For example, the phosphodiester linkages of the RNA may be modified to include at least one of a nitrogen or sulfur or heteroatom. Likewise, bases may be modified to block the activity of adenosine deaminase. The RNA sequence may be produced enzymatically or by partial/total organic synthesis; any modified ribonucleotide can be introduced by in vitro enzymatic or organic synthesis.

Once the inhibitory sequences are determined they can be administered to a subject suffering from PC. The RNA sequences of the present invention can be administered as hybridized double stranded complementary RNA (dsRNA), as single stranded RNA (typically siRNA), or alternatively as a single hairpin molecule of RNA (shRNA) that contains a 15 to 31 basepair stem. The desirability of using dsRNA vs. shRNA can vary depending on the particular sequence and the mutation for which inhibition is sought; however, both forms have been shown to be capable and effective for use in gene silencing. For more information on small hairpin RNA see Wang et al., *Molecular Therapy*, Vol. 12, No. 3, September 2005, which is hereby incorporated by reference in its entirety. Whether administered as dsRNA or shRNA, there are a variety of means by which the RNA sequences of the present invention can be delivered to a subject. Suitable delivery means include but are not limited to injection, including intradermal injection using single needles and needle arrays, topical formulations, such as lotions, creams, gels, ointments, jellies (such as petroleum jelly), adhesives, pastes, liquids, soaps, shampoos, transdermal patches, films, electrophoresis, or combinations thereof. In one aspect, the specific carrier utilized in the production of a formulation may be selected because of its positive impact on skin. For example, carriers that moisturize, hydrate, or otherwise benefit the skin can be used.

In some aspects, the RNA sequences of the present invention can be administered in combination with other therapeutically effective compounds. Ideally, such compounds would be those agents having a therapeutic skin effect. Examples of such compounds include but are not limited to corticosteroids such as hydrocortisone, a lanolin-containing product, aloe vera, urea, propylene glycol, a-hydroxy acids, lactic acid, salicylic acid, vitamin $D_3$ and its derivatives, vitamin A and retinoids, levothyroxin, NSAIDS, cyclosporine, methotrexate sodium, anthralin, acitretin, tazarotene, coal tar, clobetasol propionate, botulinum toxin, topical anesthetics, antihistamine, and combinations thereof.

Effectiveness of the PC inhibition can depend on the particular RNA inhibitor as well as the amount of inhibiting RNA administered to the subject. Other biologically related factors may also be variables in determining the effectiveness of the inhibitors. Therapeutically effective amounts of RNA sequences can be from about 0.1 mg to about 10 mg.

In one embodiment, the present invention provides a method of treating a subject with PC by administering to the subject an RNA sequence which inhibits the expression of the gene encoding for a keratin selected from the group of K6a, K6b, K16, K17, and combinations thereof. It has been discovered that there is redundancy of keratin expression in keratinocytes, and as such it is possible to suppress expression of wildtype, mutated, or both the wildtype and mutated keratins without causing unwanted side-effects. In other words, by simply eliminating production of any one or more of the above-recited keratins it may be possible to reduce or eliminate the effects of PC without any unwanted side effects because other keratins overlap the functions performed by the above-recited keratins. By simultaneously silencing the expression of both wildtype and mutated keratin, a single siRNA inhibitory sequence can be used to effectively treat all subjects with mutations in a particular gene. Aside from their specificity for both wildtype and mutated genes, these siRNA sequences share similar characteristics with the other RNA sequences of the present invention, namely that they can be administered as both dsRNA or shRNA and can have effective stem lengths of between about 15 to about 31 nucleotides.

Examples of sequences which can be used to inhibit the expression of the K6a keratin include but are not limited to SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12 SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:11, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129. SEQ ID NO:130, SEQ ID NO:131, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:146, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268, SEQ ID NO:269, SEQ ID NO:270, SEQ ID NO:271, SEQ ID NO:272, SEQ ID NO:273, SEQ ID NO:274, SEQ ID NO:275, SEQ ID NO:276, SEQ ID NO:277, SEQ ID NO:278, SEQ ID NO:279, SEQ ID NO:280, SEQ ID NO:281, SEQ ID NO:282, SEQ ID NO:283, SEQ ID NO:284, SEQ ID NO:285, SEQ ID NO:288, SEQ ID NO:289. SEQ ID NO:290, SEQ ID NO:291, SEQ ID NO:292, SEQ ID NO:293, SEQ ID NO:294, SEQ ID NO:295, SEQ ID NO:296, SEQ ID NO:297, SEQ ID NO:298, SEQ ID NO:299, SEQ ID NO:300, SEQ ID NO:301, SEQ ID NO:302, SEQ ID NO:303, SEQ ID NO:304, SEQ ID NO:305, SEQ ID NO:306, SEQ ID NO:307, SEQ ID NO:308, SEQ ID NO:309, SEQ ID NO:310, SEQ ID NO:311, SEQ ID NO:312, SEQ ID NO:313, SEQ ID NO:314, SEQ ID NO:315, SEQ ID NO:316, SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:330, SEQ ID NO:331, SEQ ID NO:332, SEQ ID NO:333, SEQ ID NO:334, SEQ ID NO:335, SEQ ID NO:336, SEQ ID NO:337, SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:629, SEQ ID NO:630, SEQ ID NO:631, SEQ ID NO:632, SEQ ID NO:633, SEQ ID NO:634, SEQ ID NO:635, SEQ ID NO:636, SEQ ID NO:637, SEQ ID NO:638, SEQ ID NO:639, SEQ ID NO:640, SEQ ID NO:641, SEQ ID NO:642, SEQ ID NO:643, SEQ ID NO:644, SEQ ID NO:645, SEQ ID NO:646, SEQ ID NO:647, SEQ ID NO:648, SEQ ID NO:649, SEQ ID NO:650, SEQ ID NO:651, SEQ ID NO:652, SEQ ID NO:653, SEQ ID NO:654, SEQ ID NO:655, SEQ ID NO:656, SEQ ID NO:657, SEQ ID NO:658, SEQ ID NO:661, SEQ ID NO:662, SEQ ID NO:663, and mixtures thereof.

Examples of sequences which are effective against the K6b keratin include but are not limited to SEQ ID NO:350, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, SEQ ID NO:363, SEQ ID NO:364, SEQ ID NO:365, SEQ ID NO:366, SEQ ID NO:367, SEQ ID NO:368, SEQ ID NO:369, SEQ ID NO:370, SEQ ID NO:371, SEQ ID NO:372, SEQ ID NO:373, SEQ ID NO:374, SEQ ID NO:375, SEQ ID NO:376, SEQ ID NO:377, SEQ ID NO:378, and mixtures thereof.

Similarly, Examples of sequences which are effective against the K16 keratin include but are not limited to SEQ ID NO: 381, SEQ ID NO:382, SEQ ID NO:383, SEQ ID NO:384, SEQ ID NO:385, SEQ ID NO:386, SEQ ID NO:387, SEQ ID NO:388, SEQ ID NO:389, SEQ ID NO:390, SEQ ID NO:391, SEQ ID NO:392, SEQ ID NO:393, SEQ ID NO:394, SEQ ID NO:395, SEQ ID NO:396, SEQ ID NO:397, SEQ ID NO:398, SEQ ID NO:399, SEQ ID NO:400, SEQ ID NO:401, SEQ ID NO:402, SEQ ID NO:403, SEQ ID NO:404, SEQ ID NO:405, SEQ ID NO:406, SEQ ID NO:407, SEQ ID NO:408, SEQ ID NO:409, SEQ ID NO:412, SEQ ID NO:413, SEQ ID NO:414, SEQ ID NO:415, SEQ ID NO:416, SEQ ID NO:417, SEQ ID NO:418, SEQ ID NO:419, SEQ ID NO:420, SEQ ID NO:421, SEQ ID NO:422, SEQ ID NO:423, SEQ ID NO:424, SEQ ID NO:425, SEQ ID NO:426, SEQ ID NO:427, SEQ ID NO:428, SEQ ID NO:429, SEQ ID NO:430, SEQ ID NO:431, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:443, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, SEQ ID NO:484, SEQ ID NO:485, SEQ ID NO:486, SEQ ID NO:487, SEQ ID NO:488, SEQ ID NO:489, SEQ ID NO:490, SEQ ID NO:491, SEQ ID NO:492, SEQ ID NO:493, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:505, SEQ ID NO:506, SEQ ID NO:507, SEQ ID NO:508, SEQ ID NO:509, SEQ ID NO:510, SEQ ID NO:511, SEQ ID NO:512, SEQ ID NO:513, SEQ ID NO:514, SEQ ID NO:515, SEQ ID NO:516, SEQ ID NO:517, SEQ ID NO:518, SEQ ID NO:519, SEQ ID NO:520, SEQ ID NO:521, SEQ ID NO:522, SEQ ID NO:523, SEQ ID NO:524, SEQ ID NO:525, SEQ ID NO:526, SEQ ID NO:527, SEQ ID NO:528, SEQ ID NO:529, SEQ ID NO:530, SEQ ID NO:531, SEQ ID NO:532, SEQ ID NO:533, SEQ ID NO:536, SEQ ID NO:537, SEQ ID NO:538, SEQ ID NO:539, SEQ ID NO:540, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:549, SEQ ID NO:550, SEQ ID NO:551, SEQ ID NO:552, SEQ ID NO:553, SEQ ID NO:554, SEQ ID NO:555, SEQ ID NO:556, SEQ ID NO:557, SEQ ID NO:558, SEQ ID NO:559, SEQ ID NO:560, SEQ ID NO:561, SEQ ID NO:562, SEQ ID NO:563, SEQ ID NO:564, and mixtures thereof.

Examples of sequences which can be effective in inhibiting K17 keratin include but are not limited to SEQ ID NO:567, SEQ ID NO:568, SEQ ID NO:569, SEQ ID NO:570, SEQ ID NO:571, SEQ ID NO:572, SEQ ID NO:573, SEQ ID NO:574, SEQ ID NO:575, SEQ ID NO:576, SEQ ID NO:577, SEQ ID NO:578, SEQ ID NO:579, SEQ ID NO:580, SEQ ID NO:581, SEQ ID NO:582, SEQ ID NO:583, SEQ ID NO:584, SEQ ID NO:585, SEQ ID NO:586, SEQ ID NO:587, SEQ ID NO:588, SEQ ID NO:589, SEQ ID NO:590, SEQ ID NO:591, SEQ ID NO:592, SEQ ID NO:593, SEQ ID NO:594, SEQ ID NO:595, SEQ ID NO:598, SEQ ID NO:599, SEQ ID NO:600, SEQ ID NO:601, SEQ ID NO:602, SEQ ID NO:603, SEQ ID NO:604, SEQ ID NO:605, SEQ ID NO:606, SEQ ID NO:607, SEQ ID NO:608, SEQ ID NO:609, SEQ ID NO:610, SEQ ID NO:611, SEQ ID NO:612, SEQ ID NO:613, SEQ ID NO:614, SEQ ID NO:615, SEQ ID NO:616, SEQ ID NO:617, SEQ ID NO:618, SEQ ID NO:619. SEQ ID NO:620, SEQ ID NO:621, SEQ ID NO:622, SEQ ID NO:623, SEQ ID NO:624, SEQ ID NO:625, SEQ ID NO:626, and mixtures thereof.

In each of the above listed sequence groupings, each sequence can be effective as an inhibitor with specificity towards a mutated gene, a wildtype gene, or both the mutated and the wildtype gene.

Methodolgy

Figure 2:
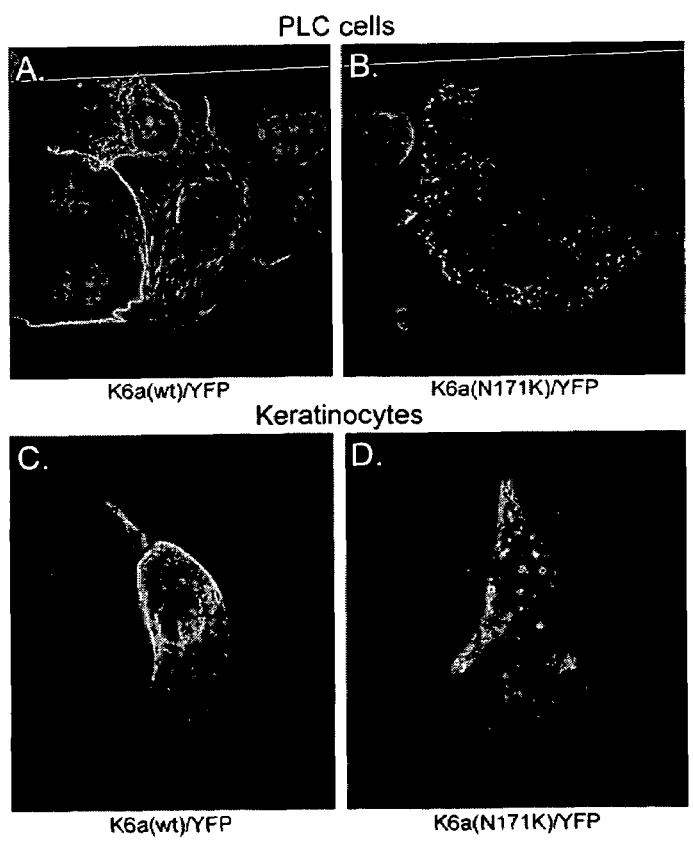
FIG. 2 shows the transfection of cells with mutant K6a results in faulty keratin filament formation. Panels A and B show PLC cells which were transfected (Lipofectamine 2000, Invitrogen) with K6a(WT)/YFP (A) or K6a(N171K)/YFP (B, K6a(N171K)/YFP contains a single nucleotide mutation). Panels C and D show keratinocytes which were transfected with these same plasmids as indicated. 48 hours following transfection, the cells were fixed and stained with DAPI (stains nuclei blue; PLC cells only) and analyzed by confocal microscopy.

In order to show that PC-specific mutations result in disruption of keratin filament formation, human PLC hepatoma cells and HPV E6/E7 immortalized keratinocytes were transfected with wildtype and mutant forms of K6a fused to a reporter protein (YFP). 48 hours following transfection the cells were fixed, stained with DAPI and visualized by fluorescence microscopy. Introduction of wildtype K6a (WT)/YFP resulted in normal keratin filaments in transfected PLC cells and keratinocytes as assayed by fluorescence microscopy. FIG. 2 shows images of the transfected and stained cells. In contrast, a similar construct containing a specific mutation in K6a derived from PC patients (N171K, a single nucleotide C to A mutation resulting in an asparagine to lysine amino acid change) resulted in aggregate formation and few if any normal keratin filaments were observed.

In order to differentiate inhibition of mutant genes versus wildtype, a fluorescence-based tissue culture assay was used. The assay tests siRNA inhibitors against wildtype and mutant gene mRNA in which the target gene is fused to a reporter gene, in this case yellow fluorescent protein (YFP). Once the target gene is identified, siRNA inhibitors can be made that target every possible sequence containing the single nucleotide mutation or the three nucleotide deletion. Co-transfection experiments of wildtype and target mutation expression constructs reveal which inhibitors are potent inhibitors for either the wildtype alone, the mutant alone, or both in combination. As a positive control, an eGFP-specific siRNA inhibitor can be co-transfected with the wildtype and mutant constructs. YFP and eGFP are nearly identical in sequence and there are no nucleotide differences in the target site for the eGFP siRNA inhibitor used.

EXPERIMENTAL

Figure 4:
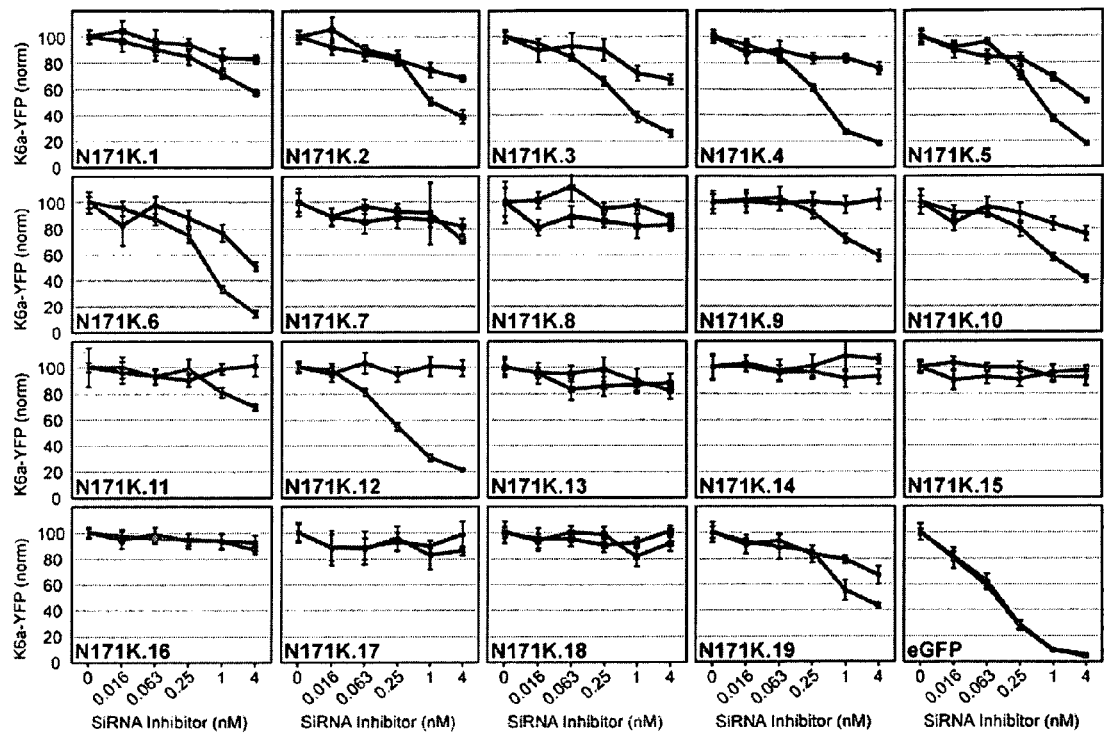
FIG. 4 shows the quantitative FACS results of a complete siRNA sequence walk of the K6a N171K single nucleotide mutation. SiRNAs (19+2 format) were designed and synthesized to screen all possible target sequences containing the N171K mutation. Each siRNA was co-transfected into 293FT tissue culture cells with either an expression vector containing the K6a(N171K)/YFP fusion (red) or K6a(WT)/YFP mRNA. 48 hours following transfection, the cells were trypsinized and analyzed for YFP expression using a Becton Dickinson FACScan using channel FL1 (530 nm emission filter). 5,000 cells per transfection were analyzed. The data were generated by gating the cells and determining the percentage of cells that dropped below the gate with and without siRNA treatment. The data were normalized (to 100) and then corrected against cells transfected with NSC4 siRNA (non-specific control). These results indicate that some siRNAs such as N171K.4 and N171K.12 can strongly discriminate between wildtype K6a and a mutant K6a that contains a single nucleotide mutation whereas other siRNAs such as N171K.13-N171K.18 have no effect on either.

Differential Inhibition of Mutant K6a/YFP Vs. Wildtype by Mutant-Specific K6a siRNAs in Tissue Culture Cells A fluorescence-based tissue culture assay was developed and used to test siRNA inhibitors against wildtype and mutant K6a mRNA in which the target gene is fused to a reporter gene (YFP). siRNAs designed to target PC-1 mutations consisting of a single nucleotide change (N171K) in the K6a gene were tested. A series of siRNA inhibitors (19+2 format) that target every possible sequence containing the single nucleotide mutation in K6a (N171K) were designed and synthesized (supplied by Dharmacon RNA Technologies). FIG. 3 shows the sequence walk of the siRNA inhibitors for the N171 site of K6a, as well as the amount of inhibition against the mutant and wildtype expression plasmids. Co-transfection experiments with K6a(WT)/YFP and K6a(N171K)/YFP expression constructs were performed. Each siRNA was co-transfected into 293FT tissue culture cells with either a plasmid vector expressing the K6a(N171K)/YFP fusion RNA or a similar construct containing wildtype K6a/YFP. 48 hours following transfection, the cells were trypsinized and analyzed for YFP expression using a Becton Dickson FACScan using channel FL1 (530 nm emission filter). Five thousand cells per transfection were analyzed. The data were generated by gating the cells and determining the percentage of cells that dropped below the gate and without siRNA treatment. As a positive control, eGFP-specific siRNA inhibitors were co-transfected with the wildtype and mutant K6a/YFP constructs (IC50 values were ~0.1 nM against both constructs). No effect was observed with the irrelevant non-specific control (NSC4) siRNA inhibitor. The data were normalized and then corrected against cells transfected with the non-specific control. The results of the experiment are shown in FIG. 4. Specifically, the co-transfection experiments revealed six inhibitors (N171K.2-5, N171K.10 and N171K.12 (SEQ ID NOS: 630, 631, 632, 633, 638, and 640) that exhibit strong discrimination between mutant K6a and wildtype K6a targets (e.g. IC50 values for N171K.12 were >4 nM and ~0.3 nM against the wildtype and mutant constructs, respectively as determined by FACS analysis).

These results show that siRNA inhibitors can have robust, specific and high inhibitory activity against single nucleotide mutations, in this example a K6a (N171K) mutation, with little or no effect on the wildtype activity. As was expected, some of the designed inhibitors exhibited little or no inhibition against either wildtype or mutant expression. The observation that some inhibition was observed on wildtype K6a expression with some siRNA targeting mutant forms is not necessarily problematic, as one of the aspects of the present invention is the treatment of PC by inhibiting or silencing the expression of both the mutant and wildtype forms of any of the four keratin genes associated with PC (K6a, K6b, K16, and K17).

Figure 5:
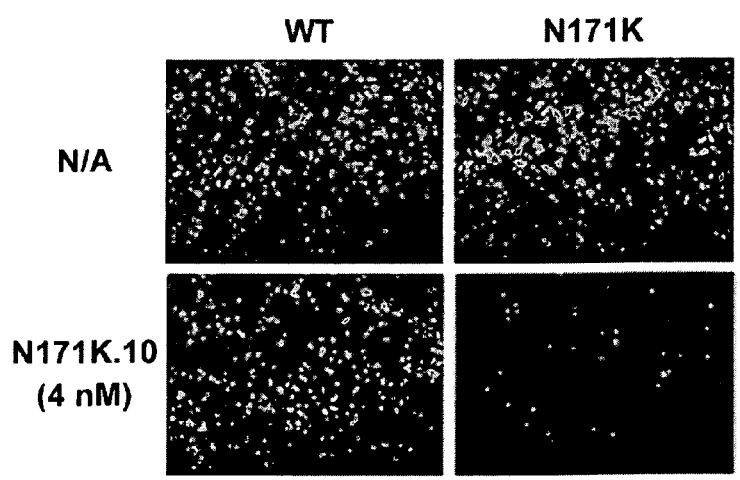
FIG. 5 shows images of cells visualized by fluorescence microscopy (Olympus CK40) 48 hours following transfection using an eGFP filter set. 293FT cells were co-transfected (Lipofectamine 2000) on 48-well tissue culture plates with 200 ng K6a(WT)/YFP or K6a(N171K)/YFP expression plasmid and the indicated amount of siRNA supplemented with pUC19 to give a final nucleic acid concentration of 400 ng per transfection. No changes in cell density or morphology were observed by bright field imaging (data not shown).
Figure 6:
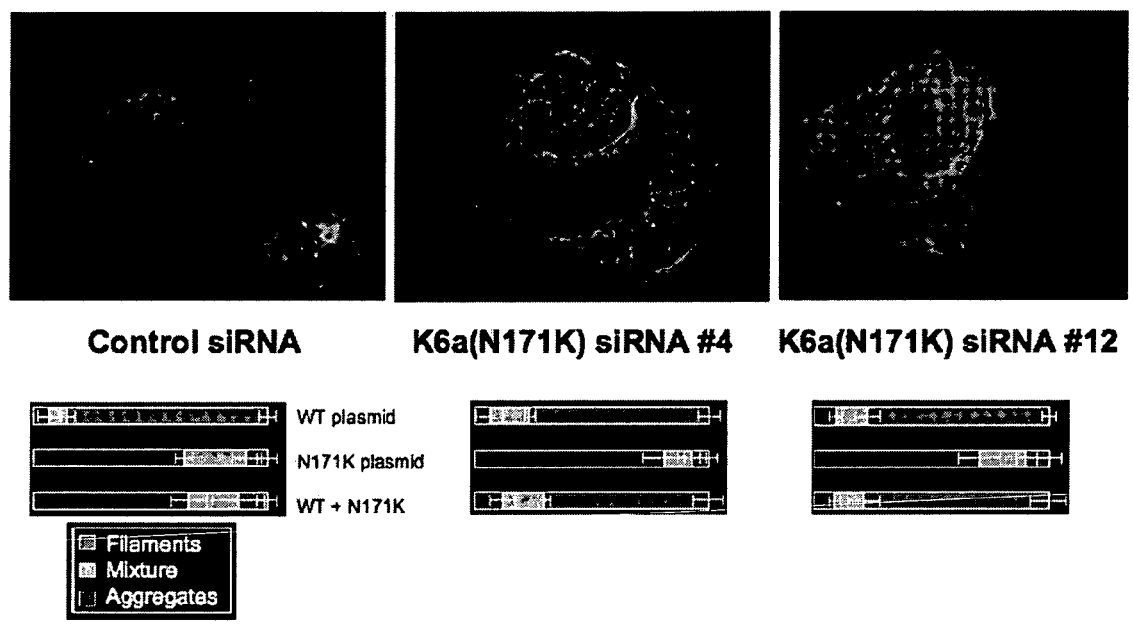
FIG. 6 shows images demonstrating how treatment with K6a mutant-specific siRNA prevents disease phenotype (keratin aggregates) in a "dominant negative disease" tissue culture model of pachyonychia congenita. PLC cells were co-transfected with a mixture of both K6a(WT)/YFP and K6a(N171K)/YFP expression plasmids (200 ng total) and either no siRNA (data not shown), 1 nM of non-specific control NSC4, N171K.4, or N171K.12 siRNA (N171K.4 and N171K.12 are specific for the K6a N171K mutation derived from a PC patient), supplemented with pUC19 to give a final nucleic acid concentration of 400 ng per transfection. 48 hours following transfection (Lipofectamine 2000), the cells were fixed, stained with DAPI and imaged by fluorescence microscopy. The images were analyzed and categorized as containing predominantly aggregates, predominantly filaments, or a mixture. (The histograms show the categorization results of the transfection experiments.)

To further demonstrate the specificity levels which can be achieved using the siRNA inhibition of the present invention, 239FT cells were co-transfected (Lipofectamine 2000) on 48-well tissue culture plates with 200 ng K6a(WT/YFP) or K6a(N171K)/YFP expression plasmid and the indicated amount of siRNA supplemented with pUC19 to give a final nucleic acid concentration of 400 ng per transfection. Cells were visualized by fluorescence microscopy 48 hours following transfection. FIG. 5 shows the exquisite specificity of the tested siRNA inhibitors; N171K.10 (SEQ ID NO 638) inhibits its specific target, while having no effect on other similar targets (i.e. N171K.10 has no affect on expression of K6a (N171K)/YFP at a 4 nM siRNA concentration.

Preferential Inhibition of Mutant K6a Results in Normal Keratin Filament Formation The siRNA inhibitors shown in FIG. 4 to selectively target mutant K6a/YFP over wildtype were used to determine whether mutant-specific siRNAs can preferentially inhibit mutant K6a protein synthesis in cells that have been transfected with a mixture of both mutant and wildtype K6a expression constructs (tissue culture model for autosomal dominant negative PC disorder). The ability of the inhibitors to preferentially inhibit mutant K6a was assayed by analyzing the percentage of cells in which keratin filaments were normal or disorganized (aggregates). Cells that were transfected with a mixture of expression plasmids without siRNA inhibitors (data not shown) or with 1 nM NCS4 siRNA were defective in keratin filament formation (<20% contained filaments). Co-transfection of cells with 1 nM N171K.4 or N171K.12 rescued the ability to form keratin filaments (<20% of the cells contained aggregates). These results suggest that RNA-based inhibitors can be designed and produced to be specific and highly effective against the K6a mutations (including single nucleotide mutations) responsible for PC, and suggest that siRNAs developed against molecular targets, such as those responsible for PC, may be effective therapeutics if delivered efficiently.

Inhibition of Both Mutant and Wildtype K6a

Figure 7:
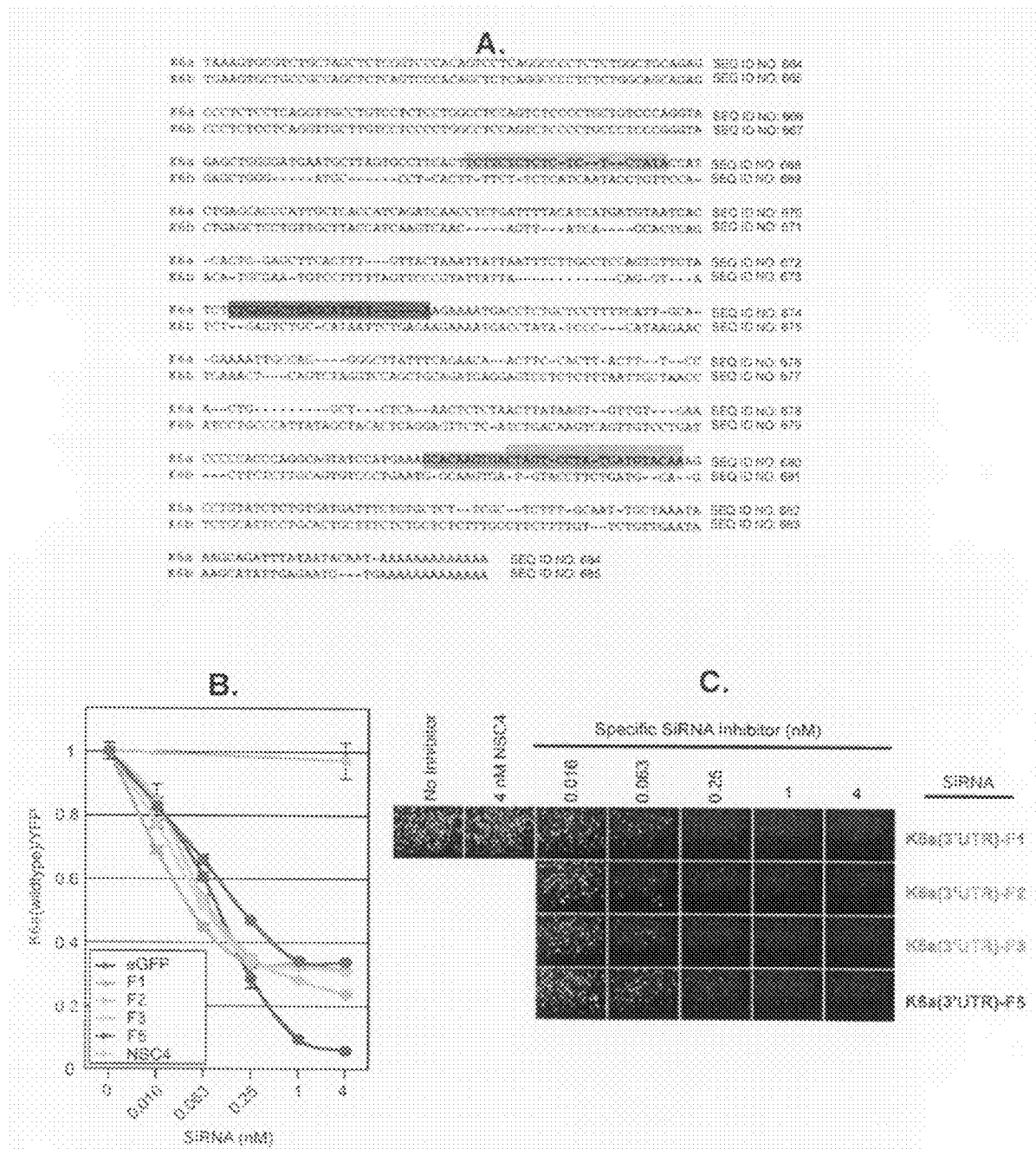
FIG. 7A shows the design of siRNAs targeting the K6a 3'UTR. The coding regions of K6a and K6b are nearly identical, while regions of their 3'UTRs differ. Four siRNAs were designed and synthesized (F1, F2, F3 and F5; sequence of siRNA is color coded, see key in Panel B). The corresponding region of K6b is shown for comparison. Panel B shows co-transfection (Lipofectamine 2000) results of 293FT cells on a 48-well tissue culture plate with 200 ng K6a(3'UTR)/YFP and the indicated amount of siRNA (supplemented with pUC19 to give a final nucleic acid concentration of 800 ng per transfection). 48 hours following transfection, the cells were analyzed by FACS. Panel C shows the cells of panel B as they were visualized by fluorescence microscopy (Olympus CK40) 48 hours following transfection using an eGFP filter set. No changes in cell density or morphology were observed by bright field imaging (data not shown).

As stated above, it is believed that redundancy of keratin expression in keratinocytes allows for the reduction of expression of one keratin gene without causing adverse side-effects. For example, knockout mouse experiments predict that inhibition of both wildtype and mutant K6a will be compensated by K6b. Slightly complicating this approach is the near identity of K6a and K6b in their coding regions; therefore, in order to achieve the necessary specificity the siRNA inhibitors are designed against the 3'UTR region where there are many differences between the two genes (FIG. 7).

SiRNA inhibitors were designed and tested in human 293FT tissue culture cells against wildtype K6a. FIG. 7A shows the designed and synthesized sequences targeting the K6a 3'UTR; the corresponding region of K6b is shown for comparison purposes. K6a-specific, eGFP-specific or non-specific siRNAs were co-transfected into human 293FT embryonic kidney cells with plasmids that express K6a (3'UTR)/YFP (contains the K6a 3'UTR). FIGS. 7B-C show that the K6a-3'UTR-specific siRNAs (F1, F2, F3 and F5) robustly inhibit K6a expression (IC50 values between 0.05 and 0.3 nM as determined by FACS analysis). As a positive control, eGFP-specific siRNA inhibitors were co-transfected with the K6a(3'UTR)/YFP construct (IC50 value was ~0.2 nM). No effect was observed with the irrelevant control (NSC4) siRNA inhibitor.

Figure 8:
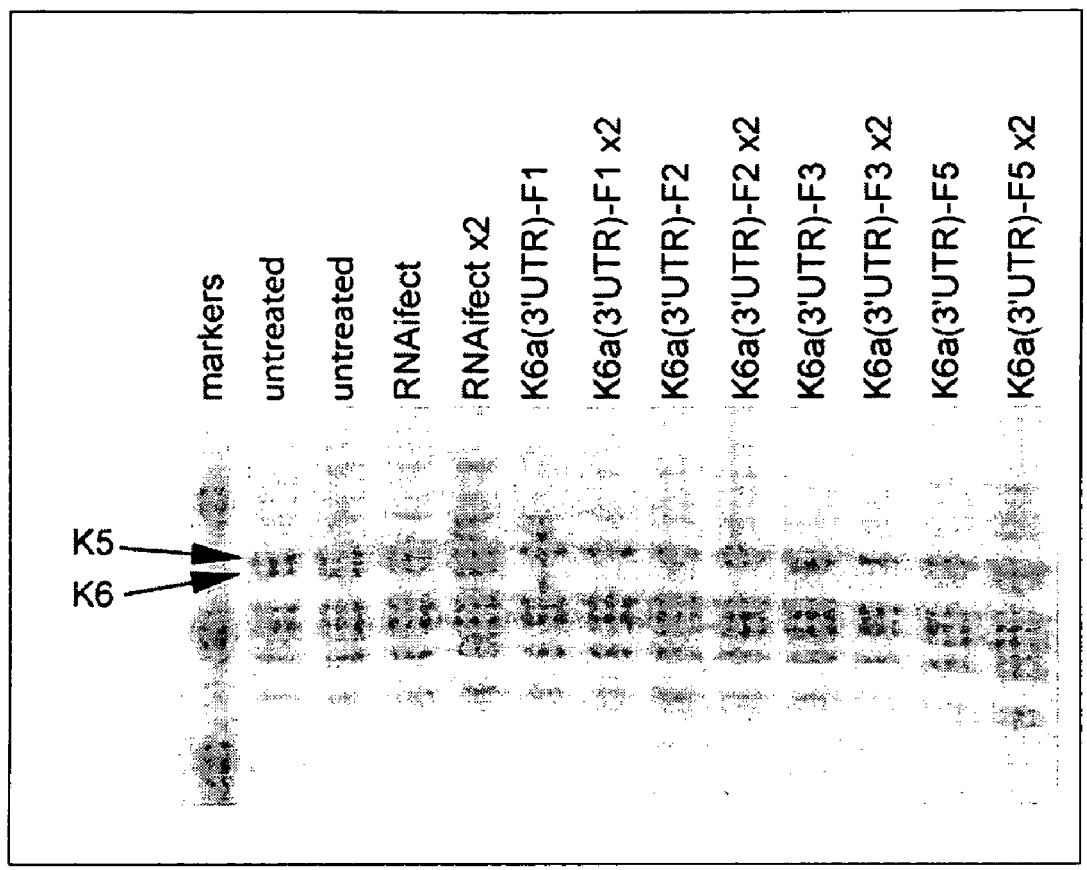
FIG. 8 shows an image of a gel in which endogenous K6a expression in HaCaT cells was inhibited by transfection of siRNAs (HaCaT cells express K6a but not K6b). HaCaT cells were plated at $2.5 \times 10^5$ cells per 3 cm plate in DMEM-10% FBS. The cells were transfected 24 hours later at approximately 60% confluency with 5 μg siRNA using RNAifect (Qiagen) according to the manufacturer's protocol. 72 hours following transfection, the cells were confluent and each plate was subcultured into four 3 cm plates. Two of these plates were transfected with a second aliquot of siRNA 24 hours post subculture, as above. The remaining two plates received no further treatment. Cytoskeletal extracts were prepared as previously described using low salt and high salt extraction buffers from two plates at 120 hours and 166 hours (not shown) post initial transfection (one plate with one treatment of siRNA and another with two treatments for each timepoint). Cytoskeletal extracts were resolved on NuPage 4-12% Bis-Tris gels (Novex) using MOPS running buffer. Gels were stained with Simply Blue Safe stain (Invitrogen).
Figure 9:
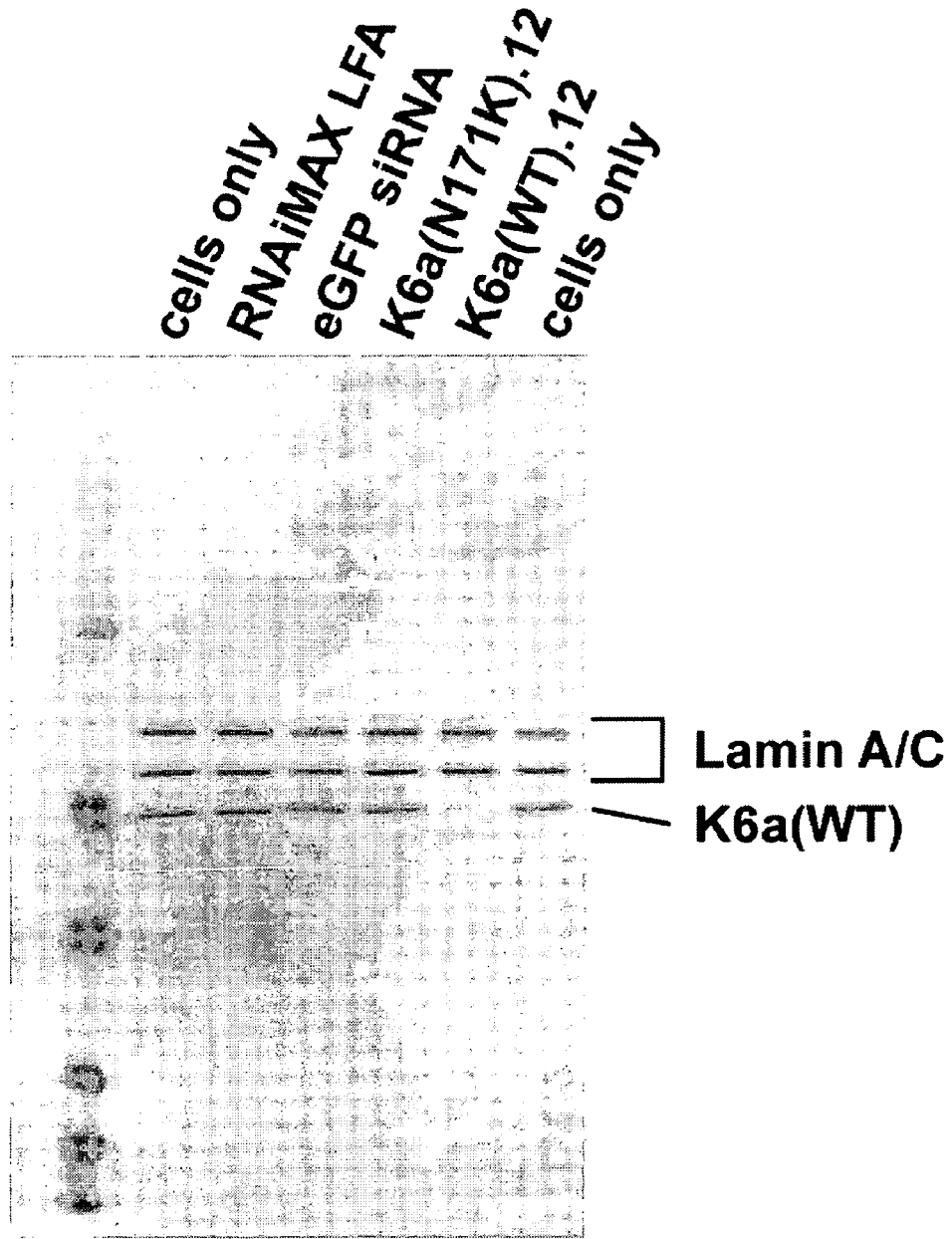
FIG. 9 shows an image of a western blot showing inhibition of endogenous K6a by siRNAs in transfected HaCaT cells (HaCaT cells express wildtype but not mutant K6a). HaCaT cells ($0.25 \times 10^5$ per well) were transfected with 50 nM wild-type and mutant siRNA #12 using RNAiMAX Lipofectamine following the manufacture's instructions for reverse transfection (Invitrogen) in a 48-well plate. 96 hrs later, cells were harvested and lysed in SDS-PAGE loading buffer, resolved by denaturing SDS-PAGE analysis, and electroblotted to nitrocellulose. K6 expression was detected by specific K6 antibody (Progen) and visualized using the NBT/BCIP system (Promega) using a secondary antibody (goat anti-mouse IgG) conjugated to alkaline phosphatase (Santa Cruz Biotech). The blot was subsequently reacted with an antibody specific to Lamin A/C (Upstate) to show equal lane loading and absence of generalized inhibition resulting from siRNA treatment. These results show that K6a can be inhibited with single-nucleotide specificity.

SiRNA-Mediated Down-Regulation of Pre-Existing K6a Expression in Human Keratinocytes Human HaCaT keratinocytes were transfected with K6a-specific siRNAs to test their ability to inhibit endogenous K6a. Cells were subcultured 72 hours post transfection and on half of the plates siRNA transfection was repeated. Cytoskeletal extracts were prepared at 120 hours, and again at 166 hours post-transfection from cells transfected either once or twice with siRNA. As shown in FIG. 8, for the 120 hour extracts a strong band was seen for K6a in untreated HaCaT cells and those treated with the transfection reagent RNAifect. In HaCaT cells transfected with any of the four K6a siRNAs (F1, F2, F3 or F5), a dramatic reduction in the amount of K6a protein was observed. Similar results were obtained from samples extracted at 166 hours post initial transfection. The amount of all other cytoskeletal proteins appears to be unaffected. The K6 band seen in the cytoskeletal extracts is predominantly K6a, confirmed by RT-PCR analysis (data not shown). Messenger RNA derived from untreated HaCaT cells was amplified by RT-PCR using primers specific for K6a or K6b. A positive band was observed for K6a but there is no/very little K6b present in HaCaT cells. This gel system provides a quick way to check the efficiency of K6a siRNA inhibitors on endogenous K6a in HaCaT cells. These results were confirmed by western blot analysis.

Delivery and Effectiveness of siRNA Inhibitors in Mouse Footpad Keratinocytes

Figure 10:
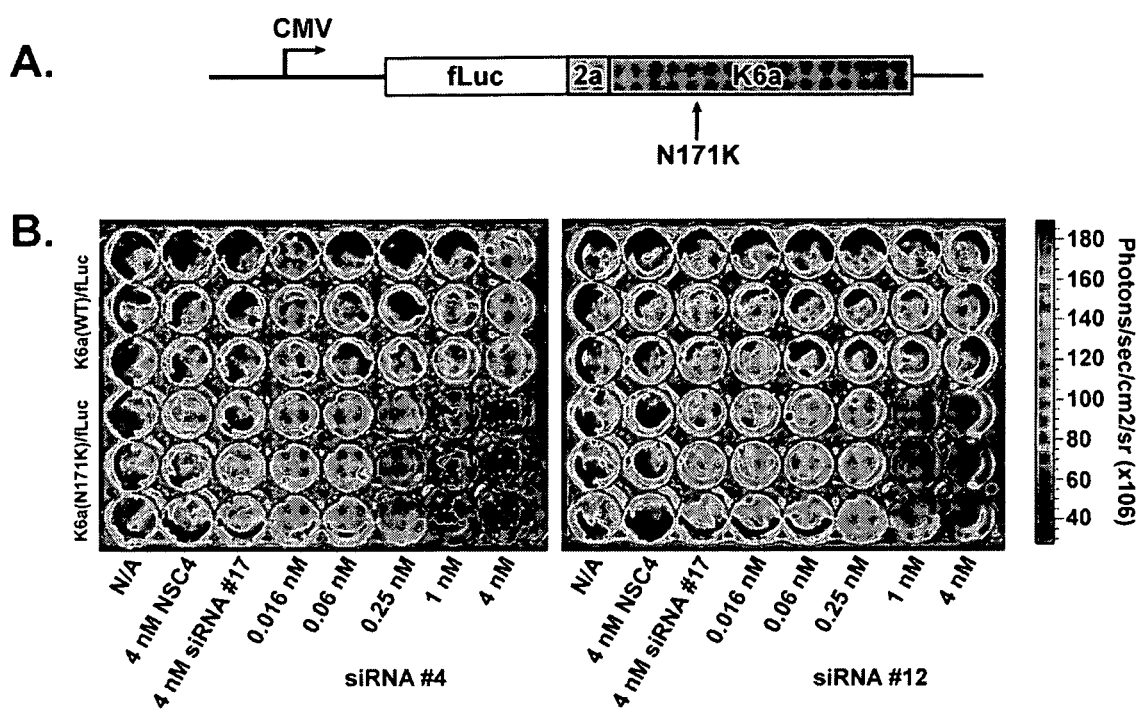
FIG. 10A shows a schematic of pL2K6a(N171K) bicistronic expression plasmid (expresses a hybrid fLuc-2a-K6a-N171K mRNA under the control of the CMV promoter) with target region of mutant K6a inhibitor noted. The bicistronic nature of this reporter is conferred by the foot and mouth viral disease (FMVD) 2a ribosome slippage element. Panel B shows that this construct (and its wildtype K6a counterpart) is expressed in 293FT cells and that mutant specific siRNAs (K6a N171K.4 and N171K.12) inhibit expression of the mutant K6a version but not the wildtype. 293FT cells were transfected (using lipofectamine 2000) on 48-well plates with the indicated siRNAs and either the wildtype or mutant versions of pL2K6a bicistronic plasmid. 48 hours later, luciferin was added to each well and the amount of light emitted from intact cells (function of presence of fLuc) was measured using a Xenogen IVIS imaging system.
Figure 11A:
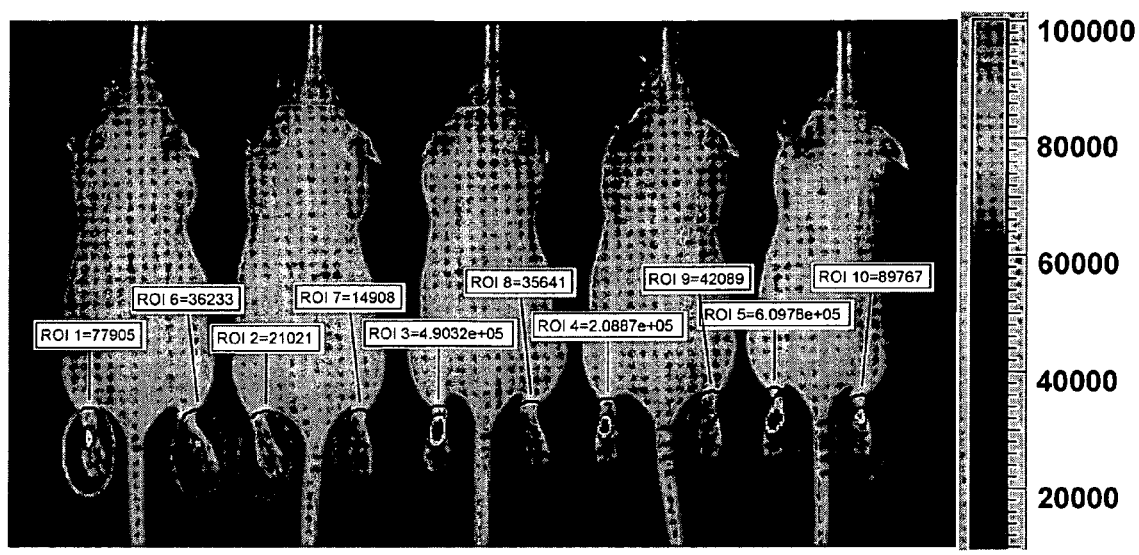
FIGS. 11A and 11B and 12 show inhibition of pL2K6a (N171K) gene expression by mutant-specific siRNAs in a footpad skin mouse model. Mice were co-injected intradermally with 10 μg of pL2K6a(N171K) expression plasmid with either 10 μg of K6a(N171K)-specific siRNA (N171K.4 or N171K.12) or irrelevant NSC4 siRNA (or the plasmid pUC19). At the indicated times, footpad luciferase expression (n=5 mice) was determined following IP luciferin injection by whole animal imaging using the Xenogen IVIS in vivo imaging system (FIG. 11A, red expression is highest, purple lowest; images for mice treated with pUC19 or N171K.4 siRNA are not shown) and quantitated (FIGS. 11B and 12) using Living Image software (Xenogen). The bolded line represents the average of the 5 mice per treatment group.
Figure 11B:
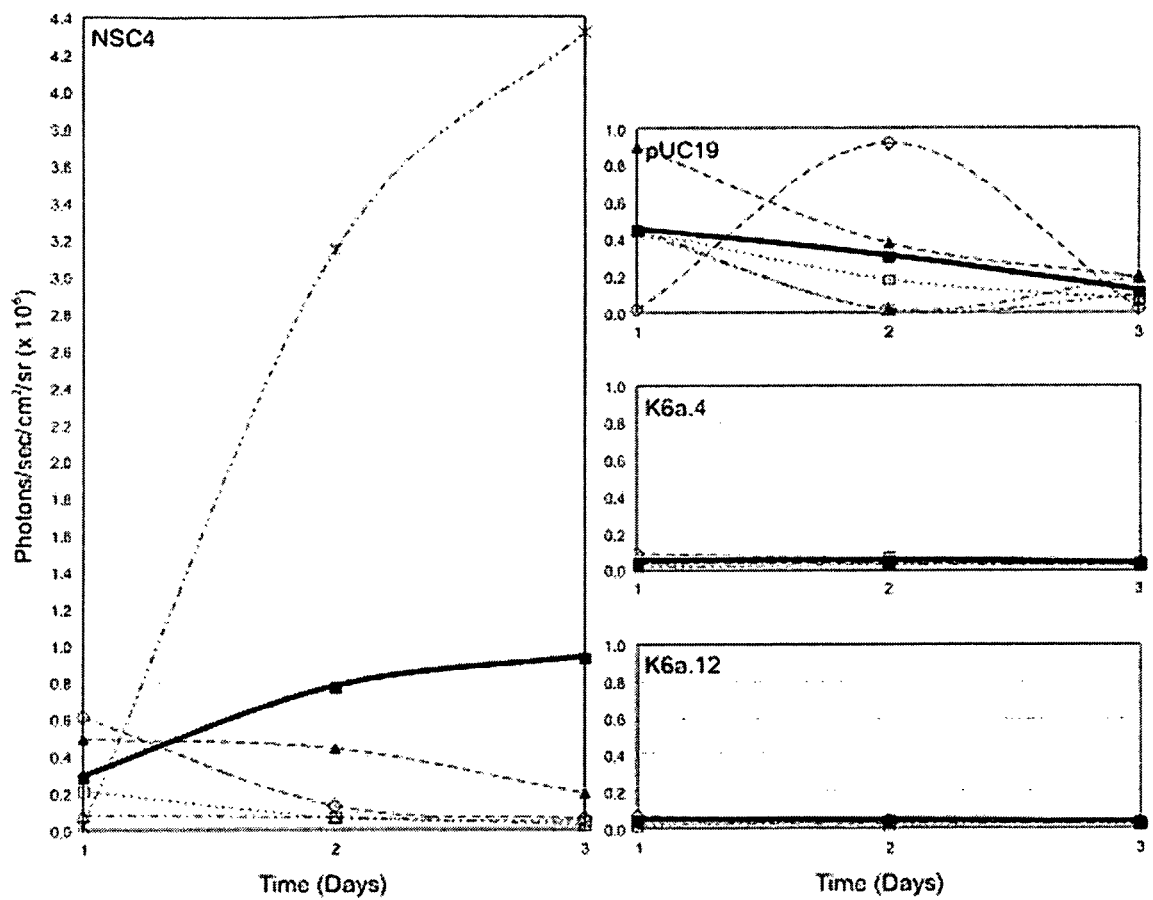
Figure 12:
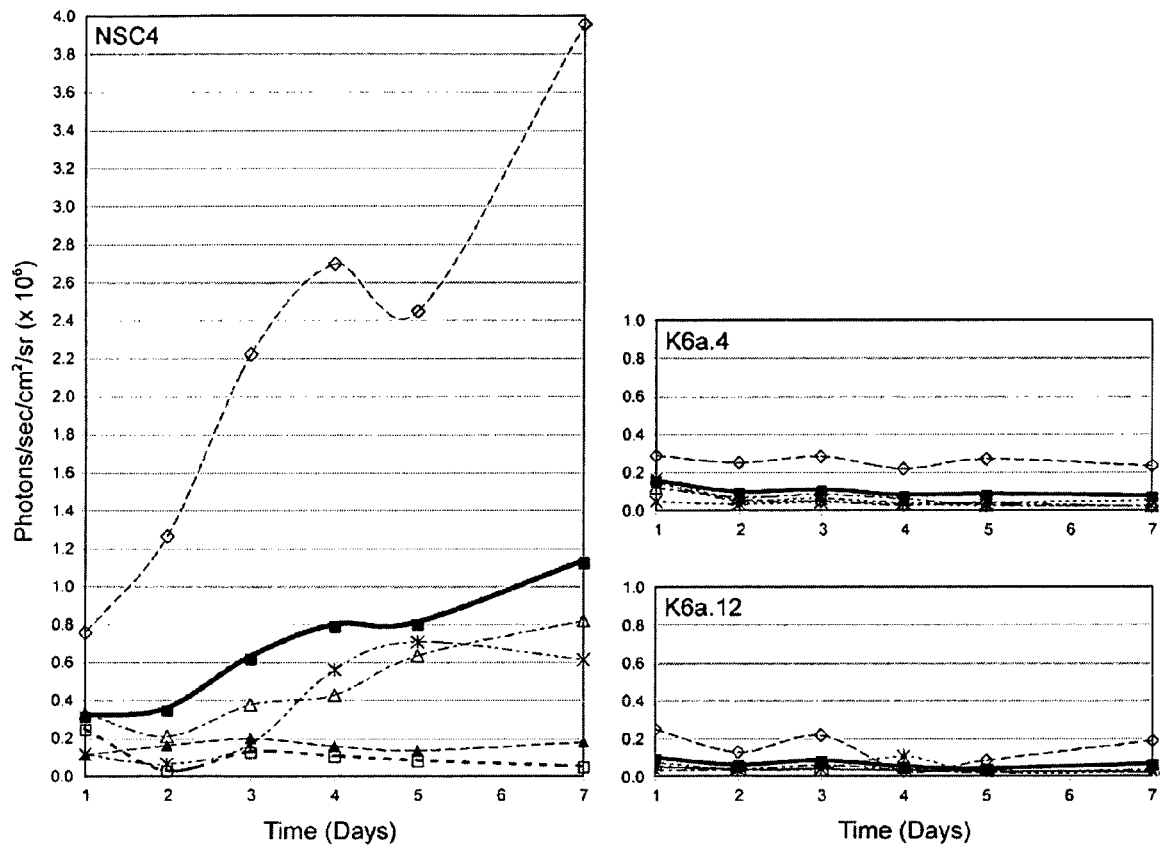

Female FVB mouse footpads were intradermally injected with a reporter gene/K6a (wt or N171K mutant) plasmid (pL2K6a(N171K), as shown in FIG. 10A) encoding a bicistronic mRNA comprised of the firefly luciferase and K6a open reading frames separated by the foot and mouth virus 2a "ribosome slippage" sequence. The noninvasive analyses of gene expression afforded by this approach allows for the repeated monitoring of reporter gene expression over multiple timepoints in the same group of animals, minimizing the number of mice needed while refining the data sets and maximizing the amount of information obtained. The mice were imaged for luciferase expression at multiple timepoints (typically ranging from 12-120 hours) post gene delivery. FIG. 11A shows the image at the 24 hour timepoint (left paw was treated with control NSC4 siRNA and the right with N171K.12 siRNA). FIG. 11B shows data collected for mice treated with pUC19, NSC4, N171K.4, and N171K.12 collected over three days. FIG. 11A along with FIG. 12 shows a separate similar experiment in which the data were collected for seven days. Mouse footpad skin was chosen over other mouse skin in part due its greater thickness, the absence of hair follicles, ease of access, and relevance to PC.

It is to be understood that the above-described methods, formulations, and experimentals are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A method of treating pachyonychia congenita in a human subject comprising:
   a) identifying a genetic mutation contributing to pachyonychia congenita, said mutation occurring on a gene which encodes for a keratin selected from the group consisting of keratin 6a (K6a), keratin 6b (K6b), keratin 16 (K16), and keratin 17 (K17);
   b) preparing an RNA sequence that inhibits expression of said genetic mutation;
   c) transdermally administering said RNA sequence to a cell in the human subject having pachyonychia congenital, wherein the RNA sequence is selected from the group consisting of SEQ ID NO: 352, 480, 594 and 640 or combinations thereof.

2. The method of claim 1, wherein the RNA sequence is a small interfering RNA.

3. The method of claim 1, wherein the mutation is a single nucleotide mutation.

4. The method of claim 1, wherein the mutation is a deletion or insertion.

5. The method of claim 1, wherein the siRNA sequence is administered as double stranded RNA.

6. The method of claim 1, wherein the siRNA sequence is administered as a short hairpin RNA.

7. The method of claim 1, wherein the RNA sequence is administered to target cells of said subject using a formulation selected from the group consisting of injection, topical lotions, creams, gels, ointments, pastes, transdermal patches, electrophoresis, and combinations thereof.

8. The method of claim 1, wherein the RNA sequence is administered in a therapeutically effective amount of about 0.1 mg to about 10 mg.

9. The method of claim 1, wherein the RNA sequence contains at least one modified nucleotide.

10. The method of claim 1, wherein the RNA sequence is administered in combination with a therapeutically effective compound selected from the group consisting of corticosteroid, hydrocortisone, lanolin, aloe vera, urea, propylene glycol, a-hydroxy acids, lactic acid, salicylic acid, vitamin $D_3$ and its derivatives, vitamin A and retinoids, levothyroxin, NSAIDS, cyclosporine, methotrexate sodium, anthralin, acitretin, tazarotene, coal tar, clobetasol propionate, botulinum toxin, topical anesthetics, antihistamine, and combinations thereof.

11. A method of treating pachyonychia congenita in a human subject comprising:
   transdermally administering to target cells of the human subject an RNA sequence which inhibits expression of the gene encoding for a keratin selected from the group consisting of K6a, K6b, K16, K17, and combinations thereof wherein the RNA sequence is selected from the group consisting of SEQ ID NO: 352, 480, 594 and 640.

12. The method of claim 11, wherein the inhibited gene encodes for a mutated keratin.

13. The method of claim 11, wherein the inhibited gene encodes a wildtype keratin.

14. The method of claim 11, wherein the RNA sequence inhibits expression of both mutated and wildtype keratin genes.

15. The method of claim 11, wherein the RNA sequence is a small interfering RNA.

16. The method of claim 11, wherein the RNA sequence is administered as double stranded RNA.

17. The method of claim 11, wherein the RNA sequence is administered as a short hairpin RNA.

18. The method of claim 11, wherein the RNA sequence is administered to said subject in a formulation selected from the group consisting of injection, topical lotions, creams, gels, ointments, pastes, adhesives, transdermal patches, electrophoresis, and combinations thereof.

19. The method of claim 11, wherein the RNA sequence is administered in a therapeutically effective amount of about 0.1 mg to about 10 mg.

20. The method of claim 11, wherein the RNA sequence contains at least one modified nucleotide.

21. An RNA sequence which inhibits the expression of the gene encoding for K6a keratin selected from the group consisting of: SEQ ID NO:640.

22. The RNA sequence of claim 21, wherein the RNA sequence contains at least one modified nucleotide.

23. The RNA sequence of claim 21, wherein the RNA sequence is configured to be delivered to a cell of a subject having pachyonychia congenita.

24. The RNA sequence of claim 21, wherein said RNA sequence is configured to form a short hairpin RNA.

25. A mixture of at least two RNA sequences, wherein said mixture comprises the RNA sequence of claim 21 and a sequence selected from the group consisting of SEQ ID NO: 3-31, 34-52, 55-69, 72-100,103-131, 134-146, 148-162,165-193, 196-223, 226-254, 257-285, 288-316, 319-347, 629-639, 641-658, and 661-663.

26. An RNA sequence which inhibits the expression of the gene encoding for K6b keratin selected from the group consisting of SEQ ID NO:352.

27. The RNA sequence of claim 26, wherein the RNA sequence contains at least one modified nucleotide.

28. The RNA sequence of claim 26, wherein the RNA sequence is configured to be delivered to a cell of a subject having pachyonychia congenita.

29. The RNA sequence of claim 26, wherein said RNA sequence is configured to form a short hairpin RNA.

30. A mixture of at least two RNA sequences, wherein said mixture comprises the RNA sequence of claim 26 and a sequence selected from the group consisting of SEQ ID NO: 350, 351, and 353-378.

31. An RNA sequence which inhibits the expression of the gene encoding for K16 keratin selected from the group consisting of: SEQ ID NO:480.

32. The RNA sequence of claim 31, wherein the RNA sequence contains at least one modified nucleotide.

33. The RNA sequence of claim 31, wherein the RNA sequence is configured to be delivered to a target cell in a subject having pachyonychia congenita.

34. The RNA sequence of claim 31, wherein said RNA sequence is configured to form a short hairpin RNA.

35. A mixture of at least two RNA sequences, wherein said mixture comprises the RNA sequence of claim 31 and a sequence selected from the group consisting of SEQ ID NO: 381-409, 412-440, 443-471, 474-502, 505-533, and 536-564.

36. An RNA sequence which inhibits the expression of the gene encoding for K17 keratin selected from the group consisting of: SEQ ID NO:594.

37. The RNA sequence of claim 36, wherein the RNA sequence contains at least one modified nucleotide.

38. The RNA sequence of claim 36, wherein the RNA sequence is configured to be delivered to a target cell of a subject having pachyonychia congenita.

39. The RNA sequence of claim 36, wherein said RNA sequence is configured to form a short hairpin RNA.

40. A mixture of at least two RNA sequences, wherein said mixture comprises the RNA sequence of claim 36 and a sequence selected from the group consisting of SEQ ID NO: 567-593, 595, and 598-626.

* * * * *

SEQUENCE LISTING

```
<160> NUMBER OF SEQ ID NOS: 685

<210> SEQ ID NO 1
<211> LENGTH: 88
<212> TYPE: DNA
<213> ORGANISM: Homo sapiens

<400> SEQUENCE: 1
ccagcgggtg cgggccgagg agcgtgaaca gatcaagacc ctcaacaaca agtttgcctc    60
cttcatcgac aaggtgcggt tcctggag                                       88

<210> SEQ ID NO 2
<211> LENGTH: 88
<212> TYPE: DNA
<213> ORGANISM: Homo sapiens

<400> SEQUENCE: 2
ccagcgggtg cgggccgagg agcgtgaaca gatcaagacc ctcaaaaaca agtttgcctc    60
cttcatcgac aaggtgcggt tcctggag                                       88

<210> SEQ ID NO 3
<211> LENGTH: 29
<212> TYPE: RNA
<213> ORGANISM: Artificial Sequence
<220> FEATURE:
<223> OTHER INFORMATION: oligonucleotide

<400> SEQUENCE: 3
aggagcguga acagaucaag acccucaaa                                      29

<210> SEQ ID NO 4
<211> LENGTH: 29
<212> TYPE: RNA
<213> ORGANISM: Artificial Sequence
<220> FEATURE:
<223> OTHER INFORMATION: oligonucleotide

<400> SEQUENCE: 4
ggagcgugaa cagaucaaga cccucaaaa                                      29

<210> SEQ ID NO 5
<211> LENGTH: 29
<212> TYPE: RNA
<213> ORGANISM: Artificial Sequence
<220> FEATURE:
<223> OTHER INFORMATION: oligonucleotide
```

-continued

```
<400> SEQUENCE: 5
gagcgugaac agaucaagac ccucaaaaa                                          29

<210> SEQ ID NO 6
<211> LENGTH: 29
<212> TYPE: RNA
<213> ORGANISM: Artificial Sequence
<220> FEATURE:
<223> OTHER INFORMATION: oligonucleotide

<400> SEQUENCE: 6
agcgugaaca gaucaagacc cucaaaaac                                          29

<210> SEQ ID NO 7
<211> LENGTH: 29
<212> TYPE: RNA
<213> ORGANISM: Artificial Sequence
<220> FEATURE:
<223> OTHER INFORMATION: oligonucleotide

<400> SEQUENCE: 7
gcgugaacag aucaagaccc ucaaaaaca                                          29

<210> SEQ ID NO 8
<211> LENGTH: 29
<212> TYPE: RNA
<213> ORGANISM: Artificial Sequence
<220> FEATURE:
<223> OTHER INFORMATION: oligonucleotide

<400> SEQUENCE: 8
cgugaacaga ucaagacccu caaaaacaa                                          29

<210> SEQ ID NO 9
<211> LENGTH: 29
<212> TYPE: RNA
<213> ORGANISM: Artificial Sequence
<220> FEATURE:
<223> OTHER INFORMATION: oligonucleotide

<400> SEQUENCE: 9
gugaacagau caagacccuc aaaaacaag                                          29

<210> SEQ ID NO 10
<211> LENGTH: 29
<212> TYPE: RNA
<213> ORGANISM: Artificial Sequence
<220> FEATURE:
<223> OTHER INFORMATION: oligonucleotide

<400> SEQUENCE: 10
ugaacagauc aagacccuca aaaacaagu                                          29

<210> SEQ ID NO 11
<211> LENGTH: 29
<212> TYPE: RNA
<213> ORGANISM: Artificial Sequence
<220> FEATURE:
<223> OTHER INFORMATION: oligonucleotide

<400> SEQUENCE: 11
gaacagauca agacccucaa aaacaaguu                                          29
```

<210> SEQ ID NO 12
<211> LENGTH: 29
<212> TYPE: RNA
<213> ORGANISM: Artificial Sequence
<220> FEATURE:
<223> OTHER INFORMATION: oligonucleotide

<400> SEQUENCE: 12
aacagaucaa gacccucaaa aacaaguuu                                    29

<210> SEQ ID NO 13
<211> LENGTH: 29
<212> TYPE: RNA
<213> ORGANISM: Artificial Sequence
<220> FEATURE:
<223> OTHER INFORMATION: oligonucleotide

<400> SEQUENCE: 13
acagaucaag acccucaaaa acaaguuug                                    29

<210> SEQ ID NO 14
<211> LENGTH: 29
<212> TYPE: RNA
<213> ORGANISM: Artificial Sequence
<220> FEATURE:
<223> OTHER INFORMATION: oligonucleotide

<400> SEQUENCE: 14
cagaucaaga cccucaaaaa caaguuugc                                    29

<210> SEQ ID NO 15
<211> LENGTH: 29
<212> TYPE: RNA
<213> ORGANISM: Artificial Sequence
<220> FEATURE:
<223> OTHER INFORMATION: oligonucleotide

<400> SEQUENCE: 15
agaucaagac ccucaaaaac aaguuugcc                                    29

<210> SEQ ID NO 16
<211> LENGTH: 29
<212> TYPE: RNA
<213> ORGANISM: Artificial Sequence
<220> FEATURE:
<223> OTHER INFORMATION: oligonucleotide

<400> SEQUENCE: 16
gaucaagacc cucaaaaaca aguuugccu                                    29

<210> SEQ ID NO 17
<211> LENGTH: 29
<212> TYPE: RNA
<213> ORGANISM: Artificial Sequence
<220> FEATURE:
<223> OTHER INFORMATION: oligonucleotide

<400> SEQUENCE: 17
aucaagaccc ucaaaacaa guuugccuc                                     29

<210> SEQ ID NO 18
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 18
ucaagacccu caaaaacaag uuugccucc                                  29

<210> SEQ ID NO 19
<211> LENGTH: 29
<212> TYPE: RNA
<213> ORGANISM: Artificial Sequence
<220> FEATURE:
<223> OTHER INFORMATION: oligonucleotide

<400> SEQUENCE: 19
caagacccuc aaaaacaagu uugccuccu                                  29

<210> SEQ ID NO 20
<211> LENGTH: 29
<212> TYPE: RNA
<213> ORGANISM: Artificial Sequence
<220> FEATURE:
<223> OTHER INFORMATION: oligonucleotide

<400> SEQUENCE: 20
aagacccuca aaacaaguu ugccuccuu                                   29

<210> SEQ ID NO 21
<211> LENGTH: 29
<212> TYPE: RNA
<213> ORGANISM: Artificial Sequence
<220> FEATURE:
<223> OTHER INFORMATION: oligonucleotide

<400> SEQUENCE: 21
agacccucaa aaacaaguuu gccuccuuc                                  29

<210> SEQ ID NO 22
<211> LENGTH: 29
<212> TYPE: RNA
<213> ORGANISM: Artificial Sequence
<220> FEATURE:
<223> OTHER INFORMATION: oligonucleotide

<400> SEQUENCE: 22
gacccucaaa aacaaguuug ccuccuuca                                  29

<210> SEQ ID NO 23
<211> LENGTH: 29
<212> TYPE: RNA
<213> ORGANISM: Artificial Sequence
<220> FEATURE:
<223> OTHER INFORMATION: oligonucleotide

<400> SEQUENCE: 23
acccucaaaa acaaguuugc cuccuucau                                  29

<210> SEQ ID NO 24
<211> LENGTH: 29
<212> TYPE: RNA
<213> ORGANISM: Artificial Sequence
<220> FEATURE:
<223> OTHER INFORMATION: oligonucleotide

<400> SEQUENCE: 24
cccucaaaaa caaguuugcc uccuucauc                                  29
```

<210> SEQ ID NO 25
<211> LENGTH: 29
<212> TYPE: RNA
<213> ORGANISM: Artificial Sequence
<220> FEATURE:
<223> OTHER INFORMATION: oligonucleotide

<400> SEQUENCE: 25
ccucaaaaac aaguuugccu ccuucaucg                                29

<210> SEQ ID NO 26
<211> LENGTH: 29
<212> TYPE: RNA
<213> ORGANISM: Artificial Sequence
<220> FEATURE:
<223> OTHER INFORMATION: oligonucleotide

<400> SEQUENCE: 26
cucaaaaaca aguuugccuc cuucaucga                                29

<210> SEQ ID NO 27
<211> LENGTH: 29
<212> TYPE: RNA
<213> ORGANISM: Artificial Sequence
<220> FEATURE:
<223> OTHER INFORMATION: oligonucleotide

<400> SEQUENCE: 27
ucaaaaacaa guuugccucc uucaucgac                                29

<210> SEQ ID NO 28
<211> LENGTH: 29
<212> TYPE: RNA
<213> ORGANISM: Artificial Sequence
<220> FEATURE:
<223> OTHER INFORMATION: oligonucleotide

<400> SEQUENCE: 28
caaaaacaag uuugccuccu ucaucgaca                                29

<210> SEQ ID NO 29
<211> LENGTH: 29
<212> TYPE: RNA
<213> ORGANISM: Artificial Sequence
<220> FEATURE:
<223> OTHER INFORMATION: oligonucleotide

<400> SEQUENCE: 29
aaaaacaagu uugccuccuu caucgacaa                                29

<210> SEQ ID NO 30
<211> LENGTH: 29
<212> TYPE: RNA
<213> ORGANISM: Artificial Sequence
<220> FEATURE:
<223> OTHER INFORMATION: oligonucleotide

<400> SEQUENCE: 30
aaaacaaguu ugccuccuuc aucgacaag                                29

<210> SEQ ID NO 31
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 31
aaacaaguuu gccuccuuca ucgacaagg                                29

<210> SEQ ID NO 32
<211> LENGTH: 88
<212> TYPE: DNA
<213> ORGANISM: Homo sapiens

<400> SEQUENCE: 32
ccagcgggtg cgggccgagg agcgtgaaca gatcaagacc ctcaacaaca agtttgcctc    60
cttcatcgac aaggtgcggt tcctggag                                      88

<210> SEQ ID NO 33
<211> LENGTH: 88
<212> TYPE: DNA
<213> ORGANISM: Homo sapiens

<400> SEQUENCE: 33
ccagcgggtg cgggccgagg agcgtgaaca gatcaagacc ctcaaaaaca agtttgcctc    60
cttcatcgac aaggtgcggt tcctggag                                      88

<210> SEQ ID NO 34
<211> LENGTH: 19
<212> TYPE: RNA
<213> ORGANISM: Artificial Sequence
<220> FEATURE:
<223> OTHER INFORMATION: oligonucleotide

<400> SEQUENCE: 34
acagaucaag acccucaaa                                           19

<210> SEQ ID NO 35
<211> LENGTH: 19
<212> TYPE: RNA
<213> ORGANISM: Artificial Sequence
<220> FEATURE:
<223> OTHER INFORMATION: oligonucleotide

<400> SEQUENCE: 35
cagaucaaga cccucaaaa                                           19

<210> SEQ ID NO 36
<211> LENGTH: 19
<212> TYPE: RNA
<213> ORGANISM: Artificial Sequence
<220> FEATURE:
<223> OTHER INFORMATION: oligonucleotide

<400> SEQUENCE: 36
agaucaagac ccucaaaaa                                           19

<210> SEQ ID NO 37
<211> LENGTH: 19
<212> TYPE: RNA
<213> ORGANISM: Artificial Sequence
<220> FEATURE:
<223> OTHER INFORMATION: oligonucleotide

<400> SEQUENCE: 37
gaucaagacc cucaaaaac                                           19
```

<210> SEQ ID NO 38
<211> LENGTH: 19
<212> TYPE: RNA
<213> ORGANISM: Artificial Sequence
<220> FEATURE:
<223> OTHER INFORMATION: oligonucleotide

<400> SEQUENCE: 38
aucaagaccc ucaaaaaca                                                19

<210> SEQ ID NO 39
<211> LENGTH: 19
<212> TYPE: RNA
<213> ORGANISM: Artificial Sequence
<220> FEATURE:
<223> OTHER INFORMATION: oligonucleotide

<400> SEQUENCE: 39
ucaagacccu caaaacaa                                                 19

<210> SEQ ID NO 40
<211> LENGTH: 19
<212> TYPE: RNA
<213> ORGANISM: Artificial Sequence
<220> FEATURE:
<223> OTHER INFORMATION: oligonucleotide

<400> SEQUENCE: 40
caagacccuc aaaacaag                                                 19

<210> SEQ ID NO 41
<211> LENGTH: 19
<212> TYPE: RNA
<213> ORGANISM: Artificial Sequence
<220> FEATURE:
<223> OTHER INFORMATION: oligonucleotide

<400> SEQUENCE: 41
aagacccuca aaacaagu                                                 19

<210> SEQ ID NO 42
<211> LENGTH: 19
<212> TYPE: RNA
<213> ORGANISM: Artificial Sequence
<220> FEATURE:
<223> OTHER INFORMATION: oligonucleotide

<400> SEQUENCE: 42
agacccucaa aacaaguu                                                 19

<210> SEQ ID NO 43
<211> LENGTH: 19
<212> TYPE: RNA
<213> ORGANISM: Artificial Sequence
<220> FEATURE:
<223> OTHER INFORMATION: oligonucleotide

<400> SEQUENCE: 43
gacccucaaa aacaaguuu                                                19

<210> SEQ ID NO 44
<211> LENGTH: 19
<212> TYPE: RNA
<213> ORGANISM: Artificial Sequence
<220> FEATURE:
<223> OTHER INFORMATION: oligonucleotide

```
<400> SEQUENCE: 44
acccucaaaa acaaguuug                                              19

<210> SEQ ID NO 45
<211> LENGTH: 19
<212> TYPE: RNA
<213> ORGANISM: Artificial Sequence
<220> FEATURE:
<223> OTHER INFORMATION: oligonucleotide

<400> SEQUENCE: 45
cccucaaaaa caaguuugc                                              19

<210> SEQ ID NO 46
<211> LENGTH: 19
<212> TYPE: RNA
<213> ORGANISM: Artificial Sequence
<220> FEATURE:
<223> OTHER INFORMATION: oligonucleotide

<400> SEQUENCE: 46
ccucaaaaac aaguuugcc                                              19

<210> SEQ ID NO 47
<211> LENGTH: 19
<212> TYPE: RNA
<213> ORGANISM: Artificial Sequence
<220> FEATURE:
<223> OTHER INFORMATION: oligonucleotide

<400> SEQUENCE: 47
cucaaaaaca aguuugccu                                              19

<210> SEQ ID NO 48
<211> LENGTH: 19
<212> TYPE: RNA
<213> ORGANISM: Artificial Sequence
<220> FEATURE:
<223> OTHER INFORMATION: oligonucleotide

<400> SEQUENCE: 48
ucaaaaacaa guuugccuc                                              19

<210> SEQ ID NO 49
<211> LENGTH: 19
<212> TYPE: RNA
<213> ORGANISM: Artificial Sequence
<220> FEATURE:
<223> OTHER INFORMATION: oligonucleotide

<400> SEQUENCE: 49
caaaaacaag uuugccucc                                              19

<210> SEQ ID NO 50
<211> LENGTH: 19
<212> TYPE: RNA
<213> ORGANISM: Artificial Sequence
<220> FEATURE:
<223> OTHER INFORMATION: oligonucleotide

<400> SEQUENCE: 50
aaaaacaagu uugccuccu                                              19
```

```
<210> SEQ ID NO 51
<211> LENGTH: 19
<212> TYPE: RNA
<213> ORGANISM: Artificial Sequence
<220> FEATURE:
<223> OTHER INFORMATION: oligonucleotide

<400> SEQUENCE: 51 aaacaaguu ugccuccuu                                                       19

<210> SEQ ID NO 52
<211> LENGTH: 19
<212> TYPE: RNA
<213> ORGANISM: Artificial Sequence
<220> FEATURE:
<223> OTHER INFORMATION: oligonucleotide

<400> SEQUENCE: 52
aaacaaguuu gccuccuuc                                                      19

<210> SEQ ID NO 53
<211> LENGTH: 88
<212> TYPE: DNA
<213> ORGANISM: Homo sapiens

<400> SEQUENCE: 53
ccagcgggtg cgggccgagg agcgtgaaca gatcaagacc ctcaacaaca agtttgcctc         60
cttcatcgac aaggtgcggt tcctggag                                            88

<210> SEQ ID NO 54
<211> LENGTH: 88
<212> TYPE: DNA
<213> ORGANISM: Homo sapiens

<400> SEQUENCE: 54
ccagcgggtg cgggccgagg agcgtgaaca gatcaagacc ctcaaaaaca agtttgcctc         60
cttcatcgac aaggtgcggt tcctggag                                            88

<210> SEQ ID NO 55
<211> LENGTH: 15
<212> TYPE: RNA
<213> ORGANISM: Artificial Sequence
<220> FEATURE:
<223> OTHER INFORMATION: oligonucleotide

<400> SEQUENCE: 55 aucaagacccc ucaaa                                                         15

<210> SEQ ID NO 56
<211> LENGTH: 15
<212> TYPE: RNA
<213> ORGANISM: Artificial Sequence
<220> FEATURE:
<223> OTHER INFORMATION: oligonucleotide

<400> SEQUENCE: 56
ucaagacccu caaaa                                                          15

<210> SEQ ID NO 57
<211> LENGTH: 15
<212> TYPE: RNA
<213> ORGANISM: Artificial Sequence
<220> FEATURE:
<223> OTHER INFORMATION: oligonucleotide
```

```
<400> SEQUENCE: 57
caagacccuc aaaaa                                                    15

<210> SEQ ID NO 58
<211> LENGTH: 15
<212> TYPE: RNA
<213> ORGANISM: Artificial Sequence
<220> FEATURE:
<223> OTHER INFORMATION: oligonucleotide

<400> SEQUENCE: 58
aagacccuca aaaac                                                    15

<210> SEQ ID NO 59
<211> LENGTH: 15
<212> TYPE: RNA
<213> ORGANISM: Artificial Sequence
<220> FEATURE:
<223> OTHER INFORMATION: oligonucleotide

<400> SEQUENCE: 59
agacccucaa aaaca                                                    15

<210> SEQ ID NO 60
<211> LENGTH: 15
<212> TYPE: RNA
<213> ORGANISM: Artificial Sequence
<220> FEATURE:
<223> OTHER INFORMATION: oligonucleotide

<400> SEQUENCE: 60
gacccucaaa aacaa                                                    15

<210> SEQ ID NO 61
<211> LENGTH: 15
<212> TYPE: RNA
<213> ORGANISM: Artificial Sequence
<220> FEATURE:
<223> OTHER INFORMATION: oligonucleotide

<400> SEQUENCE: 61
acccucaaaa acaag                                                    15

<210> SEQ ID NO 62
<211> LENGTH: 15
<212> TYPE: RNA
<213> ORGANISM: Artificial Sequence
<220> FEATURE:
<223> OTHER INFORMATION: oligonucleotide

<400> SEQUENCE: 62
cccucaaaaa caagu                                                    15

<210> SEQ ID NO 63
<211> LENGTH: 15
<212> TYPE: RNA
<213> ORGANISM: Artificial Sequence
<220> FEATURE:
<223> OTHER INFORMATION: oligonucleotide

<400> SEQUENCE: 63
ccucaaaaac aaguu                                                    15
```

```
<210> SEQ ID NO 64
<211> LENGTH: 15
<212> TYPE: RNA
<213> ORGANISM: Artificial Sequence
<220> FEATURE:
<223> OTHER INFORMATION: oligonucleotide

<400> SEQUENCE: 64
cucaaaaaca aguuu                                                          15

<210> SEQ ID NO 65
<211> LENGTH: 15
<212> TYPE: RNA
<213> ORGANISM: Artificial Sequence
<220> FEATURE:
<223> OTHER INFORMATION: oligonucleotide

<400> SEQUENCE: 65
ucaaaaacaa guuug                                                          15

<210> SEQ ID NO 66
<211> LENGTH: 15
<212> TYPE: RNA
<213> ORGANISM: Artificial Sequence
<220> FEATURE:
<223> OTHER INFORMATION: oligonucleotide

<400> SEQUENCE: 66
caaaaacaag uuugc                                                          15

<210> SEQ ID NO 67
<211> LENGTH: 15
<212> TYPE: RNA
<213> ORGANISM: Artificial Sequence
<220> FEATURE:
<223> OTHER INFORMATION: oligonucleotide

<400> SEQUENCE: 67
aaaaacaagu uugcc                                                          15

<210> SEQ ID NO 68
<211> LENGTH: 15
<212> TYPE: RNA
<213> ORGANISM: Artificial Sequence
<220> FEATURE:
<223> OTHER INFORMATION: oligonucleotide

<400> SEQUENCE: 68
aaaacaaguu ugccu                                                          15

<210> SEQ ID NO 69
<211> LENGTH: 15
<212> TYPE: RNA
<213> ORGANISM: Artificial Sequence
<220> FEATURE:
<223> OTHER INFORMATION: oligonucleotide

<400> SEQUENCE: 69
aaacaaguuu gccuc                                                          15

<210> SEQ ID NO 70
<211> LENGTH: 88
<212> TYPE: DNA
<213> ORGANISM: Homo sapiens
```

```
<400> SEQUENCE: 70
ccagcgggtg cgggccgagg agcgtgaaca gatcaagacc ctcaacaaca agtttgcctc    60
cttcatcgac aaggtgcggt tcctggag                                       88

<210> SEQ ID NO 71
<211> LENGTH: 88
<212> TYPE: DNA
<213> ORGANISM: Homo sapiens

<400> SEQUENCE: 71
ccagcgggtg cgggccgagg agcgtgaaca gatcaagacc ctcaacaaca agtttgcctc    60
cttcatcgac aaggtgcggt tcctggag                                       88

<210> SEQ ID NO 72
<211> LENGTH: 29
<212> TYPE: RNA
<213> ORGANISM: Artificial Sequence
<220> FEATURE:
<223> OTHER INFORMATION: oligonucleotide

<400> SEQUENCE: 72
cgggugcggg ccgaggagcg ugaacagaa                                      29

<210> SEQ ID NO 73
<211> LENGTH: 29
<212> TYPE: RNA
<213> ORGANISM: Artificial Sequence
<220> FEATURE:
<223> OTHER INFORMATION: oligonucleotide

<400> SEQUENCE: 73
gggugcgggc cgaggagcgu gaacagaac                                      29

<210> SEQ ID NO 74
<211> LENGTH: 29
<212> TYPE: RNA
<213> ORGANISM: Artificial Sequence
<220> FEATURE:
<223> OTHER INFORMATION: oligonucleotide

<400> SEQUENCE: 74
ggugcgggcc gaggagcgug aacagaaca                                      29

<210> SEQ ID NO 75
<211> LENGTH: 29
<212> TYPE: RNA
<213> ORGANISM: Artificial Sequence
<220> FEATURE:
<223> OTHER INFORMATION: oligonucleotide

<400> SEQUENCE: 75
gugcgggccg aggagcguga acagaacaa                                      29

<210> SEQ ID NO 76
<211> LENGTH: 29
<212> TYPE: RNA
<213> ORGANISM: Artificial Sequence
<220> FEATURE:
<223> OTHER INFORMATION: oligonucleotide

<400> SEQUENCE: 76
ugcgggccga ggagcgugaa cagaacaag                                      29
```

<210> SEQ ID NO 77
<211> LENGTH: 29
<212> TYPE: RNA
<213> ORGANISM: Artificial Sequence
<220> FEATURE:
<223> OTHER INFORMATION: oligonucleotide

<400> SEQUENCE: 77
gcgggccgag gagcgugaac agaacaaga                                29

<210> SEQ ID NO 78
<211> LENGTH: 29
<212> TYPE: RNA
<213> ORGANISM: Artificial Sequence
<220> FEATURE:
<223> OTHER INFORMATION: oligonucleotide

<400> SEQUENCE: 78
cgggccgagg agcgugaaca gaacaagac                                29

<210> SEQ ID NO 79
<211> LENGTH: 29
<212> TYPE: RNA
<213> ORGANISM: Artificial Sequence
<220> FEATURE:
<223> OTHER INFORMATION: oligonucleotide

<400> SEQUENCE: 79
gggccgagga gcgugaacag aacaagacc                                29

<210> SEQ ID NO 80
<211> LENGTH: 29
<212> TYPE: RNA
<213> ORGANISM: Artificial Sequence
<220> FEATURE:
<223> OTHER INFORMATION: oligonucleotide

<400> SEQUENCE: 80
ggccgaggag cgugaacaga acaagaccc                                29

<210> SEQ ID NO 81
<211> LENGTH: 29
<212> TYPE: RNA
<213> ORGANISM: Artificial Sequence
<220> FEATURE:
<223> OTHER INFORMATION: oligonucleotide

<400> SEQUENCE: 81
gccgaggagc gugaacagaa caagaccccu                                29

<210> SEQ ID NO 82
<211> LENGTH: 29
<212> TYPE: RNA
<213> ORGANISM: Artificial Sequence
<220> FEATURE:
<223> OTHER INFORMATION: oligonucleotide

<400> SEQUENCE: 82
ccgaggagcg ugaacagaac aagacccuc                                29

<210> SEQ ID NO 83
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 83
cgaggagcgu gaacagaaca agacccuca                              29

<210> SEQ ID NO 84
<211> LENGTH: 29
<212> TYPE: RNA
<213> ORGANISM: Artificial Sequence
<220> FEATURE:
<223> OTHER INFORMATION: oligonucleotide

<400> SEQUENCE: 84
gaggagcgug aacagaacaa gacccucaa                              29

<210> SEQ ID NO 85
<211> LENGTH: 29
<212> TYPE: RNA
<213> ORGANISM: Artificial Sequence
<220> FEATURE:
<223> OTHER INFORMATION: oligonucleotide

<400> SEQUENCE: 85
aggagcguga acagaacaag acccucaac                              29

<210> SEQ ID NO 86
<211> LENGTH: 29
<212> TYPE: RNA
<213> ORGANISM: Artificial Sequence
<220> FEATURE:
<223> OTHER INFORMATION: oligonucleotide

<400> SEQUENCE: 86
ggagcgugaa cagaacaaga cccucaaca                              29

<210> SEQ ID NO 87
<211> LENGTH: 29
<212> TYPE: RNA
<213> ORGANISM: Artificial Sequence
<220> FEATURE:
<223> OTHER INFORMATION: oligonucleotide

<400> SEQUENCE: 87
gagcgugaac agaacaagac ccucaacaa                              29

<210> SEQ ID NO 88
<211> LENGTH: 29
<212> TYPE: RNA
<213> ORGANISM: Artificial Sequence
<220> FEATURE:
<223> OTHER INFORMATION: oligonucleotide

<400> SEQUENCE: 88
agcgugaaca gaacaagacc cucaacaac                              29

<210> SEQ ID NO 89
<211> LENGTH: 29
<212> TYPE: RNA
<213> ORGANISM: Artificial Sequence
<220> FEATURE:
<223> OTHER INFORMATION: oligonucleotide

<400> SEQUENCE: 89
gcgugaacag aacaagaccc ucaacaaca                              29
```

```
<210> SEQ ID NO 90
<211> LENGTH: 29
<212> TYPE: RNA
<213> ORGANISM: Artificial Sequence
<220> FEATURE:
<223> OTHER INFORMATION: oligonucleotide

<400> SEQUENCE: 90
cgugaacaga acaagacccu caacaacaa                                              29

<210> SEQ ID NO 91
<211> LENGTH: 29
<212> TYPE: RNA
<213> ORGANISM: Artificial Sequence
<220> FEATURE:
<223> OTHER INFORMATION: oligonucleotide

<400> SEQUENCE: 91
gugaacagaa caagacccuc aacaacaag                                              29

<210> SEQ ID NO 92
<211> LENGTH: 29
<212> TYPE: RNA
<213> ORGANISM: Artificial Sequence
<220> FEATURE:
<223> OTHER INFORMATION: oligonucleotide

<400> SEQUENCE: 92
ugaacagaac aagacccuca acaacaagu                                              29

<210> SEQ ID NO 93
<211> LENGTH: 29
<212> TYPE: RNA
<213> ORGANISM: Artificial Sequence
<220> FEATURE:
<223> OTHER INFORMATION: oligonucleotide

<400> SEQUENCE: 93
gaacagaaca agacccucaa caacaaguu                                              29

<210> SEQ ID NO 94
<211> LENGTH: 29
<212> TYPE: RNA
<213> ORGANISM: Artificial Sequence
<220> FEATURE:
<223> OTHER INFORMATION: oligonucleotide

<400> SEQUENCE: 94
aacagaacaa gacccucaac aacaaguuu                                              29

<210> SEQ ID NO 95
<211> LENGTH: 29
<212> TYPE: RNA
<213> ORGANISM: Artificial Sequence
<220> FEATURE:
<223> OTHER INFORMATION: oligonucleotide

<400> SEQUENCE: 95
acagaacaag acccucaaca acaaguuug                                              29

<210> SEQ ID NO 96
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 96
cagaacaaga cccucaacaa caaguuugc                                       29

<210> SEQ ID NO 97
<211> LENGTH: 29
<212> TYPE: RNA
<213> ORGANISM: Artificial Sequence
<220> FEATURE:
<223> OTHER INFORMATION: oligonucleotide

<400> SEQUENCE: 97
agaacaagac ccucaacaac aaguuugcc                                       29

<210> SEQ ID NO 98
<211> LENGTH: 29
<212> TYPE: RNA
<213> ORGANISM: Artificial Sequence
<220> FEATURE:
<223> OTHER INFORMATION: oligonucleotide

<400> SEQUENCE: 98
gaacaagacc cucaacaaca aguuugccu                                       29

<210> SEQ ID NO 99
<211> LENGTH: 29
<212> TYPE: RNA
<213> ORGANISM: Artificial Sequence
<220> FEATURE:
<223> OTHER INFORMATION: oligonucleotide

<400> SEQUENCE: 99
aacaagaccc ucaacaacaa guuugccuc                                       29

<210> SEQ ID NO 100
<211> LENGTH: 29
<212> TYPE: RNA
<213> ORGANISM: Artificial Sequence
<220> FEATURE:
<223> OTHER INFORMATION: oligonucleotide

<400> SEQUENCE: 100
acaagacccu caacaacaag uuugccucc                                       29

<210> SEQ ID NO 101
<211> LENGTH: 88
<212> TYPE: DNA
<213> ORGANISM: Homo sapiens

<400> SEQUENCE: 101
ccagcgggtg cgggccgagg agcgtgaaca gatcaagacc ctcaacaaca gtttgcctc      60 cttcatcgac aaggtgcggt tcctggag                                        88

<210> SEQ ID NO 102
<211> LENGTH: 88
<212> TYPE: DNA
<213> ORGANISM: Homo sapiens

<400> SEQUENCE: 102
ccagcgggtg cgggccgagg agcgtgaaca gatcaagacc ttcaacaaca gtttgcctc      60 cttcatcgac aaggtgcggt tcctggag                                        88
```

<210> SEQ ID NO 103
<211> LENGTH: 29
<212> TYPE: RNA
<213> ORGANISM: Artificial Sequence
<220> FEATURE:
<223> OTHER INFORMATION: oligonucleotide

<400> SEQUENCE: 103
ggccgaggag cgugaacaga ucaagaccu                          29

<210> SEQ ID NO 104
<211> LENGTH: 29
<212> TYPE: RNA
<213> ORGANISM: Artificial Sequence
<220> FEATURE:
<223> OTHER INFORMATION: oligonucleotide

<400> SEQUENCE: 104
gccgaggagc gugaacagau caagaccuu                          29

<210> SEQ ID NO 105
<211> LENGTH: 29
<212> TYPE: RNA
<213> ORGANISM: Artificial Sequence
<220> FEATURE:
<223> OTHER INFORMATION: oligonucleotide

<400> SEQUENCE: 105
ccgaggagcg ugaacagauc aagaccuuc                          29

<210> SEQ ID NO 106
<211> LENGTH: 29
<212> TYPE: RNA
<213> ORGANISM: Artificial Sequence
<220> FEATURE:
<223> OTHER INFORMATION: oligonucleotide

<400> SEQUENCE: 106
cgaggagcgu gaacagauca agaccuuca                          29

<210> SEQ ID NO 107
<211> LENGTH: 29
<212> TYPE: RNA
<213> ORGANISM: Artificial Sequence
<220> FEATURE:
<223> OTHER INFORMATION: oligonucleotide

<400> SEQUENCE: 107
gaggagcgug aacagaucaa gaccuucaa                          29

<210> SEQ ID NO 108
<211> LENGTH: 29
<212> TYPE: RNA
<213> ORGANISM: Artificial Sequence
<220> FEATURE:
<223> OTHER INFORMATION: oligonucleotide

<400> SEQUENCE: 108
aggagcguga acagaucaag accuucaac                          29

<210> SEQ ID NO 109
<211> LENGTH: 29
<212> TYPE: RNA
<213> ORGANISM: Artificial Sequence
<220> FEATURE:
<223> OTHER INFORMATION: oligonucleotide

<400> SEQUENCE: 109
ggagcgugaa cagaucaaga ccuucaaca                                      29

<210> SEQ ID NO 110
<211> LENGTH: 29
<212> TYPE: RNA
<213> ORGANISM: Artificial Sequence
<220> FEATURE:
<223> OTHER INFORMATION: oligonucleotide

<400> SEQUENCE: 110
gagcgugaac agaucaagac cuucaacaa                                      29

<210> SEQ ID NO 111
<211> LENGTH: 29
<212> TYPE: RNA
<213> ORGANISM: Artificial Sequence
<220> FEATURE:
<223> OTHER INFORMATION: oligonucleotide

<400> SEQUENCE: 111
agcgugaaca gaucaagacc uucaacaac                                      29

<210> SEQ ID NO 112
<211> LENGTH: 29
<212> TYPE: RNA
<213> ORGANISM: Artificial Sequence
<220> FEATURE:
<223> OTHER INFORMATION: oligonucleotide

<400> SEQUENCE: 112
gcgugaacag aucaagaccu ucaacaaca                                      29

<210> SEQ ID NO 113
<211> LENGTH: 29
<212> TYPE: RNA
<213> ORGANISM: Artificial Sequence
<220> FEATURE:
<223> OTHER INFORMATION: oligonucleotide

<400> SEQUENCE: 113
cgugaacaga ucaagaccuu caacaacaa                                      29

<210> SEQ ID NO 114
<211> LENGTH: 29
<212> TYPE: RNA
<213> ORGANISM: Artificial Sequence
<220> FEATURE:
<223> OTHER INFORMATION: oligonucleotide

<400> SEQUENCE: 114
gugaacagau caagaccuuc aacaacaag                                      29

<210> SEQ ID NO 115
<211> LENGTH: 29
<212> TYPE: RNA
<213> ORGANISM: Artificial Sequence
<220> FEATURE:
<223> OTHER INFORMATION: oligonucleotide

<400> SEQUENCE: 115
ugaacagauc aagaccuuca acaacaagu                                      29

<210> SEQ ID NO 116
<211> LENGTH: 29
<212> TYPE: RNA
<213> ORGANISM: Artificial Sequence
<220> FEATURE:
<223> OTHER INFORMATION: oligonucleotide

<400> SEQUENCE: 116
gaacagauca agaccuucaa caacaaguu                                      29

<210> SEQ ID NO 117
<211> LENGTH: 29
<212> TYPE: RNA
<213> ORGANISM: Artificial Sequence
<220> FEATURE:
<223> OTHER INFORMATION: oligonucleotide

<400> SEQUENCE: 117
aacagaucaa gaccuucaac aacaaguuu                                      29

<210> SEQ ID NO 118
<211> LENGTH: 29
<212> TYPE: RNA
<213> ORGANISM: Artificial Sequence
<220> FEATURE:
<223> OTHER INFORMATION: oligonucleotide

<400> SEQUENCE: 118
acagaucaag accuucaaca acaaguuug                                      29

<210> SEQ ID NO 119
<211> LENGTH: 29
<212> TYPE: RNA
<213> ORGANISM: Artificial Sequence
<220> FEATURE:
<223> OTHER INFORMATION: oligonucleotide

<400> SEQUENCE: 119
cagaucaaga ccuucaacaa caaguuugc                                      29

<210> SEQ ID NO 120
<211> LENGTH: 29
<212> TYPE: RNA
<213> ORGANISM: Artificial Sequence
<220> FEATURE:
<223> OTHER INFORMATION: oligonucleotide

<400> SEQUENCE: 120
agaucaagac cuucaacaac aaguuugcc                                      29

<210> SEQ ID NO 121
<211> LENGTH: 29
<212> TYPE: RNA
<213> ORGANISM: Artificial Sequence
<220> FEATURE:
<223> OTHER INFORMATION: oligonucleotide

<400> SEQUENCE: 121
gaucaagacc uucaacaaca aguuugccu                                      29

<210> SEQ ID NO 122
<211> LENGTH: 29
<212> TYPE: RNA
<213> ORGANISM: Artificial Sequence
<220> FEATURE:
<223> OTHER INFORMATION: oligonucleotide

<400> SEQUENCE: 122
aucaagaccu ucaacaacaa guuugccuc					29

<210> SEQ ID NO 123
<211> LENGTH: 29
<212> TYPE: RNA
<213> ORGANISM: Artificial Sequence
<220> FEATURE:
<223> OTHER INFORMATION: oligonucleotide

<400> SEQUENCE: 123
ucaagaccuu caacaacaag uuugccucc					29

<210> SEQ ID NO 124
<211> LENGTH: 29
<212> TYPE: RNA
<213> ORGANISM: Artificial Sequence
<220> FEATURE:
<223> OTHER INFORMATION: oligonucleotide

<400> SEQUENCE: 124
caagaccuuc aacaacaagu uugccuccu					29

<210> SEQ ID NO 125
<211> LENGTH: 29
<212> TYPE: RNA
<213> ORGANISM: Artificial Sequence
<220> FEATURE:
<223> OTHER INFORMATION: oligonucleotide

<400> SEQUENCE: 125
aagaccuuca acaacaaguu ugccuccuu					29

<210> SEQ ID NO 126
<211> LENGTH: 29
<212> TYPE: RNA
<213> ORGANISM: Artificial Sequence
<220> FEATURE:
<223> OTHER INFORMATION: oligonucleotide

<400> SEQUENCE: 126
agaccuucaa caacaaguuu gccuccuuc					29

<210> SEQ ID NO 127
<211> LENGTH: 29
<212> TYPE: RNA
<213> ORGANISM: Artificial Sequence
<220> FEATURE:
<223> OTHER INFORMATION: oligonucleotide

<400> SEQUENCE: 127
gaccuucaac aacaaguuug ccuccuuca					29

<210> SEQ ID NO 128
<211> LENGTH: 29
<212> TYPE: RNA
<213> ORGANISM: Artificial Sequence
<220> FEATURE:
<223> OTHER INFORMATION: oligonucleotide

<400> SEQUENCE: 128
accuucaaca acaaguuugc cuccuucau					29

```
<210> SEQ ID NO 129
<211> LENGTH: 29
<212> TYPE: RNA
<213> ORGANISM: Artificial Sequence
<220> FEATURE:
<223> OTHER INFORMATION: oligonucleotide

<400> SEQUENCE: 129
ccuucaacaa caaguuugcc uccuucauc                                              29

<210> SEQ ID NO 130
<211> LENGTH: 29
<212> TYPE: RNA
<213> ORGANISM: Artificial Sequence
<220> FEATURE:
<223> OTHER INFORMATION: oligonucleotide

<400> SEQUENCE: 130
cuucaacaac aaguuugccu ccuucaucg                                              29

<210> SEQ ID NO 131
<211> LENGTH: 29
<212> TYPE: RNA
<213> ORGANISM: Artificial Sequence
<220> FEATURE:
<223> OTHER INFORMATION: oligonucleotide

<400> SEQUENCE: 131
uucaacaaca aguuugccuc cuucaucga                                              29

<210> SEQ ID NO 132
<211> LENGTH: 88
<212> TYPE: DNA
<213> ORGANISM: Homo sapiens

<400> SEQUENCE: 132
ccagcgggtg cgggccgagg agcgtgaaca gatcaagacc ctcaacaaca agtttgcctc            60
cttcatcgac aaggtgcggt tcctggag                                               88

<210> SEQ ID NO 133
<211> LENGTH: 88
<212> TYPE: DNA
<213> ORGANISM: Homo sapiens

<400> SEQUENCE: 133
ccagcgggtg cgggccgagg agcgtgaaca gatcaagacc ctcagcaaca agtttgcctc            60
cttcatcgac aaggtgcggt tcctggag                                               88

<210> SEQ ID NO 134
<211> LENGTH: 29
<212> TYPE: RNA
<213> ORGANISM: Artificial Sequence
<220> FEATURE:
<223> OTHER INFORMATION: oligonucleotide

<400> SEQUENCE: 134
gaggagcgug aacagaucaa gacccucag                                              29

<210> SEQ ID NO 135
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 135
aggagcguga acagaucaag acccucagc                                29

<210> SEQ ID NO 136
<211> LENGTH: 29
<212> TYPE: RNA
<213> ORGANISM: Artificial Sequence
<220> FEATURE:
<223> OTHER INFORMATION: oligonucleotide

<400> SEQUENCE: 136
ggagcgugaa cagaucaaga cccucagca                                29

<210> SEQ ID NO 137
<211> LENGTH: 29
<212> TYPE: RNA
<213> ORGANISM: Artificial Sequence
<220> FEATURE:
<223> OTHER INFORMATION: oligonucleotide

<400> SEQUENCE: 137
gagcgugaac agaucaagac ccucagcaa                                29

<210> SEQ ID NO 138
<211> LENGTH: 29
<212> TYPE: RNA
<213> ORGANISM: Artificial Sequence
<220> FEATURE:
<223> OTHER INFORMATION: oligonucleotide

<400> SEQUENCE: 138
agcgugaaca gaucaagacc cucagcaac                                29

<210> SEQ ID NO 139
<211> LENGTH: 29
<212> TYPE: RNA
<213> ORGANISM: Artificial Sequence
<220> FEATURE:
<223> OTHER INFORMATION: oligonucleotide

<400> SEQUENCE: 139
gcgugaacag aucaagaccc ucagcaaca                                29

<210> SEQ ID NO 140
<211> LENGTH: 29
<212> TYPE: RNA
<213> ORGANISM: Artificial Sequence
<220> FEATURE:
<223> OTHER INFORMATION: oligonucleotide

<400> SEQUENCE: 140
cgugaacaga ucaagacccu cagcaacaa                                29

<210> SEQ ID NO 141
<211> LENGTH: 29
<212> TYPE: RNA
<213> ORGANISM: Artificial Sequence
<220> FEATURE:
<223> OTHER INFORMATION: oligonucleotide

<400> SEQUENCE: 141
gugaacagau caagacccuc agcaacaag                                29
```

<210> SEQ ID NO 142
<211> LENGTH: 29
<212> TYPE: RNA
<213> ORGANISM: Artificial Sequence
<220> FEATURE:
<223> OTHER INFORMATION: oligonucleotide

<400> SEQUENCE: 142
ugaacagauc aagacccuca gcaacaagu                                            29

<210> SEQ ID NO 143
<211> LENGTH: 29
<212> TYPE: RNA
<213> ORGANISM: Artificial Sequence
<220> FEATURE:
<223> OTHER INFORMATION: oligonucleotide

<400> SEQUENCE: 143
gaacagauca agacccucag caacaaguu                                            29

<210> SEQ ID NO 144
<211> LENGTH: 29
<212> TYPE: RNA
<213> ORGANISM: Artificial Sequence
<220> FEATURE:
<223> OTHER INFORMATION: oligonucleotide

<400> SEQUENCE: 144
aacagaucaa gacccucagc aacaaguuu                                            29

<210> SEQ ID NO 145
<211> LENGTH: 29
<212> TYPE: RNA
<213> ORGANISM: Artificial Sequence
<220> FEATURE:
<223> OTHER INFORMATION: oligonucleotide

<400> SEQUENCE: 145
acagaucaag acccucagca acaaguuug                                            29

<210> SEQ ID NO 146
<211> LENGTH: 29
<212> TYPE: RNA
<213> ORGANISM: Artificial Sequence
<220> FEATURE:
<223> OTHER INFORMATION: oligonucleotide

<400> SEQUENCE: 146
cagaucaaga cccucagcaa caaguuugc                                            29

<210> SEQ ID NO 147
<211> LENGTH: 29
<212> TYPE: RNA
<213> ORGANISM: Artificial Sequence
<220> FEATURE:
<223> OTHER INFORMATION: oligonucleotide

<400> SEQUENCE: 147
agaucaagac ccucagcaac aaguuugcc                                            29

<210> SEQ ID NO 148
<211> LENGTH: 29
<212> TYPE: RNA
<213> ORGANISM: Artificial Sequence
<220> FEATURE:
<223> OTHER INFORMATION: oligonucleotide

<400> SEQUENCE: 148
gaucaagacc cucagcaaca aguuugccu					29

<210> SEQ ID NO 149
<211> LENGTH: 29
<212> TYPE: RNA
<213> ORGANISM: Artificial Sequence
<220> FEATURE:
<223> OTHER INFORMATION: oligonucleotide

<400> SEQUENCE: 149
aucaagaccc ucagcaacaa guuugccuc					29

<210> SEQ ID NO 150
<211> LENGTH: 29
<212> TYPE: RNA
<213> ORGANISM: Artificial Sequence
<220> FEATURE:
<223> OTHER INFORMATION: oligonucleotide

<400> SEQUENCE: 150
ucaagacccu cagcaacaag uuugccucc					29

<210> SEQ ID NO 151
<211> LENGTH: 29
<212> TYPE: RNA
<213> ORGANISM: Artificial Sequence
<220> FEATURE:
<223> OTHER INFORMATION: oligonucleotide

<400> SEQUENCE: 151
caagacccuc agcaacaagu uugccuccu					29

<210> SEQ ID NO 152
<211> LENGTH: 29
<212> TYPE: RNA
<213> ORGANISM: Artificial Sequence
<220> FEATURE:
<223> OTHER INFORMATION: oligonucleotide

<400> SEQUENCE: 152
aagacccuca gcaacaaguu ugccuccuu					29

<210> SEQ ID NO 153
<211> LENGTH: 29
<212> TYPE: RNA
<213> ORGANISM: Artificial Sequence
<220> FEATURE:
<223> OTHER INFORMATION: oligonucleotide

<400> SEQUENCE: 153
agacccucag caacaaguuu gccuccuuc					29

<210> SEQ ID NO 154
<211> LENGTH: 29
<212> TYPE: RNA
<213> ORGANISM: Artificial Sequence
<220> FEATURE:
<223> OTHER INFORMATION: oligonucleotide

<400> SEQUENCE: 154
gacccucagc aacaaguuug ccuccuuca					29

<210> SEQ ID NO 155
<211> LENGTH: 29
<212> TYPE: RNA
<213> ORGANISM: Artificial Sequence
<220> FEATURE:
<223> OTHER INFORMATION: oligonucleotide

<400> SEQUENCE: 155
acccucagca acaaguuugc cuccuucau                              29

<210> SEQ ID NO 156
<211> LENGTH: 29
<212> TYPE: RNA
<213> ORGANISM: Artificial Sequence
<220> FEATURE:
<223> OTHER INFORMATION: oligonucleotide

<400> SEQUENCE: 156
cccucagcaa caaguuugcc uccuucauc                              29

<210> SEQ ID NO 157
<211> LENGTH: 29
<212> TYPE: RNA
<213> ORGANISM: Artificial Sequence
<220> FEATURE:
<223> OTHER INFORMATION: oligonucleotide

<400> SEQUENCE: 157
ccucagcaac aaguuugccu ccuucaucg                              29

<210> SEQ ID NO 158
<211> LENGTH: 29
<212> TYPE: RNA
<213> ORGANISM: Artificial Sequence
<220> FEATURE:
<223> OTHER INFORMATION: oligonucleotide

<400> SEQUENCE: 158
cucagcaaca aguuugccuc cuucaucga                              29

<210> SEQ ID NO 159
<211> LENGTH: 29
<212> TYPE: RNA
<213> ORGANISM: Artificial Sequence
<220> FEATURE:
<223> OTHER INFORMATION: oligonucleotide

<400> SEQUENCE: 159
ucagcaacaa guuugccucc uucaucgac                              29

<210> SEQ ID NO 160
<211> LENGTH: 29
<212> TYPE: RNA
<213> ORGANISM: Artificial Sequence
<220> FEATURE:
<223> OTHER INFORMATION: oligonucleotide

<400> SEQUENCE: 160
cagcaacaag uuugccuccu ucaucgaca                              29

<210> SEQ ID NO 161
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 161
agcaacaagu ugccuccuu caucgacaa                                          29

<210> SEQ ID NO 162
<211> LENGTH: 29
<212> TYPE: RNA
<213> ORGANISM: Artificial Sequence
<220> FEATURE:
<223> OTHER INFORMATION: oligonucleotide

<400> SEQUENCE: 162
gcaacaaguu ugccuccuuc aucgacaag                                         29

<210> SEQ ID NO 163
<211> LENGTH: 66
<212> TYPE: DNA
<213> ORGANISM: Homo sapiens

<400> SEQUENCE: 163
cgtgaacaga tcaagaccct caacaacaag tttgcctcct tcatcgacaa ggtgcggttc       60
ctggag                                                                  66

<210> SEQ ID NO 164
<211> LENGTH: 66
<212> TYPE: DNA
<213> ORGANISM: Homo sapiens

<400> SEQUENCE: 164
cgtgaacaga tcaagaccct caacaacaag tttgccccct tcatcgacaa ggtgcggttc       60
ctggag                                                                  66

<210> SEQ ID NO 165
<211> LENGTH: 29
<212> TYPE: RNA
<213> ORGANISM: Artificial Sequence
<220> FEATURE:
<223> OTHER INFORMATION: oligonucleotide

<400> SEQUENCE: 165
gaucaagacc cucaacaaca aguuugccc                                         29

<210> SEQ ID NO 166
<211> LENGTH: 29
<212> TYPE: RNA
<213> ORGANISM: Artificial Sequence
<220> FEATURE:
<223> OTHER INFORMATION: oligonucleotide

<400> SEQUENCE: 166
aucaagaccc ucaacaacaa guuugcccc                                         29

<210> SEQ ID NO 167
<211> LENGTH: 29
<212> TYPE: RNA
<213> ORGANISM: Artificial Sequence
<220> FEATURE:
<223> OTHER INFORMATION: oligonucleotide

<400> SEQUENCE: 167
ucaagacccu caacaacaag uuugccccc                                         29
```

<210> SEQ ID NO 168
<211> LENGTH: 29
<212> TYPE: RNA
<213> ORGANISM: Artificial Sequence
<220> FEATURE:
<223> OTHER INFORMATION: oligonucleotide

<400> SEQUENCE: 168
caagacccuc aacaacaagu uugccccu                                    29

<210> SEQ ID NO 169
<211> LENGTH: 29
<212> TYPE: RNA
<213> ORGANISM: Artificial Sequence
<220> FEATURE:
<223> OTHER INFORMATION: oligonucleotide

<400> SEQUENCE: 169
aagacccuca acaacaaguu ugccccuu                                    29

<210> SEQ ID NO 170
<211> LENGTH: 29
<212> TYPE: RNA
<213> ORGANISM: Artificial Sequence
<220> FEATURE:
<223> OTHER INFORMATION: oligonucleotide

<400> SEQUENCE: 170
agacccucaa caacaaguuu gccccuuc                                    29

<210> SEQ ID NO 171
<211> LENGTH: 29
<212> TYPE: RNA
<213> ORGANISM: Artificial Sequence
<220> FEATURE:
<223> OTHER INFORMATION: oligonucleotide

<400> SEQUENCE: 171
gacccucaac aacaaguuug ccccuuca                                    29

<210> SEQ ID NO 172
<211> LENGTH: 29
<212> TYPE: RNA
<213> ORGANISM: Artificial Sequence
<220> FEATURE:
<223> OTHER INFORMATION: oligonucleotide

<400> SEQUENCE: 172
acccucaaca acaaguuugc ccccuucau                                   29

<210> SEQ ID NO 173
<211> LENGTH: 29
<212> TYPE: RNA
<213> ORGANISM: Artificial Sequence
<220> FEATURE:
<223> OTHER INFORMATION: oligonucleotide

<400> SEQUENCE: 173
cccucaacaa caaguuugcc cccuucauc                                   29

<210> SEQ ID NO 174
<211> LENGTH: 29
<212> TYPE: RNA
<213> ORGANISM: Artificial Sequence
<220> FEATURE:
<223> OTHER INFORMATION: oligonucleotide

<400> SEQUENCE: 174
ccucaacaac aaguuugccc ccuucaucg            29

<210> SEQ ID NO 175
<211> LENGTH: 29
<212> TYPE: RNA
<213> ORGANISM: Artificial Sequence
<220> FEATURE:
<223> OTHER INFORMATION: oligonucleotide

<400> SEQUENCE: 175
cucaacaaca aguuugcccc cuucaucga            29

<210> SEQ ID NO 176
<211> LENGTH: 29
<212> TYPE: RNA
<213> ORGANISM: Artificial Sequence
<220> FEATURE:
<223> OTHER INFORMATION: oligonucleotide

<400> SEQUENCE: 176
ucaacaacaa guuugccccc uucaucgac            29

<210> SEQ ID NO 177
<211> LENGTH: 29
<212> TYPE: RNA
<213> ORGANISM: Artificial Sequence
<220> FEATURE:
<223> OTHER INFORMATION: oligonucleotide

<400> SEQUENCE: 177
caacaacaag uuugcccccu ucaucgaca            29

<210> SEQ ID NO 178
<211> LENGTH: 29
<212> TYPE: RNA
<213> ORGANISM: Artificial Sequence
<220> FEATURE:
<223> OTHER INFORMATION: oligonucleotide

<400> SEQUENCE: 178
aacaacaagu uugcccccuu caucgacaa            29

<210> SEQ ID NO 179
<211> LENGTH: 29
<212> TYPE: RNA
<213> ORGANISM: Artificial Sequence
<220> FEATURE:
<223> OTHER INFORMATION: oligonucleotide

<400> SEQUENCE: 179
acaacaaguu ugcccccuuc aucgacaag            29

<210> SEQ ID NO 180
<211> LENGTH: 29
<212> TYPE: RNA
<213> ORGANISM: Artificial Sequence
<220> FEATURE:
<223> OTHER INFORMATION: oligonucleotide

<400> SEQUENCE: 180
caacaaguuu gcccccuuca ucgacaagg            29

```
<210> SEQ ID NO 181
<211> LENGTH: 29
<212> TYPE: RNA
<213> ORGANISM: Artificial Sequence
<220> FEATURE:
<223> OTHER INFORMATION: oligonucleotide

<400> SEQUENCE: 181
aacaaguuug cccccuucau cgacaaggu                                    29

<210> SEQ ID NO 182
<211> LENGTH: 29
<212> TYPE: RNA
<213> ORGANISM: Artificial Sequence
<220> FEATURE:
<223> OTHER INFORMATION: oligonucleotide

<400> SEQUENCE: 182
acaaguuugc ccccuucauc gacaaggug                                    29

<210> SEQ ID NO 183
<211> LENGTH: 29
<212> TYPE: RNA
<213> ORGANISM: Artificial Sequence
<220> FEATURE:
<223> OTHER INFORMATION: oligonucleotide

<400> SEQUENCE: 183
caaguuugcc cccuucaucg acaaggugc                                    29

<210> SEQ ID NO 184
<211> LENGTH: 29
<212> TYPE: RNA
<213> ORGANISM: Artificial Sequence
<220> FEATURE:
<223> OTHER INFORMATION: oligonucleotide

<400> SEQUENCE: 184
aaguuugccc ccuucaucga caaggugcg                                    29

<210> SEQ ID NO 185
<211> LENGTH: 29
<212> TYPE: RNA
<213> ORGANISM: Artificial Sequence
<220> FEATURE:
<223> OTHER INFORMATION: oligonucleotide

<400> SEQUENCE: 185
aguuugcccc cuucaucgac aaggugcgg                                    29

<210> SEQ ID NO 186
<211> LENGTH: 29
<212> TYPE: RNA
<213> ORGANISM: Artificial Sequence
<220> FEATURE:
<223> OTHER INFORMATION: oligonucleotide

<400> SEQUENCE: 186
guuugccccc uucaucgaca aggugcggu                                    29

<210> SEQ ID NO 187
<211> LENGTH: 29
<212> TYPE: RNA
<213> ORGANISM: Artificial Sequence
<220> FEATURE:
<223> OTHER INFORMATION: oligonucleotide
```

<400> SEQUENCE: 187 uuugccccu ucaucgacaa ggugcgguu                                29

<210> SEQ ID NO 188
<211> LENGTH: 29
<212> TYPE: RNA
<213> ORGANISM: Artificial Sequence
<220> FEATURE:
<223> OTHER INFORMATION: oligonucleotide

<400> SEQUENCE: 188
uugcccccuu caucgacaag gugcgguuc                                29

<210> SEQ ID NO 189
<211> LENGTH: 29
<212> TYPE: RNA
<213> ORGANISM: Artificial Sequence
<220> FEATURE:
<223> OTHER INFORMATION: oligonucleotide

<400> SEQUENCE: 189
ugcccccuuc aucgacaagg ugcgguucc                                29

<210> SEQ ID NO 190
<211> LENGTH: 29
<212> TYPE: RNA
<213> ORGANISM: Artificial Sequence
<220> FEATURE:
<223> OTHER INFORMATION: oligonucleotide

<400> SEQUENCE: 190
gcccccuuca ucgacaaggu gcgguuccu                                29

<210> SEQ ID NO 191
<211> LENGTH: 29
<212> TYPE: RNA
<213> ORGANISM: Artificial Sequence
<220> FEATURE:
<223> OTHER INFORMATION: oligonucleotide

<400> SEQUENCE: 191
cccccuucau cgacaaggug cgguuccug                                29

<210> SEQ ID NO 192
<211> LENGTH: 29
<212> TYPE: RNA
<213> ORGANISM: Artificial Sequence
<220> FEATURE:
<223> OTHER INFORMATION: oligonucleotide

<400> SEQUENCE: 192
ccccuucauc gacaaggugc gguuccugg                                29

<210> SEQ ID NO 193
<211> LENGTH: 29
<212> TYPE: RNA
<213> ORGANISM: Artificial Sequence
<220> FEATURE:
<223> OTHER INFORMATION: oligonucleotide

<400> SEQUENCE: 193
cccuucaucg acaaggugcg guuccugga                                29

<210> SEQ ID NO 194
<211> LENGTH: 88
<212> TYPE: DNA
<213> ORGANISM: Homo sapiens

<400> SEQUENCE: 194
ccagcgggtg cgggccgagg agcgtgaaca gatcaagacc ctcaacaaca agtttgcctc    60
cttcatcgac aaggtgcggt tcctggag                                      88

<210> SEQ ID NO 195
<211> LENGTH: 85
<212> TYPE: DNA
<213> ORGANISM: Homo sapiens

<400> SEQUENCE: 195
ccagcgggtg cgggccgagg agcgtgaaca gatcaagacc ctcaacaagt ttgcctcctt    60
catcgacaag gtgcggttcc tggag                                         85

<210> SEQ ID NO 196
<211> LENGTH: 29
<212> TYPE: RNA
<213> ORGANISM: Artificial Sequence
<220> FEATURE:
<223> OTHER INFORMATION: oligonucleotide

<400> SEQUENCE: 196
cgaggagcgu gaacagauca agacccuca                                     29

<210> SEQ ID NO 197
<211> LENGTH: 29
<212> TYPE: RNA
<213> ORGANISM: Artificial Sequence
<220> FEATURE:
<223> OTHER INFORMATION: oligonucleotide

<400> SEQUENCE: 197
gaggagcgug aacagaucaa gacccucaa                                     29

<210> SEQ ID NO 198
<211> LENGTH: 29
<212> TYPE: RNA
<213> ORGANISM: Artificial Sequence
<220> FEATURE:
<223> OTHER INFORMATION: oligonucleotide

<400> SEQUENCE: 198
aggagcguga acagaucaag acccucaac                                     29

<210> SEQ ID NO 199
<211> LENGTH: 29
<212> TYPE: RNA
<213> ORGANISM: Artificial Sequence
<220> FEATURE:
<223> OTHER INFORMATION: oligonucleotide

<400> SEQUENCE: 199
ggagcgugaa cagaucaaga cccucaaca                                     29

<210> SEQ ID NO 200
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 200
gagcgugaac agaucaagac ccucaacaa                              29

<210> SEQ ID NO 201
<211> LENGTH: 29
<212> TYPE: RNA
<213> ORGANISM: Artificial Sequence
<220> FEATURE:
<223> OTHER INFORMATION: oligonucleotide

<400> SEQUENCE: 201
agcgugaaca gaucaagacc cucaacaag                              29

<210> SEQ ID NO 202
<211> LENGTH: 29
<212> TYPE: RNA
<213> ORGANISM: Artificial Sequence
<220> FEATURE:
<223> OTHER INFORMATION: oligonucleotide

<400> SEQUENCE: 202
gcgugaacag aucaagaccc ucaacaagu                              29

<210> SEQ ID NO 203
<211> LENGTH: 29
<212> TYPE: RNA
<213> ORGANISM: Artificial Sequence
<220> FEATURE:
<223> OTHER INFORMATION: oligonucleotide

<400> SEQUENCE: 203
cgugaacaga ucaagacccu caacaaguu                              29

<210> SEQ ID NO 204
<211> LENGTH: 29
<212> TYPE: RNA
<213> ORGANISM: Artificial Sequence
<220> FEATURE:
<223> OTHER INFORMATION: oligonucleotide

<400> SEQUENCE: 204
gugaacagau caagacccuc aacaaguuu                              29

<210> SEQ ID NO 205
<211> LENGTH: 29
<212> TYPE: RNA
<213> ORGANISM: Artificial Sequence
<220> FEATURE:
<223> OTHER INFORMATION: oligonucleotide

<400> SEQUENCE: 205
ugaacagauc aagacccuca acaaguuug                              29

<210> SEQ ID NO 206
<211> LENGTH: 29
<212> TYPE: RNA
<213> ORGANISM: Artificial Sequence
<220> FEATURE:
<223> OTHER INFORMATION: oligonucleotide

<400> SEQUENCE: 206
gaacagauca agacccucaa caaguugc                               29
```

```
<210> SEQ ID NO 207
<211> LENGTH: 29
<212> TYPE: RNA
<213> ORGANISM: Artificial Sequence
<220> FEATURE:
<223> OTHER INFORMATION: oligonucleotide

<400> SEQUENCE: 207
aacagaucaa gacccucaac aaguuugcc                                           29

<210> SEQ ID NO 208
<211> LENGTH: 29
<212> TYPE: RNA
<213> ORGANISM: Artificial Sequence
<220> FEATURE:
<223> OTHER INFORMATION: oligonucleotide

<400> SEQUENCE: 208
acagaucaag acccucaaca aguuugccu                                           29

<210> SEQ ID NO 209
<211> LENGTH: 29
<212> TYPE: RNA
<213> ORGANISM: Artificial Sequence
<220> FEATURE:
<223> OTHER INFORMATION: oligonucleotide

<400> SEQUENCE: 209
cagaucaaga cccucaacaa guuugccuc                                           29

<210> SEQ ID NO 210
<211> LENGTH: 29
<212> TYPE: RNA
<213> ORGANISM: Artificial Sequence
<220> FEATURE:
<223> OTHER INFORMATION: oligonucleotide

<400> SEQUENCE: 210
agaucaagac ccucaacaag uuugccucc                                           29

<210> SEQ ID NO 211
<211> LENGTH: 29
<212> TYPE: RNA
<213> ORGANISM: Artificial Sequence
<220> FEATURE:
<223> OTHER INFORMATION: oligonucleotide

<400> SEQUENCE: 211
gaucaagacc cucaacaagu uugccuccu                                           29

<210> SEQ ID NO 212
<211> LENGTH: 29
<212> TYPE: RNA
<213> ORGANISM: Artificial Sequence
<220> FEATURE:
<223> OTHER INFORMATION: oligonucleotide

<400> SEQUENCE: 212
aucaagaccc ucaacaaguu ugccuccuu                                           29

<210> SEQ ID NO 213
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 213
ucaagacccu caacaaguuu gccuccuuc                                    29

<210> SEQ ID NO 214
<211> LENGTH: 29
<212> TYPE: RNA
<213> ORGANISM: Artificial Sequence
<220> FEATURE:
<223> OTHER INFORMATION: oligonucleotide

<400> SEQUENCE: 214
caagacccuc aacaaguuug ccuccuuca                                    29

<210> SEQ ID NO 215
<211> LENGTH: 29
<212> TYPE: RNA
<213> ORGANISM: Artificial Sequence
<220> FEATURE:
<223> OTHER INFORMATION: oligonucleotide

<400> SEQUENCE: 215
aagacccuca acaaguuugc cuccuucau                                    29

<210> SEQ ID NO 216
<211> LENGTH: 29
<212> TYPE: RNA
<213> ORGANISM: Artificial Sequence
<220> FEATURE:
<223> OTHER INFORMATION: oligonucleotide

<400> SEQUENCE: 216
agacccucaa caaguuugcc uccuucauc                                    29

<210> SEQ ID NO 217
<211> LENGTH: 29
<212> TYPE: RNA
<213> ORGANISM: Artificial Sequence
<220> FEATURE:
<223> OTHER INFORMATION: oligonucleotide

<400> SEQUENCE: 217
gacccucaac aaguuugccu ccuucaucg                                    29

<210> SEQ ID NO 218
<211> LENGTH: 29
<212> TYPE: RNA
<213> ORGANISM: Artificial Sequence
<220> FEATURE:
<223> OTHER INFORMATION: oligonucleotide

<400> SEQUENCE: 218
acccucaaca aguuugccuc cuucaucga                                    29

<210> SEQ ID NO 219
<211> LENGTH: 29
<212> TYPE: RNA
<213> ORGANISM: Artificial Sequence
<220> FEATURE:
<223> OTHER INFORMATION: oligonucleotide

<400> SEQUENCE: 219
cccucaacaa guuugccucc uucaucgac                                    29
```

<210> SEQ ID NO 220
<211> LENGTH: 29
<212> TYPE: RNA
<213> ORGANISM: Artificial Sequence
<220> FEATURE:
<223> OTHER INFORMATION: oligonucleotide

<400> SEQUENCE: 220
ccucaacaag uuugccuccu ucaucgaca                                    29

<210> SEQ ID NO 221
<211> LENGTH: 29
<212> TYPE: RNA
<213> ORGANISM: Artificial Sequence
<220> FEATURE:
<223> OTHER INFORMATION: oligonucleotide

<400> SEQUENCE: 221
cucaacaagu uugccuccuu caucgacaa                                    29

<210> SEQ ID NO 222
<211> LENGTH: 29
<212> TYPE: RNA
<213> ORGANISM: Artificial Sequence
<220> FEATURE:
<223> OTHER INFORMATION: oligonucleotide

<400> SEQUENCE: 222
ucaacaaguu ugccuccuuc aucgacaag                                    29

<210> SEQ ID NO 223
<211> LENGTH: 29
<212> TYPE: RNA
<213> ORGANISM: Artificial Sequence
<220> FEATURE:
<223> OTHER INFORMATION: oligonucleotide

<400> SEQUENCE: 223
caacaaguuu gccuccuuca ucgacaagg                                    29

<210> SEQ ID NO 224
<211> LENGTH: 77
<212> TYPE: DNA
<213> ORGANISM: Homo sapiens

<400> SEQUENCE: 224
gggccgagga gcgtgaacag atcaagaccc tcaacaacaa gtttgcctcc ttcatcgaca    60
aggtgcggtt cctggag                                                 77

<210> SEQ ID NO 225
<211> LENGTH: 77
<212> TYPE: DNA
<213> ORGANISM: Homo sapiens

<400> SEQUENCE: 225
gggccgagga gcgtgaacag atcaagaccc tcaacaacaa gtctgcctcc ttcatcgaca    60
aggtgcggtt cctggag                                                 77

<210> SEQ ID NO 226
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 226
gaacagauca agacccucaa caacaaguc                                29

<210> SEQ ID NO 227
<211> LENGTH: 29
<212> TYPE: RNA
<213> ORGANISM: Artificial Sequence
<220> FEATURE:
<223> OTHER INFORMATION: oligonucleotide

<400> SEQUENCE: 227
aacagaucaa gacccucaac aacaagucu                                29

<210> SEQ ID NO 228
<211> LENGTH: 29
<212> TYPE: RNA
<213> ORGANISM: Artificial Sequence
<220> FEATURE:
<223> OTHER INFORMATION: oligonucleotide

<400> SEQUENCE: 228
acagaucaag acccucaaca acaagucug                                29

<210> SEQ ID NO 229
<211> LENGTH: 29
<212> TYPE: RNA
<213> ORGANISM: Artificial Sequence
<220> FEATURE:
<223> OTHER INFORMATION: oligonucleotide

<400> SEQUENCE: 229
cagaucaaga cccucaacaa caagucugc                                29

<210> SEQ ID NO 230
<211> LENGTH: 29
<212> TYPE: RNA
<213> ORGANISM: Artificial Sequence
<220> FEATURE:
<223> OTHER INFORMATION: oligonucleotide

<400> SEQUENCE: 230
agaucaagac ccucaacaac aagucugcc                                29

<210> SEQ ID NO 231
<211> LENGTH: 29
<212> TYPE: RNA
<213> ORGANISM: Artificial Sequence
<220> FEATURE:
<223> OTHER INFORMATION: oligonucleotide

<400> SEQUENCE: 231
gaucaagacc cucaacaaca agucugccu                                29

<210> SEQ ID NO 232
<211> LENGTH: 29
<212> TYPE: RNA
<213> ORGANISM: Artificial Sequence
<220> FEATURE:
<223> OTHER INFORMATION: oligonucleotide

<400> SEQUENCE: 232
aucaagaccc ucaacaacaa gucugccuc                                29
```

```
<210> SEQ ID NO 233
<211> LENGTH: 29
<212> TYPE: RNA
<213> ORGANISM: Artificial Sequence
<220> FEATURE:
<223> OTHER INFORMATION: oligonucleotide

<400> SEQUENCE: 233
ucaagacccu caacaacaag ucugccucc                                         29

<210> SEQ ID NO 234
<211> LENGTH: 29
<212> TYPE: RNA
<213> ORGANISM: Artificial Sequence
<220> FEATURE:
<223> OTHER INFORMATION: oligonucleotide

<400> SEQUENCE: 234
caagacccuc aacaacaagu cugccuccu                                         29

<210> SEQ ID NO 235
<211> LENGTH: 29
<212> TYPE: RNA
<213> ORGANISM: Artificial Sequence
<220> FEATURE:
<223> OTHER INFORMATION: oligonucleotide

<400> SEQUENCE: 235
aagacccuca acaacaaguc ugccuccuu                                         29

<210> SEQ ID NO 236
<211> LENGTH: 29
<212> TYPE: RNA
<213> ORGANISM: Artificial Sequence
<220> FEATURE:
<223> OTHER INFORMATION: oligonucleotide

<400> SEQUENCE: 236
agacccucaa caacaagucu gccuccuuc                                         29

<210> SEQ ID NO 237
<211> LENGTH: 29
<212> TYPE: RNA
<213> ORGANISM: Artificial Sequence
<220> FEATURE:
<223> OTHER INFORMATION: oligonucleotide

<400> SEQUENCE: 237
gacccucaac aacaagucug ccuccuuca                                         29

<210> SEQ ID NO 238
<211> LENGTH: 29
<212> TYPE: RNA
<213> ORGANISM: Artificial Sequence
<220> FEATURE:
<223> OTHER INFORMATION: oligonucleotide

<400> SEQUENCE: 238
acccucaaca acaagucugc cuccuucau                                         29

<210> SEQ ID NO 239
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 239
acccucaaca acaagucugc cuccuucau                                29

<210> SEQ ID NO 240
<211> LENGTH: 29
<212> TYPE: RNA
<213> ORGANISM: Artificial Sequence
<220> FEATURE:
<223> OTHER INFORMATION: oligonucleotide

<400> SEQUENCE: 240
ccucaacaac aagucugccu ccuucaucg                                29

<210> SEQ ID NO 241
<211> LENGTH: 29
<212> TYPE: RNA
<213> ORGANISM: Artificial Sequence
<220> FEATURE:
<223> OTHER INFORMATION: oligonucleotide

<400> SEQUENCE: 241
cucaacaaca agucugccuc cuucaucga                                29

<210> SEQ ID NO 242
<211> LENGTH: 29
<212> TYPE: RNA
<213> ORGANISM: Artificial Sequence
<220> FEATURE:
<223> OTHER INFORMATION: oligonucleotide

<400> SEQUENCE: 242
ucaacaacaa gucugccucc uucaucgac                                29

<210> SEQ ID NO 243
<211> LENGTH: 29
<212> TYPE: RNA
<213> ORGANISM: Artificial Sequence
<220> FEATURE:
<223> OTHER INFORMATION: oligonucleotide

<400> SEQUENCE: 243
ucaacaacaa gucugccucc uucaucgac                                29

<210> SEQ ID NO 244
<211> LENGTH: 29
<212> TYPE: RNA
<213> ORGANISM: Artificial Sequence
<220> FEATURE:
<223> OTHER INFORMATION: oligonucleotide

<400> SEQUENCE: 244
aacaacaagu cugccuccuu caucgacaa                                29

<210> SEQ ID NO 245
<211> LENGTH: 29
<212> TYPE: RNA
<213> ORGANISM: Artificial Sequence
<220> FEATURE:
<223> OTHER INFORMATION: oligonucleotide

<400> SEQUENCE: 245
acaacaaguc ugccuccuuc aucgacaag                                29
```

```
<210> SEQ ID NO 246
<211> LENGTH: 29
<212> TYPE: RNA
<213> ORGANISM: Artificial Sequence
<220> FEATURE:
<223> OTHER INFORMATION: oligonucleotide

<400> SEQUENCE: 246
caacaagucu gccuccuuca ucgacaagg                                   29

<210> SEQ ID NO 247
<211> LENGTH: 29
<212> TYPE: RNA
<213> ORGANISM: Artificial Sequence
<220> FEATURE:
<223> OTHER INFORMATION: oligonucleotide

<400> SEQUENCE: 247
aacaagucug ccuccuucau cgacaaggu                                   29

<210> SEQ ID NO 248
<211> LENGTH: 29
<212> TYPE: RNA
<213> ORGANISM: Artificial Sequence
<220> FEATURE:
<223> OTHER INFORMATION: oligonucleotide

<400> SEQUENCE: 248
acaagucugc cuccuucauc gacaaggug                                   29

<210> SEQ ID NO 249
<211> LENGTH: 29
<212> TYPE: RNA
<213> ORGANISM: Artificial Sequence
<220> FEATURE:
<223> OTHER INFORMATION: oligonucleotide

<400> SEQUENCE: 249
caagucugcc uccuucaucg acaaggugc                                   29

<210> SEQ ID NO 250
<211> LENGTH: 29
<212> TYPE: RNA
<213> ORGANISM: Artificial Sequence
<220> FEATURE:
<223> OTHER INFORMATION: oligonucleotide

<400> SEQUENCE: 250
aagucugccu ccuucaucga caaggugcg                                   29

<210> SEQ ID NO 251
<211> LENGTH: 29
<212> TYPE: RNA
<213> ORGANISM: Artificial Sequence
<220> FEATURE:
<223> OTHER INFORMATION: oligonucleotide

<400> SEQUENCE: 251
agucugccuc cuucaucgac aaggugcgg                                   29

<210> SEQ ID NO 252
<211> LENGTH: 29
<212> TYPE: RNA
<213> ORGANISM: Artificial Sequence
<220> FEATURE:
<223> OTHER INFORMATION: oligonucleotide
```

<400> SEQUENCE: 252
gucugccucc uucaucgaca aggugcggu            29

<210> SEQ ID NO 253
<211> LENGTH: 29
<212> TYPE: RNA
<213> ORGANISM: Artificial Sequence
<220> FEATURE:
<223> OTHER INFORMATION: oligonucleotide

<400> SEQUENCE: 253
ucugccuccu ucaucgacaa ggugcgguu            29

<210> SEQ ID NO 254
<211> LENGTH: 29
<212> TYPE: RNA
<213> ORGANISM: Artificial Sequence
<220> FEATURE:
<223> OTHER INFORMATION: oligonucleotide

<400> SEQUENCE: 254
cugccuccuu caucgacaag gugcgguuc            29

<210> SEQ ID NO 255
<211> LENGTH: 90
<212> TYPE: DNA
<213> ORGANISM: Homo sapiens

<400> SEQUENCE: 255
gaatgtcaag ctggccctgg acgtggagat cgccacctac cgcaagctgc tggagggtga   60
ggagtgcagg ctgaatggcg aaggcgttgg                                   90

<210> SEQ ID NO 256
<211> LENGTH: 90
<212> TYPE: DNA
<213> ORGANISM: Homo sapiens

<400> SEQUENCE: 256
gaatgtcaag ctggccctgg acgtggagaa cgccacctac cgcaagctgc tggagggtga   60
ggagtgcagg ctgaatggcg aaggcgttgg                                   90

<210> SEQ ID NO 257
<211> LENGTH: 29
<212> TYPE: RNA
<213> ORGANISM: Artificial Sequence
<220> FEATURE:
<223> OTHER INFORMATION: oligonucleotide

<400> SEQUENCE: 257
aaugucaagc uggcccugga cguggagaa            29

<210> SEQ ID NO 258
<211> LENGTH: 29
<212> TYPE: RNA
<213> ORGANISM: Artificial Sequence
<220> FEATURE:
<223> OTHER INFORMATION: oligonucleotide

<400> SEQUENCE: 258
augucaagcu ggcccuggac guggagaac            29

```
<210> SEQ ID NO 259
<211> LENGTH: 29
<212> TYPE: RNA
<213> ORGANISM: Artificial Sequence
<220> FEATURE:
<223> OTHER INFORMATION: oligonucleotide

<400> SEQUENCE: 259
ugucaagcug gcccuggacg uggagaacg                                     29

<210> SEQ ID NO 260
<211> LENGTH: 29
<212> TYPE: RNA
<213> ORGANISM: Artificial Sequence
<220> FEATURE:
<223> OTHER INFORMATION: oligonucleotide

<400> SEQUENCE: 260
gucaagcugg cccuggacgu ggagaacgc                                     29

<210> SEQ ID NO 261
<211> LENGTH: 29
<212> TYPE: RNA
<213> ORGANISM: Artificial Sequence
<220> FEATURE:
<223> OTHER INFORMATION: oligonucleotide

<400> SEQUENCE: 261
ucaagcuggc ccuggacgug gagaacgcc                                     29

<210> SEQ ID NO 262
<211> LENGTH: 29
<212> TYPE: RNA
<213> ORGANISM: Artificial Sequence
<220> FEATURE:
<223> OTHER INFORMATION: oligonucleotide

<400> SEQUENCE: 262
caagcuggcc cuggacgugg agaacgcca                                     29

<210> SEQ ID NO 263
<211> LENGTH: 29
<212> TYPE: RNA
<213> ORGANISM: Artificial Sequence
<220> FEATURE:
<223> OTHER INFORMATION: oligonucleotide

<400> SEQUENCE: 263
aagcuggccc uggacgugga gaacgccac                                     29

<210> SEQ ID NO 264
<211> LENGTH: 29
<212> TYPE: RNA
<213> ORGANISM: Artificial Sequence
<220> FEATURE:
<223> OTHER INFORMATION: oligonucleotide

<400> SEQUENCE: 264
agcuggcccu ggacguggag aacgccacc                                     29

<210> SEQ ID NO 265

<400> SEQUENCE: 265

000
```

```
<210> SEQ ID NO 266
<211> LENGTH: 29
<212> TYPE: RNA
<213> ORGANISM: Artificial Sequence
<220> FEATURE:
<223> OTHER INFORMATION: oligonucleotide

<400> SEQUENCE: 266
cuggcccugg acguggagaa cgccaccua                                    29

<210> SEQ ID NO 267
<211> LENGTH: 29
<212> TYPE: RNA
<213> ORGANISM: Artificial Sequence
<220> FEATURE:
<223> OTHER INFORMATION: oligonucleotide

<400> SEQUENCE: 267
uggcccugga cguggagaac gccaccuac                                    29

<210> SEQ ID NO 268
<211> LENGTH: 29
<212> TYPE: RNA
<213> ORGANISM: Artificial Sequence
<220> FEATURE:
<223> OTHER INFORMATION: oligonucleotide

<400> SEQUENCE: 268
ggcccuggac guggagaacg ccaccuacc                                    29

<210> SEQ ID NO 269
<211> LENGTH: 29
<212> TYPE: RNA
<213> ORGANISM: Artificial Sequence
<220> FEATURE:
<223> OTHER INFORMATION: oligonucleotide

<400> SEQUENCE: 269
gcccuggacg uggagaacgc caccuaccg                                    29

<210> SEQ ID NO 270
<211> LENGTH: 29
<212> TYPE: RNA
<213> ORGANISM: Artificial Sequence
<220> FEATURE:
<223> OTHER INFORMATION: oligonucleotide

<400> SEQUENCE: 270
cccuggacgu ggagaacgcc accuaccgc                                    29

<210> SEQ ID NO 271
<211> LENGTH: 29
<212> TYPE: RNA
<213> ORGANISM: Artificial Sequence
<220> FEATURE:
<223> OTHER INFORMATION: oligonucleotide

<400> SEQUENCE: 271
ccuggacgug gagaacgcca ccuaccgca                                    29

<210> SEQ ID NO 272
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 272
cuggacgugg agaacgccac cuaccgcaa                                         29

<210> SEQ ID NO 273
<211> LENGTH: 29
<212> TYPE: RNA
<213> ORGANISM: Artificial Sequence
<220> FEATURE:
<223> OTHER INFORMATION: oligonucleotide

<400> SEQUENCE: 273
uggacgugga gaacgccacc uaccgcaag                                         29

<210> SEQ ID NO 274
<211> LENGTH: 29
<212> TYPE: RNA
<213> ORGANISM: Artificial Sequence
<220> FEATURE:
<223> OTHER INFORMATION: oligonucleotide

<400> SEQUENCE: 274
ggacguggag aacgccaccu accgcaagc                                         29

<210> SEQ ID NO 275
<211> LENGTH: 29
<212> TYPE: RNA
<213> ORGANISM: Artificial Sequence
<220> FEATURE:
<223> OTHER INFORMATION: oligonucleotide

<400> SEQUENCE: 275
gacguggaga acgccaccua ccgcaagcu                                         29

<210> SEQ ID NO 276
<211> LENGTH: 29
<212> TYPE: RNA
<213> ORGANISM: Artificial Sequence
<220> FEATURE:
<223> OTHER INFORMATION: oligonucleotide

<400> SEQUENCE: 276
acguggagaa cgccaccuac cgcaagcug                                         29

<210> SEQ ID NO 277
<211> LENGTH: 29
<212> TYPE: RNA
<213> ORGANISM: Artificial Sequence
<220> FEATURE:
<223> OTHER INFORMATION: oligonucleotide

<400> SEQUENCE: 277
cguggagaac gccaccuacc gcaagcugc                                         29

<210> SEQ ID NO 278
<211> LENGTH: 29
<212> TYPE: RNA
<213> ORGANISM: Artificial Sequence
<220> FEATURE:
<223> OTHER INFORMATION: oligonucleotide

<400> SEQUENCE: 278
guggagaacg ccaccuaccg caagcugcu                                         29
```

```
<210> SEQ ID NO 279
<211> LENGTH: 29
<212> TYPE: RNA
<213> ORGANISM: Artificial Sequence
<220> FEATURE:
<223> OTHER INFORMATION: oligonucleotide

<400> SEQUENCE: 279
uggagaacgc caccuaccgc aagcugcug                                              29

<210> SEQ ID NO 280
<211> LENGTH: 29
<212> TYPE: RNA
<213> ORGANISM: Artificial Sequence
<220> FEATURE:
<223> OTHER INFORMATION: oligonucleotide

<400> SEQUENCE: 280
ggagaacgcc accuaccgca agcugcugg                                              29

<210> SEQ ID NO 281
<211> LENGTH: 29
<212> TYPE: RNA
<213> ORGANISM: Artificial Sequence
<220> FEATURE:
<223> OTHER INFORMATION: oligonucleotide

<400> SEQUENCE: 281
gagaacgcca ccuaccgcaa gcugcugga                                              29

<210> SEQ ID NO 282
<211> LENGTH: 29
<212> TYPE: RNA
<213> ORGANISM: Artificial Sequence
<220> FEATURE:
<223> OTHER INFORMATION: oligonucleotide

<400> SEQUENCE: 282
agaacgccac cuaccgcaag cugcuggag                                              29

<210> SEQ ID NO 283
<211> LENGTH: 29
<212> TYPE: RNA
<213> ORGANISM: Artificial Sequence
<220> FEATURE:
<223> OTHER INFORMATION: oligonucleotide

<400> SEQUENCE: 283
gaacgccacc uaccgcaagc ugcuggagg                                              29

<210> SEQ ID NO 284
<211> LENGTH: 29
<212> TYPE: RNA
<213> ORGANISM: Artificial Sequence
<220> FEATURE:
<223> OTHER INFORMATION: oligonucleotide

<400> SEQUENCE: 284
aacgccaccu accgcaagcu gcuggaggg                                              29

<210> SEQ ID NO 285
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 285
acgccaccua ccgcaagcug cuggagggu                                29

<210> SEQ ID NO 286
<211> LENGTH: 90
<212> TYPE: DNA
<213> ORGANISM: Homo sapiens

<400> SEQUENCE: 286
gaatgtcaag ctggccctgg acgtggagat cgccacctac cgcaagctgc tggagggtga    60
ggagtgcagg ctgaatggcg aaggcgttgg                                     90

<210> SEQ ID NO 287
<211> LENGTH: 90
<212> TYPE: DNA
<213> ORGANISM: Homo sapiens

<400> SEQUENCE: 287
gaatgtcaag ctggccctgg acgtggagat cgccacctac cgcaagccgc tggagggtga    60
ggagtgcagg ctgaatggcg aaggcgttgg                                     90

<210> SEQ ID NO 288
<211> LENGTH: 29
<212> TYPE: RNA
<213> ORGANISM: Artificial Sequence
<220> FEATURE:
<223> OTHER INFORMATION: oligonucleotide

<400> SEQUENCE: 288
gacguggaga ucgccaccua ccgcaagcc                                29

<210> SEQ ID NO 289
<211> LENGTH: 29
<212> TYPE: RNA
<213> ORGANISM: Artificial Sequence
<220> FEATURE:
<223> OTHER INFORMATION: oligonucleotide

<400> SEQUENCE: 289
acguggagau cgccaccuac cgcaagccg                                29

<210> SEQ ID NO 290
<211> LENGTH: 29
<212> TYPE: RNA
<213> ORGANISM: Artificial Sequence
<220> FEATURE:
<223> OTHER INFORMATION: oligonucleotide

<400> SEQUENCE: 290
cguggagauc gccaccuacc gcaagccgc                                29

<210> SEQ ID NO 291
<211> LENGTH: 29
<212> TYPE: RNA
<213> ORGANISM: Artificial Sequence
<220> FEATURE:
<223> OTHER INFORMATION: oligonucleotide

<400> SEQUENCE: 291
guggagaucg ccaccuaccg caagccgcu                                29
```

<210> SEQ ID NO 292
<211> LENGTH: 29
<212> TYPE: RNA
<213> ORGANISM: Artificial Sequence
<220> FEATURE:
<223> OTHER INFORMATION: oligonucleotide

<400> SEQUENCE: 292
uggagaucgc caccuaccgc aagccgcug                              29

<210> SEQ ID NO 293
<211> LENGTH: 29
<212> TYPE: RNA
<213> ORGANISM: Artificial Sequence
<220> FEATURE:
<223> OTHER INFORMATION: oligonucleotide

<400> SEQUENCE: 293
ggagaucgcc accuaccgca agccgcugg                              29

<210> SEQ ID NO 294
<211> LENGTH: 29
<212> TYPE: RNA
<213> ORGANISM: Artificial Sequence
<220> FEATURE:
<223> OTHER INFORMATION: oligonucleotide

<400> SEQUENCE: 294
gagaucgcca ccuaccgcaa gccgcugga                              29

<210> SEQ ID NO 295
<211> LENGTH: 29
<212> TYPE: RNA
<213> ORGANISM: Artificial Sequence
<220> FEATURE:
<223> OTHER INFORMATION: oligonucleotide

<400> SEQUENCE: 295
agaucgccac cuaccgcaag ccgcuggag                              29

<210> SEQ ID NO 296
<211> LENGTH: 29
<212> TYPE: RNA
<213> ORGANISM: Artificial Sequence
<220> FEATURE:
<223> OTHER INFORMATION: oligonucleotide

<400> SEQUENCE: 296
gaucgccacc uaccgcaagc cgcuggagg                              29

<210> SEQ ID NO 297
<211> LENGTH: 29
<212> TYPE: RNA
<213> ORGANISM: Artificial Sequence
<220> FEATURE:
<223> OTHER INFORMATION: oligonucleotide

<400> SEQUENCE: 297
aucgccaccu accgcaagcc gcuggaggg                              29

<210> SEQ ID NO 298
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 298
ucgccaccua ccgcaagccg cuggagggu                                    29

<210> SEQ ID NO 299
<211> LENGTH: 29
<212> TYPE: RNA
<213> ORGANISM: Artificial Sequence
<220> FEATURE:
<223> OTHER INFORMATION: oligonucleotide

<400> SEQUENCE: 299
cgccaccuac cgcaagccgc uggagggug                                    29

<210> SEQ ID NO 300
<211> LENGTH: 29
<212> TYPE: RNA
<213> ORGANISM: Artificial Sequence
<220> FEATURE:
<223> OTHER INFORMATION: oligonucleotide

<400> SEQUENCE: 300
gccaccuacc gcaagccgcu ggaggguga                                    29

<210> SEQ ID NO 301
<211> LENGTH: 29
<212> TYPE: RNA
<213> ORGANISM: Artificial Sequence
<220> FEATURE:
<223> OTHER INFORMATION: oligonucleotide

<400> SEQUENCE: 301
ccaccuaccg caagccgcug gagggugag                                    29

<210> SEQ ID NO 302
<211> LENGTH: 29
<212> TYPE: RNA
<213> ORGANISM: Artificial Sequence
<220> FEATURE:
<223> OTHER INFORMATION: oligonucleotide

<400> SEQUENCE: 302
caccuaccgc aagccgcugg agggugagg                                    29

<210> SEQ ID NO 303
<211> LENGTH: 29
<212> TYPE: RNA
<213> ORGANISM: Artificial Sequence
<220> FEATURE:
<223> OTHER INFORMATION: oligonucleotide

<400> SEQUENCE: 303
accuaccgca agccgcugga gggugagga                                    29

<210> SEQ ID NO 304
<211> LENGTH: 29
<212> TYPE: RNA
<213> ORGANISM: Artificial Sequence
<220> FEATURE:
<223> OTHER INFORMATION: oligonucleotide

<400> SEQUENCE: 304
ccuaccgcaa gccgcuggag ggugaggag                                    29
```

```
<210> SEQ ID NO 305
<211> LENGTH: 29
<212> TYPE: RNA
<213> ORGANISM: Artificial Sequence
<220> FEATURE:
<223> OTHER INFORMATION: oligonucleotide

<400> SEQUENCE: 305
cuaccgcaag ccgcuggagg gugaggagu                                29

<210> SEQ ID NO 306
<211> LENGTH: 29
<212> TYPE: RNA
<213> ORGANISM: Artificial Sequence
<220> FEATURE:
<223> OTHER INFORMATION: oligonucleotide

<400> SEQUENCE: 306
uaccgcaagc cgcuggaggg ugaggagug                                29

<210> SEQ ID NO 307
<211> LENGTH: 29
<212> TYPE: RNA
<213> ORGANISM: Artificial Sequence
<220> FEATURE:
<223> OTHER INFORMATION: oligonucleotide

<400> SEQUENCE: 307
accgcaagcc gcuggagggu gaggagugc                                29

<210> SEQ ID NO 308
<211> LENGTH: 29
<212> TYPE: RNA
<213> ORGANISM: Artificial Sequence
<220> FEATURE:
<223> OTHER INFORMATION: oligonucleotide

<400> SEQUENCE: 308
ccgcaagccg cuggagggug aggagugca                                29

<210> SEQ ID NO 309
<211> LENGTH: 29
<212> TYPE: RNA
<213> ORGANISM: Artificial Sequence
<220> FEATURE:
<223> OTHER INFORMATION: oligonucleotide

<400> SEQUENCE: 309
cgcaagccgc uggaggguga ggagugcag                                29

<210> SEQ ID NO 310
<211> LENGTH: 29
<212> TYPE: RNA
<213> ORGANISM: Artificial Sequence
<220> FEATURE:
<223> OTHER INFORMATION: oligonucleotide

<400> SEQUENCE: 310
gcaagccgcu ggagggugag gagugcagg                                29

<210> SEQ ID NO 311
<211> LENGTH: 29
<212> TYPE: RNA
<213> ORGANISM: Artificial Sequence
<220> FEATURE:
<223> OTHER INFORMATION: oligonucleotide
```

-continued

```
<400> SEQUENCE: 311
caagccgcug gagggugagg agugcaggc                                          29

<210> SEQ ID NO 312
<211> LENGTH: 29
<212> TYPE: RNA
<213> ORGANISM: Artificial Sequence
<220> FEATURE:
<223> OTHER INFORMATION: oligonucleotide

<400> SEQUENCE: 312
aagccgcugg agggugagga gugcaggcu                                          29

<210> SEQ ID NO 313
<211> LENGTH: 29
<212> TYPE: RNA
<213> ORGANISM: Artificial Sequence
<220> FEATURE:
<223> OTHER INFORMATION: oligonucleotide

<400> SEQUENCE: 313
agccgcugga gggugaggag ugcaggcug                                          29

<210> SEQ ID NO 314
<211> LENGTH: 29
<212> TYPE: RNA
<213> ORGANISM: Artificial Sequence
<220> FEATURE:
<223> OTHER INFORMATION: oligonucleotide

<400> SEQUENCE: 314
gccgcuggag ggugaggagu gcaggcuga                                          29

<210> SEQ ID NO 315
<211> LENGTH: 29
<212> TYPE: RNA
<213> ORGANISM: Artificial Sequence
<220> FEATURE:
<223> OTHER INFORMATION: oligonucleotide

<400> SEQUENCE: 315
ccgcuggagg gugaggagug caggcugaa                                          29

<210> SEQ ID NO 316
<211> LENGTH: 29
<212> TYPE: RNA
<213> ORGANISM: Artificial Sequence
<220> FEATURE:
<223> OTHER INFORMATION: oligonucleotide

<400> SEQUENCE: 316
cgcuggaggg ugaggagugc aggcugaau                                          29

<210> SEQ ID NO 317
<211> LENGTH: 90
<212> TYPE: DNA
<213> ORGANISM: Homo sapiens

<400> SEQUENCE: 317
gaatgtcaag ctggccctgg acgtggagat cgccacctac cgcaagctgc tggagggtga       60
ggagtgcagg ctgaatggcg aaggcgttgg                                         90
```

```
<210> SEQ ID NO 318
<211> LENGTH: 90
<212> TYPE: DNA
<213> ORGANISM: Homo sapiens

<400> SEQUENCE: 318
gaatgtcaag ctggccctgg acgtggagat cgccacctac cgcaagctgc cggagggtga      60
ggagtgcagg ctgaatggcg aaggcgttgg                                       90

<210> SEQ ID NO 319
<211> LENGTH: 29
<212> TYPE: RNA
<213> ORGANISM: Artificial Sequence
<220> FEATURE:
<223> OTHER INFORMATION: oligonucleotide

<400> SEQUENCE: 319
guggagaucg ccaccuaccg caagcugcc                                        29

<210> SEQ ID NO 320
<211> LENGTH: 29
<212> TYPE: RNA
<213> ORGANISM: Artificial Sequence
<220> FEATURE:
<223> OTHER INFORMATION: oligonucleotide

<400> SEQUENCE: 320
uggagaucgc caccuaccgc aagcugccg                                        29

<210> SEQ ID NO 321
<211> LENGTH: 29
<212> TYPE: RNA
<213> ORGANISM: Artificial Sequence
<220> FEATURE:
<223> OTHER INFORMATION: oligonucleotide

<400> SEQUENCE: 321
ggagaucgcc accuaccgca agcugccgg                                        29

<210> SEQ ID NO 322
<211> LENGTH: 29
<212> TYPE: RNA
<213> ORGANISM: Artificial Sequence
<220> FEATURE:
<223> OTHER INFORMATION: oligonucleotide

<400> SEQUENCE: 322
gagaucgcca ccuaccgcaa gcugccgga                                        29

<210> SEQ ID NO 323
<211> LENGTH: 29
<212> TYPE: RNA
<213> ORGANISM: Artificial Sequence
<220> FEATURE:
<223> OTHER INFORMATION: oligonucleotide

<400> SEQUENCE: 323
agaucgccac cuaccgcaag cugccggag                                        29

<210> SEQ ID NO 324
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 324
gaucgccacc uaccgcaagc ugccggagg                                29

<210> SEQ ID NO 325
<211> LENGTH: 29
<212> TYPE: RNA
<213> ORGANISM: Artificial Sequence
<220> FEATURE:
<223> OTHER INFORMATION: oligonucleotide

<400> SEQUENCE: 325
aucgccaccu accgcaagcu gccggaggg                                29

<210> SEQ ID NO 326
<211> LENGTH: 29
<212> TYPE: RNA
<213> ORGANISM: Artificial Sequence
<220> FEATURE:
<223> OTHER INFORMATION: oligonucleotide

<400> SEQUENCE: 326
ucgccaccua ccgcaagcug ccggagggu                                29

<210> SEQ ID NO 327
<211> LENGTH: 29
<212> TYPE: RNA
<213> ORGANISM: Artificial Sequence
<220> FEATURE:
<223> OTHER INFORMATION: oligonucleotide

<400> SEQUENCE: 327
cgccaccuac cgcaagcugc cggagggug                                29

<210> SEQ ID NO 328
<211> LENGTH: 29
<212> TYPE: RNA
<213> ORGANISM: Artificial Sequence
<220> FEATURE:
<223> OTHER INFORMATION: oligonucleotide

<400> SEQUENCE: 328
gccaccuacc gcaagcugcc ggaggguga                                29

<210> SEQ ID NO 329
<211> LENGTH: 29
<212> TYPE: RNA
<213> ORGANISM: Artificial Sequence
<220> FEATURE:
<223> OTHER INFORMATION: oligonucleotide

<400> SEQUENCE: 329
ccaccuaccg caagcugccg gagggugag                                29

<210> SEQ ID NO 330
<211> LENGTH: 29
<212> TYPE: RNA
<213> ORGANISM: Artificial Sequence
<220> FEATURE:
<223> OTHER INFORMATION: oligonucleotide

<400> SEQUENCE: 330
caccuaccgc aagcugccgg agggugagg                                29
```

```
<210> SEQ ID NO 331
<211> LENGTH: 29
<212> TYPE: RNA
<213> ORGANISM: Artificial Sequence
<220> FEATURE:
<223> OTHER INFORMATION: oligonucleotide

<400> SEQUENCE: 331
accuaccgca agcugccgga gggugagga                                              29

<210> SEQ ID NO 332
<211> LENGTH: 29
<212> TYPE: RNA
<213> ORGANISM: Artificial Sequence
<220> FEATURE:
<223> OTHER INFORMATION: oligonucleotide

<400> SEQUENCE: 332
ccuaccgcaa gcugccggag ggugaggag                                              29

<210> SEQ ID NO 333
<211> LENGTH: 29
<212> TYPE: RNA
<213> ORGANISM: Artificial Sequence
<220> FEATURE:
<223> OTHER INFORMATION: oligonucleotide

<400> SEQUENCE: 333
cuaccgcaag cugccggagg gugaggagu                                              29

<210> SEQ ID NO 334
<211> LENGTH: 29
<212> TYPE: RNA
<213> ORGANISM: Artificial Sequence
<220> FEATURE:
<223> OTHER INFORMATION: oligonucleotide

<400> SEQUENCE: 334
uaccgcaagc ugccggaggg ugaggagug                                              29

<210> SEQ ID NO 335
<211> LENGTH: 29
<212> TYPE: RNA
<213> ORGANISM: Artificial Sequence
<220> FEATURE:
<223> OTHER INFORMATION: oligonucleotide

<400> SEQUENCE: 335
accgcaagcu gccggagggu gaggagugc                                              29

<210> SEQ ID NO 336
<211> LENGTH: 29
<212> TYPE: RNA
<213> ORGANISM: Artificial Sequence
<220> FEATURE:
<223> OTHER INFORMATION: oligonucleotide

<400> SEQUENCE: 336
ccgcaagcug ccggagggug aggagugca                                              29

<210> SEQ ID NO 337
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 337
cgcaagcugc cggaggguga ggagugcag                              29

<210> SEQ ID NO 338
<211> LENGTH: 29
<212> TYPE: RNA
<213> ORGANISM: Artificial Sequence
<220> FEATURE:
<223> OTHER INFORMATION: oligonucleotide

<400> SEQUENCE: 338
gcaagcugcc ggagggugag gagugcagg                              29

<210> SEQ ID NO 339
<211> LENGTH: 29
<212> TYPE: RNA
<213> ORGANISM: Artificial Sequence
<220> FEATURE:
<223> OTHER INFORMATION: oligonucleotide

<400> SEQUENCE: 339
caagcugccg gagggugagg agugcaggc                              29

<210> SEQ ID NO 340
<211> LENGTH: 29
<212> TYPE: RNA
<213> ORGANISM: Artificial Sequence
<220> FEATURE:
<223> OTHER INFORMATION: oligonucleotide

<400> SEQUENCE: 340
aagcugccgg agggugagga gugcaggcu                              29

<210> SEQ ID NO 341
<211> LENGTH: 29
<212> TYPE: RNA
<213> ORGANISM: Artificial Sequence
<220> FEATURE:
<223> OTHER INFORMATION: oligonucleotide

<400> SEQUENCE: 341
agcugccgga gggugaggag ugcaggcug                              29

<210> SEQ ID NO 342
<211> LENGTH: 29
<212> TYPE: RNA
<213> ORGANISM: Artificial Sequence
<220> FEATURE:
<223> OTHER INFORMATION: oligonucleotide

<400> SEQUENCE: 342
gcugccggag ggugaggagu gcaggcuga                              29

<210> SEQ ID NO 343
<211> LENGTH: 29
<212> TYPE: RNA
<213> ORGANISM: Artificial Sequence
<220> FEATURE:
<223> OTHER INFORMATION: oligonucleotide

<400> SEQUENCE: 343
cugccggagg gugaggagug caggcugaa                              29
```

```
<210> SEQ ID NO 344
<211> LENGTH: 29
<212> TYPE: RNA
<213> ORGANISM: Artificial Sequence
<220> FEATURE:
<223> OTHER INFORMATION: oligonucleotide

<400> SEQUENCE: 344
ugccggaggg ugaggagugc aggcugaau                                       29

<210> SEQ ID NO 345
<211> LENGTH: 29
<212> TYPE: RNA
<213> ORGANISM: Artificial Sequence
<220> FEATURE:
<223> OTHER INFORMATION: oligonucleotide

<400> SEQUENCE: 345 gccgagggu gaggagugca ggcugaaug                                        29

<210> SEQ ID NO 346
<211> LENGTH: 29
<212> TYPE: RNA
<213> ORGANISM: Artificial Sequence
<220> FEATURE:
<223> OTHER INFORMATION: oligonucleotide

<400> SEQUENCE: 346
ccggagggug aggagugcag gcugaaugg                                       29

<210> SEQ ID NO 347
<211> LENGTH: 29
<212> TYPE: RNA
<213> ORGANISM: Artificial Sequence
<220> FEATURE:
<223> OTHER INFORMATION: oligonucleotide

<400> SEQUENCE: 347
cggaggguga ggagugcagg cugaauggc                                       29

<210> SEQ ID NO 348
<211> LENGTH: 90
<212> TYPE: DNA
<213> ORGANISM: Homo sapiens

<400> SEQUENCE: 348
ctggccctgg atgtggagat cgccacctac cgcaagctgc tggagggcga ggagtgcagg     60
ctgaatggcg aaggcgttgg acaagtcaac                                      90

<210> SEQ ID NO 349
<211> LENGTH: 90
<212> TYPE: DNA
<213> ORGANISM: Homo sapiens

<400> SEQUENCE: 349 ctggcccctgg atgtggagat cgccacctac cgcaagctgc tggagggcaa ggagtgcagg    60
ctgaatggcg aaggcgttgg acaagtcaac                                      90

<210> SEQ ID NO 350
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 350
cgccaccuac cgcaagcugc uggagggca                                    29

<210> SEQ ID NO 351
<211> LENGTH: 29
<212> TYPE: RNA
<213> ORGANISM: Artificial Sequence
<220> FEATURE:
<223> OTHER INFORMATION: oligonucleotide

<400> SEQUENCE: 351
gccaccuacc gcaagcugcu ggagggcaa                                    29

<210> SEQ ID NO 352
<211> LENGTH: 29
<212> TYPE: RNA
<213> ORGANISM: Artificial Sequence
<220> FEATURE:
<223> OTHER INFORMATION: oligonucleotide

<400> SEQUENCE: 352
ccaccuaccg caagcugcug gagggcaag                                    29

<210> SEQ ID NO 353
<211> LENGTH: 29
<212> TYPE: RNA
<213> ORGANISM: Artificial Sequence
<220> FEATURE:
<223> OTHER INFORMATION: oligonucleotide

<400> SEQUENCE: 353
caccuaccgc aagcugcugg agggcaagg                                    29

<210> SEQ ID NO 354
<211> LENGTH: 29
<212> TYPE: RNA
<213> ORGANISM: Artificial Sequence
<220> FEATURE:
<223> OTHER INFORMATION: oligonucleotide

<400> SEQUENCE: 354
accuaccgca agcugcugga gggcaagga                                    29

<210> SEQ ID NO 355
<211> LENGTH: 29
<212> TYPE: RNA
<213> ORGANISM: Artificial Sequence
<220> FEATURE:
<223> OTHER INFORMATION: oligonucleotide

<400> SEQUENCE: 355
ccuaccgcaa gcugcuggag ggcaaggag                                    29

<210> SEQ ID NO 356
<211> LENGTH: 29
<212> TYPE: RNA
<213> ORGANISM: Artificial Sequence
<220> FEATURE:
<223> OTHER INFORMATION: oligonucleotide

<400> SEQUENCE: 356
cuaccgcaag cugcuggagg gcaaggagu                                    29
```

```
<210> SEQ ID NO 357
<211> LENGTH: 29
<212> TYPE: RNA
<213> ORGANISM: Artificial Sequence
<220> FEATURE:
<223> OTHER INFORMATION: oligonucleotide

<400> SEQUENCE: 357
uaccgcaagc ugcuggaggg caaggagug                                    29

<210> SEQ ID NO 358
<211> LENGTH: 29
<212> TYPE: RNA
<213> ORGANISM: Artificial Sequence
<220> FEATURE:
<223> OTHER INFORMATION: oligonucleotide

<400> SEQUENCE: 358
accgcaagcu gcuggagggc aaggagugc                                    29

<210> SEQ ID NO 359
<211> LENGTH: 29
<212> TYPE: RNA
<213> ORGANISM: Artificial Sequence
<220> FEATURE:
<223> OTHER INFORMATION: oligonucleotide

<400> SEQUENCE: 359
ccgcaagcug cuggagggca aggagugca                                    29

<210> SEQ ID NO 360
<211> LENGTH: 29
<212> TYPE: RNA
<213> ORGANISM: Artificial Sequence
<220> FEATURE:
<223> OTHER INFORMATION: oligonucleotide

<400> SEQUENCE: 360
cgcaagcugc uggagggcaa ggagugcag                                    29

<210> SEQ ID NO 361
<211> LENGTH: 29
<212> TYPE: RNA
<213> ORGANISM: Artificial Sequence
<220> FEATURE:
<223> OTHER INFORMATION: oligonucleotide

<400> SEQUENCE: 361
gcaagcugcu ggagggcaag gagugcagg                                    29

<210> SEQ ID NO 362
<211> LENGTH: 29
<212> TYPE: RNA
<213> ORGANISM: Artificial Sequence
<220> FEATURE:
<223> OTHER INFORMATION: oligonucleotide

<400> SEQUENCE: 362
caagcugcug gagggcaagg agugcaggc                                    29

<210> SEQ ID NO 363
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 363
aagcugcugg agggcaagga gugcaggcu                                29

<210> SEQ ID NO 364
<211> LENGTH: 29
<212> TYPE: RNA
<213> ORGANISM: Artificial Sequence
<220> FEATURE:
<223> OTHER INFORMATION: oligonucleotide

<400> SEQUENCE: 364
agcugcugga gggcaaggag ugcaggcug                                29

<210> SEQ ID NO 365
<211> LENGTH: 29
<212> TYPE: RNA
<213> ORGANISM: Artificial Sequence
<220> FEATURE:
<223> OTHER INFORMATION: oligonucleotide

<400> SEQUENCE: 365
gcugcuggag ggcaaggagu gcaggcuga                                29

<210> SEQ ID NO 366
<211> LENGTH: 29
<212> TYPE: RNA
<213> ORGANISM: Artificial Sequence
<220> FEATURE:
<223> OTHER INFORMATION: oligonucleotide

<400> SEQUENCE: 366
cugcuggagg gcaaggagug caggcugaa                                29

<210> SEQ ID NO 367
<211> LENGTH: 29
<212> TYPE: RNA
<213> ORGANISM: Artificial Sequence
<220> FEATURE:
<223> OTHER INFORMATION: oligonucleotide

<400> SEQUENCE: 367
ugcuggaggg caaggagugc aggcugaau                                29

<210> SEQ ID NO 368
<211> LENGTH: 29
<212> TYPE: RNA
<213> ORGANISM: Artificial Sequence
<220> FEATURE:
<223> OTHER INFORMATION: oligonucleotide

<400> SEQUENCE: 368
gcuggagggc aaggagugca ggcugaaug                                29

<210> SEQ ID NO 369
<211> LENGTH: 29
<212> TYPE: RNA
<213> ORGANISM: Artificial Sequence
<220> FEATURE:
<223> OTHER INFORMATION: oligonucleotide

<400> SEQUENCE: 369
cuggagggca aggagugcag gcugaaugg                                29
```

```
<210> SEQ ID NO 370
<211> LENGTH: 29
<212> TYPE: RNA
<213> ORGANISM: Artificial Sequence
<220> FEATURE:
<223> OTHER INFORMATION: oligonucleotide

<400> SEQUENCE: 370
uggagggcaa ggagugcagg cugaauggc                              29

<210> SEQ ID NO 371
<211> LENGTH: 29
<212> TYPE: RNA
<213> ORGANISM: Artificial Sequence
<220> FEATURE:
<223> OTHER INFORMATION: oligonucleotide

<400> SEQUENCE: 371
ggagggcaag gagugcaggc ugaauggcg                              29

<210> SEQ ID NO 372
<211> LENGTH: 29
<212> TYPE: RNA
<213> ORGANISM: Artificial Sequence
<220> FEATURE:
<223> OTHER INFORMATION: oligonucleotide

<400> SEQUENCE: 372
gagggcaagg agugcaggcu gaauggcga                              29

<210> SEQ ID NO 373
<211> LENGTH: 29
<212> TYPE: RNA
<213> ORGANISM: Artificial Sequence
<220> FEATURE:
<223> OTHER INFORMATION: oligonucleotide

<400> SEQUENCE: 373
agggcaagga gugcaggcug aauggcgaa                              29

<210> SEQ ID NO 374
<211> LENGTH: 29
<212> TYPE: RNA
<213> ORGANISM: Artificial Sequence
<220> FEATURE:
<223> OTHER INFORMATION: oligonucleotide

<400> SEQUENCE: 374
gggcaaggag ugcaggcuga auggcgaag                              29

<210> SEQ ID NO 375
<211> LENGTH: 29
<212> TYPE: RNA
<213> ORGANISM: Artificial Sequence
<220> FEATURE:
<223> OTHER INFORMATION: oligonucleotide

<400> SEQUENCE: 375
ggcaaggagu gcaggcugaa uggcgaagg                              29

<210> SEQ ID NO 376
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 376
gcaaggagug caggcugaau ggcgaaggc                              29

<210> SEQ ID NO 377
<211> LENGTH: 29
<212> TYPE: RNA
<213> ORGANISM: Artificial Sequence
<220> FEATURE:
<223> OTHER INFORMATION: oligonucleotide

<400> SEQUENCE: 377
caaggagugc aggcugaaug gcgaaggcg                              29

<210> SEQ ID NO 378
<211> LENGTH: 29
<212> TYPE: RNA
<213> ORGANISM: Artificial Sequence
<220> FEATURE:
<223> OTHER INFORMATION: oligonucleotide

<400> SEQUENCE: 378
aaggagugca ggcugaaugg cgaaggcgu                              29

<210> SEQ ID NO 379
<211> LENGTH: 98
<212> TYPE: DNA
<213> ORGANISM: Homo sapiens

<400> SEQUENCE: 379
tgggcttctg gtgggcagtg agaaggtgac catgcagaac ctcaatgacc gcctggcctc    60
ctacctggac aaggtgcgtg ctctggagga ggccaacg                            98

<210> SEQ ID NO 380
<211> LENGTH: 98
<212> TYPE: DNA
<213> ORGANISM: Homo sapiens

<400> SEQUENCE: 380
tgggcttctg gtgggcagtg agaaggtgac catgcagaac cccaatgacc gcctggcctc    60
ctacctggac aaggtgcgtg ctctggagga ggccaacg                            98

<210> SEQ ID NO 381
<211> LENGTH: 29
<212> TYPE: RNA
<213> ORGANISM: Artificial Sequence
<220> FEATURE:
<223> OTHER INFORMATION: oligonucleotide

<400> SEQUENCE: 381
ggcagugaga aggugaccau gcagaaccc                              29

<210> SEQ ID NO 382
<211> LENGTH: 29
<212> TYPE: RNA
<213> ORGANISM: Artificial Sequence
<220> FEATURE:
<223> OTHER INFORMATION: oligonucleotide

<400> SEQUENCE: 382
gcagugagaa ggugaccaug cagaacccc                              29
```

<210> SEQ ID NO 383
<211> LENGTH: 29
<212> TYPE: RNA
<213> ORGANISM: Artificial Sequence
<220> FEATURE:
<223> OTHER INFORMATION: oligonucleotide

<400> SEQUENCE: 383
cagugagaag gugaccaugc agaacccca                                   29

<210> SEQ ID NO 384
<211> LENGTH: 29
<212> TYPE: RNA
<213> ORGANISM: Artificial Sequence
<220> FEATURE:
<223> OTHER INFORMATION: oligonucleotide

<400> SEQUENCE: 384
agugagaagg ugaccaugca gaaccccaa                                   29

<210> SEQ ID NO 385
<211> LENGTH: 29
<212> TYPE: RNA
<213> ORGANISM: Artificial Sequence
<220> FEATURE:
<223> OTHER INFORMATION: oligonucleotide

<400> SEQUENCE: 385
gugagaaggu gaccaugcag aaccccaau                                   29

<210> SEQ ID NO 386
<211> LENGTH: 29
<212> TYPE: RNA
<213> ORGANISM: Artificial Sequence
<220> FEATURE:
<223> OTHER INFORMATION: oligonucleotide

<400> SEQUENCE: 386
ugagaaggug accaugcaga accccaaug                                   29

<210> SEQ ID NO 387
<211> LENGTH: 29
<212> TYPE: RNA
<213> ORGANISM: Artificial Sequence
<220> FEATURE:
<223> OTHER INFORMATION: oligonucleotide

<400> SEQUENCE: 387
gagaagguga ccaugcagaa ccccaauga                                   29

<210> SEQ ID NO 388
<211> LENGTH: 29
<212> TYPE: RNA
<213> ORGANISM: Artificial Sequence
<220> FEATURE:
<223> OTHER INFORMATION: oligonucleotide

<400> SEQUENCE: 388
agaaggugac caugcagaac cccaaugac                                   29

<210> SEQ ID NO 389
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 389
gaaggugacc augcagaacc ccaaugacc                                    29

<210> SEQ ID NO 390
<211> LENGTH: 29
<212> TYPE: RNA
<213> ORGANISM: Artificial Sequence
<220> FEATURE:
<223> OTHER INFORMATION: oligonucleotide

<400> SEQUENCE: 390
aaggugacca ugcagaaccc caaugaccg                                    29

<210> SEQ ID NO 391
<211> LENGTH: 29
<212> TYPE: RNA
<213> ORGANISM: Artificial Sequence
<220> FEATURE:
<223> OTHER INFORMATION: oligonucleotide

<400> SEQUENCE: 391
aggugaccau gcagaacccc aaugaccgc                                    29

<210> SEQ ID NO 392
<211> LENGTH: 29
<212> TYPE: RNA
<213> ORGANISM: Artificial Sequence
<220> FEATURE:
<223> OTHER INFORMATION: oligonucleotide

<400> SEQUENCE: 392
ggugaccaug cagaacccca augaccgcc                                    29

<210> SEQ ID NO 393
<211> LENGTH: 29
<212> TYPE: RNA
<213> ORGANISM: Artificial Sequence
<220> FEATURE:
<223> OTHER INFORMATION: oligonucleotide

<400> SEQUENCE: 393
gugaccaugc agaaccccaa ugaccgccu                                    29

<210> SEQ ID NO 394
<211> LENGTH: 29
<212> TYPE: RNA
<213> ORGANISM: Artificial Sequence
<220> FEATURE:
<223> OTHER INFORMATION: oligonucleotide

<400> SEQUENCE: 394
ugaccaugca gaaccccaau gaccgccug                                    29

<210> SEQ ID NO 395
<211> LENGTH: 29
<212> TYPE: RNA
<213> ORGANISM: Artificial Sequence
<220> FEATURE:
<223> OTHER INFORMATION: oligonucleotide

<400> SEQUENCE: 395
gaccaugcag aaccccaaug accgccugg                                    29
```

<210> SEQ ID NO 396
<211> LENGTH: 29
<212> TYPE: RNA
<213> ORGANISM: Artificial Sequence
<220> FEATURE:
<223> OTHER INFORMATION: oligonucleotide

<400> SEQUENCE: 396
accaugcaga accccaauga ccgccuggc                                29

<210> SEQ ID NO 397
<211> LENGTH: 29
<212> TYPE: RNA
<213> ORGANISM: Artificial Sequence
<220> FEATURE:
<223> OTHER INFORMATION: oligonucleotide

<400> SEQUENCE: 397
ccaugcagaa ccccaaugac cgccuggcc                                29

<210> SEQ ID NO 398
<211> LENGTH: 29
<212> TYPE: RNA
<213> ORGANISM: Artificial Sequence
<220> FEATURE:
<223> OTHER INFORMATION: oligonucleotide

<400> SEQUENCE: 398
caugcagaac cccaaugacc gccuggccu                                29

<210> SEQ ID NO 399
<211> LENGTH: 29
<212> TYPE: RNA
<213> ORGANISM: Artificial Sequence
<220> FEATURE:
<223> OTHER INFORMATION: oligonucleotide

<400> SEQUENCE: 399
augcagaacc ccaaugaccg ccuggccuc                                29

<210> SEQ ID NO 400
<211> LENGTH: 29
<212> TYPE: RNA
<213> ORGANISM: Artificial Sequence
<220> FEATURE:
<223> OTHER INFORMATION: oligonucleotide

<400> SEQUENCE: 400
ugcagaaccc caaugaccgc cuggccucc                                29

<210> SEQ ID NO 401
<211> LENGTH: 29
<212> TYPE: RNA
<213> ORGANISM: Artificial Sequence
<220> FEATURE:
<223> OTHER INFORMATION: oligonucleotide

<400> SEQUENCE: 401
gcagaacccc aaugaccgcc uggccuccu                                29

<210> SEQ ID NO 402
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 402
cagaacccca augaccgccu ggccuccua                                    29

<210> SEQ ID NO 403
<211> LENGTH: 29
<212> TYPE: RNA
<213> ORGANISM: Artificial Sequence
<220> FEATURE:
<223> OTHER INFORMATION: oligonucleotide

<400> SEQUENCE: 403
agaaccccaa ugaccgccug gccuccuac                                    29

<210> SEQ ID NO 404
<211> LENGTH: 29
<212> TYPE: RNA
<213> ORGANISM: Artificial Sequence
<220> FEATURE:
<223> OTHER INFORMATION: oligonucleotide

<400> SEQUENCE: 404
gaaccccaau gaccgccugg ccuccuacc                                    29

<210> SEQ ID NO 405
<211> LENGTH: 29
<212> TYPE: RNA
<213> ORGANISM: Artificial Sequence
<220> FEATURE:
<223> OTHER INFORMATION: oligonucleotide

<400> SEQUENCE: 405
aaccccaaug accgccuggc cuccuaccu                                    29

<210> SEQ ID NO 406
<211> LENGTH: 29
<212> TYPE: RNA
<213> ORGANISM: Artificial Sequence
<220> FEATURE:
<223> OTHER INFORMATION: oligonucleotide

<400> SEQUENCE: 406
accccaauga ccgccuggcc uccuaccug                                    29

<210> SEQ ID NO 407
<211> LENGTH: 29
<212> TYPE: RNA
<213> ORGANISM: Artificial Sequence
<220> FEATURE:
<223> OTHER INFORMATION: oligonucleotide

<400> SEQUENCE: 407
ccccaaugac cgccuggccu ccuaccugg                                    29

<210> SEQ ID NO 408
<211> LENGTH: 29
<212> TYPE: RNA
<213> ORGANISM: Artificial Sequence
<220> FEATURE:
<223> OTHER INFORMATION: oligonucleotide

<400> SEQUENCE: 408
cccaaugacc gccuggccuc cuaccugga                                    29
```

```
<210> SEQ ID NO 409
<211> LENGTH: 29
<212> TYPE: RNA
<213> ORGANISM: Artificial Sequence
<220> FEATURE:
<223> OTHER INFORMATION: oligonucleotide

<400> SEQUENCE: 409
ccaaugaccg ccuggccucc uaccuggac                                              29

<210> SEQ ID NO 410
<211> LENGTH: 98
<212> TYPE: DNA
<213> ORGANISM: Homo sapiens

<400> SEQUENCE: 410
tgggcttctg gtgggcagtg agaaggtgac catgcagaac ctcaatgacc gcctggcctc            60
ctacctggac aaggtgcgtg ctctggagga ggccaacg                                    98

<210> SEQ ID NO 411
<211> LENGTH: 98
<212> TYPE: DNA
<213> ORGANISM: Homo sapiens

<400> SEQUENCE: 411
tgggcttctg gtgggcagtg agaaggtgac catgcagaac cacaatgacc gcctggcctc            60
ctacctggac aaggtgcgtg ctctggagga ggccaacg                                    98

<210> SEQ ID NO 412
<211> LENGTH: 29
<212> TYPE: RNA
<213> ORGANISM: Artificial Sequence
<220> FEATURE:
<223> OTHER INFORMATION: oligonucleotide

<400> SEQUENCE: 412
ggcagugaga aggugaccau gcagaacca                                              29

<210> SEQ ID NO 413
<211> LENGTH: 29
<212> TYPE: RNA
<213> ORGANISM: Artificial Sequence
<220> FEATURE:
<223> OTHER INFORMATION: oligonucleotide

<400> SEQUENCE: 413
gcagugagaa ggugaccaug cagaaccac                                              29

<210> SEQ ID NO 414
<211> LENGTH: 29
<212> TYPE: RNA
<213> ORGANISM: Artificial Sequence
<220> FEATURE:
<223> OTHER INFORMATION: oligonucleotide

<400> SEQUENCE: 414
cagugagaag gugaccaugc agaaccaca                                              29

<210> SEQ ID NO 415
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 415
agugagaagg ugaccaugca gaaccacaa                                          29

<210> SEQ ID NO 416
<211> LENGTH: 29
<212> TYPE: RNA
<213> ORGANISM: Artificial Sequence
<220> FEATURE:
<223> OTHER INFORMATION: oligonucleotide

<400> SEQUENCE: 416
gugagaaggu gaccaugcag aaccacaau                                          29

<210> SEQ ID NO 417
<211> LENGTH: 29
<212> TYPE: RNA
<213> ORGANISM: Artificial Sequence
<220> FEATURE:
<223> OTHER INFORMATION: oligonucleotide

<400> SEQUENCE: 417
ugagaaggug accaugcaga accacaaug                                          29

<210> SEQ ID NO 418
<211> LENGTH: 29
<212> TYPE: RNA
<213> ORGANISM: Artificial Sequence
<220> FEATURE:
<223> OTHER INFORMATION: oligonucleotide

<400> SEQUENCE: 418
gagaagguga ccaugcagaa ccacaauga                                          29

<210> SEQ ID NO 419
<211> LENGTH: 29
<212> TYPE: RNA
<213> ORGANISM: Artificial Sequence
<220> FEATURE:
<223> OTHER INFORMATION: oligonucleotide

<400> SEQUENCE: 419
agaaggugac caugcagaac cacaaugac                                          29

<210> SEQ ID NO 420
<211> LENGTH: 29
<212> TYPE: RNA
<213> ORGANISM: Artificial Sequence
<220> FEATURE:
<223> OTHER INFORMATION: oligonucleotide

<400> SEQUENCE: 420
gaaggugacc augcagaacc acaaugacc                                          29

<210> SEQ ID NO 421
<211> LENGTH: 29
<212> TYPE: RNA
<213> ORGANISM: Artificial Sequence
<220> FEATURE:
<223> OTHER INFORMATION: oligonucleotide

<400> SEQUENCE: 421
aaggugacca ugcagaacca caaugaccg                                          29
```

```
<210> SEQ ID NO 422
<211> LENGTH: 29
<212> TYPE: RNA
<213> ORGANISM: Artificial Sequence
<220> FEATURE:
<223> OTHER INFORMATION: oligonucleotide

<400> SEQUENCE: 422
aggugaccau gcagaaccac aaugaccgc                                           29

<210> SEQ ID NO 423
<211> LENGTH: 29
<212> TYPE: RNA
<213> ORGANISM: Artificial Sequence
<220> FEATURE:
<223> OTHER INFORMATION: oligonucleotide

<400> SEQUENCE: 423
ggugaccaug cagaaccaca augaccgcc                                           29

<210> SEQ ID NO 424
<211> LENGTH: 29
<212> TYPE: RNA
<213> ORGANISM: Artificial Sequence
<220> FEATURE:
<223> OTHER INFORMATION: oligonucleotide

<400> SEQUENCE: 424
gugaccaugc agaaccacaa ugaccgccu                                           29

<210> SEQ ID NO 425
<211> LENGTH: 29
<212> TYPE: RNA
<213> ORGANISM: Artificial Sequence
<220> FEATURE:
<223> OTHER INFORMATION: oligonucleotide

<400> SEQUENCE: 425
ugaccaugca gaaccacaau gaccgccug                                           29

<210> SEQ ID NO 426
<211> LENGTH: 29
<212> TYPE: RNA
<213> ORGANISM: Artificial Sequence
<220> FEATURE:
<223> OTHER INFORMATION: oligonucleotide

<400> SEQUENCE: 426
gaccaugcag aaccacaaug accgccugg                                           29

<210> SEQ ID NO 427
<211> LENGTH: 29
<212> TYPE: RNA
<213> ORGANISM: Artificial Sequence
<220> FEATURE:
<223> OTHER INFORMATION: oligonucleotide

<400> SEQUENCE: 427
accaugcaga accacaauga ccgccuggc                                           29

<210> SEQ ID NO 428
<211> LENGTH: 29
<212> TYPE: RNA
<213> ORGANISM: Artificial Sequence
<220> FEATURE:
<223> OTHER INFORMATION: oligonucleotide
```

-continued

```
<400> SEQUENCE: 428
ccaugcagaa ccacaaugac cgccuggcc                                       29

<210> SEQ ID NO 429
<211> LENGTH: 29
<212> TYPE: RNA
<213> ORGANISM: Artificial Sequence
<220> FEATURE:
<223> OTHER INFORMATION: oligonucleotide

<400> SEQUENCE: 429
caugcagaac cacaaugacc gccuggccu                                       29

<210> SEQ ID NO 430
<211> LENGTH: 29
<212> TYPE: RNA
<213> ORGANISM: Artificial Sequence
<220> FEATURE:
<223> OTHER INFORMATION: oligonucleotide

<400> SEQUENCE: 430
augcagaacc acaaugaccg ccuggccuc                                       29

<210> SEQ ID NO 431
<211> LENGTH: 29
<212> TYPE: RNA
<213> ORGANISM: Artificial Sequence
<220> FEATURE:
<223> OTHER INFORMATION: oligonucleotide

<400> SEQUENCE: 431
ugcagaacca caaugaccgc cuggccucc                                       29

<210> SEQ ID NO 432
<211> LENGTH: 29
<212> TYPE: RNA
<213> ORGANISM: Artificial Sequence
<220> FEATURE:
<223> OTHER INFORMATION: oligonucleotide

<400> SEQUENCE: 432
gcagaaccac aaugaccgcc uggccuccu                                       29

<210> SEQ ID NO 433
<211> LENGTH: 29
<212> TYPE: RNA
<213> ORGANISM: Artificial Sequence
<220> FEATURE:
<223> OTHER INFORMATION: oligonucleotide

<400> SEQUENCE: 433
cagaaccaca augaccgccu ggccuccua                                       29

<210> SEQ ID NO 434
<211> LENGTH: 29
<212> TYPE: RNA
<213> ORGANISM: Artificial Sequence
<220> FEATURE:
<223> OTHER INFORMATION: oligonucleotide

<400> SEQUENCE: 434
agaaccacaa ugaccgccug gccuccuac                                       29
```

```
<210> SEQ ID NO 435
<211> LENGTH: 29
<212> TYPE: RNA
<213> ORGANISM: Artificial Sequence
<220> FEATURE:
<223> OTHER INFORMATION: oligonucleotide

<400> SEQUENCE: 435
gaaccacaau gaccgccugg ccuccuacc                                    29

<210> SEQ ID NO 436
<211> LENGTH: 29
<212> TYPE: RNA
<213> ORGANISM: Artificial Sequence
<220> FEATURE:
<223> OTHER INFORMATION: oligonucleotide

<400> SEQUENCE: 436
aaccacaaug accgccuggc cuccuaccu                                    29

<210> SEQ ID NO 437
<211> LENGTH: 29
<212> TYPE: RNA
<213> ORGANISM: Artificial Sequence
<220> FEATURE:
<223> OTHER INFORMATION: oligonucleotide

<400> SEQUENCE: 437
accacaauga ccgccuggcc uccuaccug                                    29

<210> SEQ ID NO 438
<211> LENGTH: 29
<212> TYPE: RNA
<213> ORGANISM: Artificial Sequence
<220> FEATURE:
<223> OTHER INFORMATION: oligonucleotide

<400> SEQUENCE: 438
ccacaaugac cgccuggccu ccuaccugg                                    29

<210> SEQ ID NO 439
<211> LENGTH: 29
<212> TYPE: RNA
<213> ORGANISM: Artificial Sequence
<220> FEATURE:
<223> OTHER INFORMATION: oligonucleotide

<400> SEQUENCE: 439
cacaaugacc gccuggccuc cuaccugga                                    29

<210> SEQ ID NO 440
<211> LENGTH: 29
<212> TYPE: RNA
<213> ORGANISM: Artificial Sequence
<220> FEATURE:
<223> OTHER INFORMATION: oligonucleotide

<400> SEQUENCE: 440
acaaugaccg ccuggccucc uaccuggac                                    29

<210> SEQ ID NO 441
<211> LENGTH: 98
<212> TYPE: DNA
<213> ORGANISM: Homo sapiens
```

-continued

<400> SEQUENCE: 441
tgggcttctg gtgggcagtg agaaggtgac catgcagaac ctcaatgacc gcctggcctc    60
ctacctggac aaggtgcgtg ctctggagga ggccaacg    98

<210> SEQ ID NO 442
<211> LENGTH: 98
<212> TYPE: DNA
<213> ORGANISM: Homo sapiens

<400> SEQUENCE: 442
tgggcttctg gtgggcagtg agaaggtgac catgcagaac ctcgatgacc gcctggcctc    60
ctacctggac aaggtgcgtg ctctggagga ggccaacg    98

<210> SEQ ID NO 443
<211> LENGTH: 29
<212> TYPE: RNA
<213> ORGANISM: Artificial Sequence
<220> FEATURE:
<223> OTHER INFORMATION: oligonucleotide

<400> SEQUENCE: 443
cagugagaag gugaccaugc agaaccucg    29

<210> SEQ ID NO 444
<211> LENGTH: 29
<212> TYPE: RNA
<213> ORGANISM: Artificial Sequence
<220> FEATURE:
<223> OTHER INFORMATION: oligonucleotide

<400> SEQUENCE: 444
agugagaagg ugaccaugca gaaccucga    29

<210> SEQ ID NO 445
<211> LENGTH: 29
<212> TYPE: RNA
<213> ORGANISM: Artificial Sequence
<220> FEATURE:
<223> OTHER INFORMATION: oligonucleotide

<400> SEQUENCE: 445
gugagaaggu gaccaugcag aaccucgau    29

<210> SEQ ID NO 446
<211> LENGTH: 29
<212> TYPE: RNA
<213> ORGANISM: Artificial Sequence
<220> FEATURE:
<223> OTHER INFORMATION: oligonucleotide

<400> SEQUENCE: 446
ugagaaggug accaugcaga accucgaug    29

<210> SEQ ID NO 447
<211> LENGTH: 29
<212> TYPE: RNA
<213> ORGANISM: Artificial Sequence
<220> FEATURE:
<223> OTHER INFORMATION: oligonucleotide

<400> SEQUENCE: 447
gagaagguga ccaugcagaa ccucgauga    29

```
<210> SEQ ID NO 448
<211> LENGTH: 29
<212> TYPE: RNA
<213> ORGANISM: Artificial Sequence
<220> FEATURE:
<223> OTHER INFORMATION: oligonucleotide

<400> SEQUENCE: 448
agaaggugac caugcagaac cucgaugac                                29

<210> SEQ ID NO 449
<211> LENGTH: 29
<212> TYPE: RNA
<213> ORGANISM: Artificial Sequence
<220> FEATURE:
<223> OTHER INFORMATION: oligonucleotide

<400> SEQUENCE: 449
gaaggugacc augcagaacc ucgaugacc                                29

<210> SEQ ID NO 450
<211> LENGTH: 29
<212> TYPE: RNA
<213> ORGANISM: Artificial Sequence
<220> FEATURE:
<223> OTHER INFORMATION: oligonucleotide

<400> SEQUENCE: 450
aaggugacca ugcagaaccu cgaugaccg                                29

<210> SEQ ID NO 451
<211> LENGTH: 29
<212> TYPE: RNA
<213> ORGANISM: Artificial Sequence
<220> FEATURE:
<223> OTHER INFORMATION: oligonucleotide

<400> SEQUENCE: 451
aggugaccau gcagaaccuc gaugaccgc                                29

<210> SEQ ID NO 452
<211> LENGTH: 29
<212> TYPE: RNA
<213> ORGANISM: Artificial Sequence
<220> FEATURE:
<223> OTHER INFORMATION: oligonucleotide

<400> SEQUENCE: 452
ggugaccaug cagaaccucg augaccgcc                                29

<210> SEQ ID NO 453
<211> LENGTH: 29
<212> TYPE: RNA
<213> ORGANISM: Artificial Sequence
<220> FEATURE:
<223> OTHER INFORMATION: oligonucleotide

<400> SEQUENCE: 453
gugaccaugc agaaccucga ugaccgccu                                29

<210> SEQ ID NO 454
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 454
ugaccaugca gaaccucgau gaccgccug                                        29

<210> SEQ ID NO 455
<211> LENGTH: 29
<212> TYPE: RNA
<213> ORGANISM: Artificial Sequence
<220> FEATURE:
<223> OTHER INFORMATION: oligonucleotide

<400> SEQUENCE: 455
gaccaugcag aaccucgaug accgccugg                                        29

<210> SEQ ID NO 456
<211> LENGTH: 29
<212> TYPE: RNA
<213> ORGANISM: Artificial Sequence
<220> FEATURE:
<223> OTHER INFORMATION: oligonucleotide

<400> SEQUENCE: 456
accaugcaga accucgauga ccgccuggc                                        29

<210> SEQ ID NO 457
<211> LENGTH: 29
<212> TYPE: RNA
<213> ORGANISM: Artificial Sequence
<220> FEATURE:
<223> OTHER INFORMATION: oligonucleotide

<400> SEQUENCE: 457
ccaugcagaa ccucgaugac cgccuggcc                                        29

<210> SEQ ID NO 458
<211> LENGTH: 29
<212> TYPE: RNA
<213> ORGANISM: Artificial Sequence
<220> FEATURE:
<223> OTHER INFORMATION: oligonucleotide

<400> SEQUENCE: 458
caugcagaac cucgaugacc gccuggccu                                        29

<210> SEQ ID NO 459
<211> LENGTH: 29
<212> TYPE: RNA
<213> ORGANISM: Artificial Sequence
<220> FEATURE:
<223> OTHER INFORMATION: oligonucleotide

<400> SEQUENCE: 459
augcagaacc ucgaugaccg ccuggccuc                                        29

<210> SEQ ID NO 460
<211> LENGTH: 29
<212> TYPE: RNA
<213> ORGANISM: Artificial Sequence
<220> FEATURE:
<223> OTHER INFORMATION: oligonucleotide

<400> SEQUENCE: 460
ugcagaaccu cgaugaccgc cuggccucc                                        29
```

<210> SEQ ID NO 461
<211> LENGTH: 29
<212> TYPE: RNA
<213> ORGANISM: Artificial Sequence
<220> FEATURE:
<223> OTHER INFORMATION: oligonucleotide

<400> SEQUENCE: 461
gcagaaccuc gaugaccgcc uggccuccu                              29

<210> SEQ ID NO 462
<211> LENGTH: 29
<212> TYPE: RNA
<213> ORGANISM: Artificial Sequence
<220> FEATURE:
<223> OTHER INFORMATION: oligonucleotide

<400> SEQUENCE: 462
cagaaccucg augaccgccu ggccuccua                              29

<210> SEQ ID NO 463
<211> LENGTH: 29
<212> TYPE: RNA
<213> ORGANISM: Artificial Sequence
<220> FEATURE:
<223> OTHER INFORMATION: oligonucleotide

<400> SEQUENCE: 463
agaaccucga ugaccgccug gccuccuac                              29

<210> SEQ ID NO 464
<211> LENGTH: 29
<212> TYPE: RNA
<213> ORGANISM: Artificial Sequence
<220> FEATURE:
<223> OTHER INFORMATION: oligonucleotide

<400> SEQUENCE: 464
gaaccucgau gaccgccugg ccuccuacc                              29

<210> SEQ ID NO 465
<211> LENGTH: 29
<212> TYPE: RNA
<213> ORGANISM: Artificial Sequence
<220> FEATURE:
<223> OTHER INFORMATION: oligonucleotide

<400> SEQUENCE: 465
aaccucgaug accgccuggc cuccuaccu                              29

<210> SEQ ID NO 466
<211> LENGTH: 29
<212> TYPE: RNA
<213> ORGANISM: Artificial Sequence
<220> FEATURE:
<223> OTHER INFORMATION: oligonucleotide

<400> SEQUENCE: 466
accucgauga ccgccuggcc uccuaccug                              29

<210> SEQ ID NO 467
<211> LENGTH: 29
<212> TYPE: RNA
<213> ORGANISM: Artificial Sequence
<220> FEATURE:
<223> OTHER INFORMATION: oligonucleotide

```
<400> SEQUENCE: 467
ccucgaugac cgccuggccu ccuaccugg                                29

<210> SEQ ID NO 468
<211> LENGTH: 29
<212> TYPE: RNA
<213> ORGANISM: Artificial Sequence
<220> FEATURE:
<223> OTHER INFORMATION: oligonucleotide

<400> SEQUENCE: 468
cucgaugacc gccuggccuc cuaccugga                                29

<210> SEQ ID NO 469
<211> LENGTH: 29
<212> TYPE: RNA
<213> ORGANISM: Artificial Sequence
<220> FEATURE:
<223> OTHER INFORMATION: oligonucleotide

<400> SEQUENCE: 469
ucgaugaccg ccuggccucc uaccuggac                                29

<210> SEQ ID NO 470
<211> LENGTH: 29
<212> TYPE: RNA
<213> ORGANISM: Artificial Sequence
<220> FEATURE:
<223> OTHER INFORMATION: oligonucleotide

<400> SEQUENCE: 470
cgaugaccgc cuggccuccu accuggaca                                29

<210> SEQ ID NO 471
<211> LENGTH: 29
<212> TYPE: RNA
<213> ORGANISM: Artificial Sequence
<220> FEATURE:
<223> OTHER INFORMATION: oligonucleotide

<400> SEQUENCE: 471
gaugaccgcc uggccuccua ccuggacaa                                29

<210> SEQ ID NO 472
<211> LENGTH: 98
<212> TYPE: DNA
<213> ORGANISM: Homo sapiens

<400> SEQUENCE: 472
tgggcttctg gtgggcagtg agaaggtgac catgcagaac ctcaatgacc gcctggcctc       60
ctacctggac aaggtgcgtg ctctggagga ggccaacg                              98

<210> SEQ ID NO 473
<211> LENGTH: 98
<212> TYPE: DNA
<213> ORGANISM: Homo sapiens

<400> SEQUENCE: 473
tgggcttctg gtgggcagtg agaaggtgac catgcagaac ctcagtgacc gcctggcctc       60
ctacctggac aaggtgcgtg ctctggagga ggccaacg                              98
```

-continued

```
<210> SEQ ID NO 474
<211> LENGTH: 29
<212> TYPE: RNA
<213> ORGANISM: Artificial Sequence
<220> FEATURE:
<223> OTHER INFORMATION: oligonucleotide

<400> SEQUENCE: 474
agugagaagg ugaccaugca gaaccucag                                    29

<210> SEQ ID NO 475
<211> LENGTH: 29
<212> TYPE: RNA
<213> ORGANISM: Artificial Sequence
<220> FEATURE:
<223> OTHER INFORMATION: oligonucleotide

<400> SEQUENCE: 475
gugagaaggu gaccaugcag aaccucagu                                    29

<210> SEQ ID NO 476
<211> LENGTH: 29
<212> TYPE: RNA
<213> ORGANISM: Artificial Sequence
<220> FEATURE:
<223> OTHER INFORMATION: oligonucleotide

<400> SEQUENCE: 476
ugagaaggug accaugcaga accucagug                                    29

<210> SEQ ID NO 477
<211> LENGTH: 29
<212> TYPE: RNA
<213> ORGANISM: Artificial Sequence
<220> FEATURE:
<223> OTHER INFORMATION: oligonucleotide

<400> SEQUENCE: 477
gagaagguga ccaugcagaa ccucaguga                                    29

<210> SEQ ID NO 478
<211> LENGTH: 29
<212> TYPE: RNA
<213> ORGANISM: Artificial Sequence
<220> FEATURE:
<223> OTHER INFORMATION: oligonucleotide

<400> SEQUENCE: 478
agaaggugac caugcagaac cucagugac                                    29

<210> SEQ ID NO 479
<211> LENGTH: 29
<212> TYPE: RNA
<213> ORGANISM: Artificial Sequence
<220> FEATURE:
<223> OTHER INFORMATION: oligonucleotide

<400> SEQUENCE: 479
gaaggugacc augcagaacc ucagugacc                                    29

<210> SEQ ID NO 480
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 480
aaggugacca ugcagaaccu cagugaccg                              29

<210> SEQ ID NO 481
<211> LENGTH: 29
<212> TYPE: RNA
<213> ORGANISM: Artificial Sequence
<220> FEATURE:
<223> OTHER INFORMATION: oligonucleotide

<400> SEQUENCE: 481
aggugaccau gcagaaccuc agugaccgc                              29

<210> SEQ ID NO 482
<211> LENGTH: 29
<212> TYPE: RNA
<213> ORGANISM: Artificial Sequence
<220> FEATURE:
<223> OTHER INFORMATION: oligonucleotide

<400> SEQUENCE: 482
ggugaccaug cagaaccuca gugaccgcc                              29

<210> SEQ ID NO 483
<211> LENGTH: 29
<212> TYPE: RNA
<213> ORGANISM: Artificial Sequence
<220> FEATURE:
<223> OTHER INFORMATION: oligonucleotide

<400> SEQUENCE: 483
gugaccaugc agaaccucag ugaccgccu                              29

<210> SEQ ID NO 484
<211> LENGTH: 29
<212> TYPE: RNA
<213> ORGANISM: Artificial Sequence
<220> FEATURE:
<223> OTHER INFORMATION: oligonucleotide

<400> SEQUENCE: 484
ugaccaugca gaaccucagu gaccgccug                              29

<210> SEQ ID NO 485
<211> LENGTH: 29
<212> TYPE: RNA
<213> ORGANISM: Artificial Sequence
<220> FEATURE:
<223> OTHER INFORMATION: oligonucleotide

<400> SEQUENCE: 485
gaccaugcag aaccucagug accgccugg                              29

<210> SEQ ID NO 486
<211> LENGTH: 29
<212> TYPE: RNA
<213> ORGANISM: Artificial Sequence
<220> FEATURE:
<223> OTHER INFORMATION: oligonucleotide

<400> SEQUENCE: 486
accaugcaga accucaguga ccgccuggc                              29
```

<210> SEQ ID NO 487
<211> LENGTH: 29
<212> TYPE: RNA
<213> ORGANISM: Artificial Sequence
<220> FEATURE:
<223> OTHER INFORMATION: oligonucleotide

<400> SEQUENCE: 487
ccaugcagaa ccucagugac cgccuggcc                                            29

<210> SEQ ID NO 488
<211> LENGTH: 29
<212> TYPE: RNA
<213> ORGANISM: Artificial Sequence
<220> FEATURE:
<223> OTHER INFORMATION: oligonucleotide

<400> SEQUENCE: 488
caugcagaac cucagugacc gccuggccu                                            29

<210> SEQ ID NO 489
<211> LENGTH: 29
<212> TYPE: RNA
<213> ORGANISM: Artificial Sequence
<220> FEATURE:
<223> OTHER INFORMATION: oligonucleotide

<400> SEQUENCE: 489
augcagaacc ucagugaccg ccuggccuc                                            29

<210> SEQ ID NO 490
<211> LENGTH: 29
<212> TYPE: RNA
<213> ORGANISM: Artificial Sequence
<220> FEATURE:
<223> OTHER INFORMATION: oligonucleotide

<400> SEQUENCE: 490
ugcagaaccu cagugaccgc cuggccucc                                            29

<210> SEQ ID NO 491
<211> LENGTH: 29
<212> TYPE: RNA
<213> ORGANISM: Artificial Sequence
<220> FEATURE:
<223> OTHER INFORMATION: oligonucleotide

<400> SEQUENCE: 491
gcagaaccuc agugaccgcc uggccuccu                                            29

<210> SEQ ID NO 492
<211> LENGTH: 29
<212> TYPE: RNA
<213> ORGANISM: Artificial Sequence
<220> FEATURE:
<223> OTHER INFORMATION: oligonucleotide

<400> SEQUENCE: 492
cagaaccuca gugaccgccu ggccuccua                                            29

<210> SEQ ID NO 493
<211> LENGTH: 29
<212> TYPE: RNA
<213> ORGANISM: Artificial Sequence
<220> FEATURE:
<223> OTHER INFORMATION: oligonucleotide -continued

```
<400> SEQUENCE: 493
agaaccucag ugaccgccug gccuccuac                                              29

<210> SEQ ID NO 494
<211> LENGTH: 29
<212> TYPE: RNA
<213> ORGANISM: Artificial Sequence
<220> FEATURE:
<223> OTHER INFORMATION: oligonucleotide

<400> SEQUENCE: 494
gaaccucagu gaccgccugg ccuccuacc                                              29

<210> SEQ ID NO 495
<211> LENGTH: 29
<212> TYPE: RNA
<213> ORGANISM: Artificial Sequence
<220> FEATURE:
<223> OTHER INFORMATION: oligonucleotide

<400> SEQUENCE: 495
aaccucagug accgccuggc cuccuaccu                                              29

<210> SEQ ID NO 496
<211> LENGTH: 29
<212> TYPE: RNA
<213> ORGANISM: Artificial Sequence
<220> FEATURE:
<223> OTHER INFORMATION: oligonucleotide

<400> SEQUENCE: 496
accucaguga ccgccuggcc uccuaccug                                              29

<210> SEQ ID NO 497
<211> LENGTH: 29
<212> TYPE: RNA
<213> ORGANISM: Artificial Sequence
<220> FEATURE:
<223> OTHER INFORMATION: oligonucleotide

<400> SEQUENCE: 497
ccucagugac cgccuggccu ccuaccugg                                              29

<210> SEQ ID NO 498
<211> LENGTH: 29
<212> TYPE: RNA
<213> ORGANISM: Artificial Sequence
<220> FEATURE:
<223> OTHER INFORMATION: oligonucleotide

<400> SEQUENCE: 498
cucagugacc gccuggccuc cuaccugga                                              29

<210> SEQ ID NO 499
<211> LENGTH: 29
<212> TYPE: RNA
<213> ORGANISM: Artificial Sequence
<220> FEATURE:
<223> OTHER INFORMATION: oligonucleotide

<400> SEQUENCE: 499
ucagugaccg ccuggccucc uaccuggac                                              29
```

```
<210> SEQ ID NO 500
<211> LENGTH: 29
<212> TYPE: RNA
<213> ORGANISM: Artificial Sequence
<220> FEATURE:
<223> OTHER INFORMATION: oligonucleotide

<400> SEQUENCE: 500
cagugaccgc cuggccuccu accuggaca                                    29

<210> SEQ ID NO 501
<211> LENGTH: 29
<212> TYPE: RNA
<213> ORGANISM: Artificial Sequence
<220> FEATURE:
<223> OTHER INFORMATION: oligonucleotide

<400> SEQUENCE: 501
agugaccgcc uggccuccua ccuggacaa                                    29

<210> SEQ ID NO 502
<211> LENGTH: 29
<212> TYPE: RNA
<213> ORGANISM: Artificial Sequence
<220> FEATURE:
<223> OTHER INFORMATION: oligonucleotide

<400> SEQUENCE: 502
gugaccgccu ggccuccuac cuggacaag                                    29

<210> SEQ ID NO 503
<211> LENGTH: 98
<212> TYPE: DNA
<213> ORGANISM: Homo sapiens

<400> SEQUENCE: 503
tgggcttctg gtgggcagtg agaaggtgac catgcagaac ctcaatgacc gcctggcctc    60
ctacctggac aaggtgcgtg ctctggagga ggccaacg                            98

<210> SEQ ID NO 504
<211> LENGTH: 98
<212> TYPE: DNA
<213> ORGANISM: Homo sapiens

<400> SEQUENCE: 504
tgggcttctg gtgggcagtg agaaggtgac catgcagaac ctcaatgact gcctggcctc    60
ctacctggac aaggtgcgtg ctctggagga ggccaacg                            98

<210> SEQ ID NO 505
<211> LENGTH: 29
<212> TYPE: RNA
<213> ORGANISM: Artificial Sequence
<220> FEATURE:
<223> OTHER INFORMATION: oligonucleotide

<400> SEQUENCE: 505
gaaggugacc augcagaacc ucaaugacu                                    29

<210> SEQ ID NO 506
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 506
aaggugacca ugcagaaccu caaugacug                              29

<210> SEQ ID NO 507
<211> LENGTH: 29
<212> TYPE: RNA
<213> ORGANISM: Artificial Sequence
<220> FEATURE:
<223> OTHER INFORMATION: oligonucleotide

<400> SEQUENCE: 507
aggugaccau gcagaaccuc aaugacugc                              29

<210> SEQ ID NO 508
<211> LENGTH: 29
<212> TYPE: RNA
<213> ORGANISM: Artificial Sequence
<220> FEATURE:
<223> OTHER INFORMATION: oligonucleotide

<400> SEQUENCE: 508
ggugaccaug cagaaccuca augacugcc                              29

<210> SEQ ID NO 509
<211> LENGTH: 29
<212> TYPE: RNA
<213> ORGANISM: Artificial Sequence
<220> FEATURE:
<223> OTHER INFORMATION: oligonucleotide

<400> SEQUENCE: 509
gugaccaugc agaaccucaa ugacugccu                              29

<210> SEQ ID NO 510
<211> LENGTH: 29
<212> TYPE: RNA
<213> ORGANISM: Artificial Sequence
<220> FEATURE:
<223> OTHER INFORMATION: oligonucleotide

<400> SEQUENCE: 510
ugaccaugca gaaccucaau gacugccug                              29

<210> SEQ ID NO 511
<211> LENGTH: 29
<212> TYPE: RNA
<213> ORGANISM: Artificial Sequence
<220> FEATURE:
<223> OTHER INFORMATION: oligonucleotide

<400> SEQUENCE: 511
gaccaugcag aaccucaaug acugccugg                              29

<210> SEQ ID NO 512
<211> LENGTH: 29
<212> TYPE: RNA
<213> ORGANISM: Artificial Sequence
<220> FEATURE:
<223> OTHER INFORMATION: oligonucleotide

<400> SEQUENCE: 512
accaugcaga accucaauga cugccuggc                              29
```

```
<210> SEQ ID NO 513
<211> LENGTH: 29
<212> TYPE: RNA
<213> ORGANISM: Artificial Sequence
<220> FEATURE:
<223> OTHER INFORMATION: oligonucleotide

<400> SEQUENCE: 513
ccaugcagaa ccucaaugac ugccuggcc                                          29

<210> SEQ ID NO 514
<211> LENGTH: 29
<212> TYPE: RNA
<213> ORGANISM: Artificial Sequence
<220> FEATURE:
<223> OTHER INFORMATION: oligonucleotide

<400> SEQUENCE: 514
caugcagaac cucaaugacu gccuggccu                                          29

<210> SEQ ID NO 515
<211> LENGTH: 29
<212> TYPE: RNA
<213> ORGANISM: Artificial Sequence
<220> FEATURE:
<223> OTHER INFORMATION: oligonucleotide

<400> SEQUENCE: 515
augcagaacc ucaaugacug ccuggccuc                                          29

<210> SEQ ID NO 516
<211> LENGTH: 29
<212> TYPE: RNA
<213> ORGANISM: Artificial Sequence
<220> FEATURE:
<223> OTHER INFORMATION: oligonucleotide

<400> SEQUENCE: 516
ugcagaaccu caaugacugc cuggccucc                                          29

<210> SEQ ID NO 517
<211> LENGTH: 29
<212> TYPE: RNA
<213> ORGANISM: Artificial Sequence
<220> FEATURE:
<223> OTHER INFORMATION: oligonucleotide

<400> SEQUENCE: 517
gcagaaccuc aaugacugcc uggccuccu                                          29

<210> SEQ ID NO 518
<211> LENGTH: 29
<212> TYPE: RNA
<213> ORGANISM: Artificial Sequence
<220> FEATURE:
<223> OTHER INFORMATION: oligonucleotide

<400> SEQUENCE: 518
cagaaccuca augacugccu ggccuccua                                          29

<210> SEQ ID NO 519
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 519
agaaccucaa ugacugccug gccuccuac                                          29

<210> SEQ ID NO 520
<211> LENGTH: 29
<212> TYPE: RNA
<213> ORGANISM: Artificial Sequence
<220> FEATURE:
<223> OTHER INFORMATION: oligonucleotide

<400> SEQUENCE: 520
gaaccucaau gacugccugg ccuccuacc                                          29

<210> SEQ ID NO 521
<211> LENGTH: 29
<212> TYPE: RNA
<213> ORGANISM: Artificial Sequence
<220> FEATURE:
<223> OTHER INFORMATION: oligonucleotide

<400> SEQUENCE: 521
aaccucaaug acugccuggc cuccuaccu                                          29

<210> SEQ ID NO 522
<211> LENGTH: 29
<212> TYPE: RNA
<213> ORGANISM: Artificial Sequence
<220> FEATURE:
<223> OTHER INFORMATION: oligonucleotide

<400> SEQUENCE: 522
accucaauga cugccuggcc uccuaccug                                          29

<210> SEQ ID NO 523
<211> LENGTH: 29
<212> TYPE: RNA
<213> ORGANISM: Artificial Sequence
<220> FEATURE:
<223> OTHER INFORMATION: oligonucleotide

<400> SEQUENCE: 523
ccucaaugac ugccuggccu ccuaccugg                                          29

<210> SEQ ID NO 524
<211> LENGTH: 29
<212> TYPE: RNA
<213> ORGANISM: Artificial Sequence
<220> FEATURE:
<223> OTHER INFORMATION: oligonucleotide

<400> SEQUENCE: 524
cucaaugacu gccuggccuc cuaccugga                                          29

<210> SEQ ID NO 525
<211> LENGTH: 29
<212> TYPE: RNA
<213> ORGANISM: Artificial Sequence
<220> FEATURE:
<223> OTHER INFORMATION: oligonucleotide

<400> SEQUENCE: 525
ucaaugacug ccuggccucc uaccuggac                                          29
```

```
<210> SEQ ID NO 526
<211> LENGTH: 29
<212> TYPE: RNA
<213> ORGANISM: Artificial Sequence
<220> FEATURE:
<223> OTHER INFORMATION: oligonucleotide

<400> SEQUENCE: 526
caaugacugc cuggccuccu accuggaca                              29

<210> SEQ ID NO 527
<211> LENGTH: 29
<212> TYPE: RNA
<213> ORGANISM: Artificial Sequence
<220> FEATURE:
<223> OTHER INFORMATION: oligonucleotide

<400> SEQUENCE: 527
aaugacugcc uggccuccua ccuggacaa                              29

<210> SEQ ID NO 528
<211> LENGTH: 29
<212> TYPE: RNA
<213> ORGANISM: Artificial Sequence
<220> FEATURE:
<223> OTHER INFORMATION: oligonucleotide

<400> SEQUENCE: 528
augacugccu ggccuccuac cuggacaag                              29

<210> SEQ ID NO 529
<211> LENGTH: 29
<212> TYPE: RNA
<213> ORGANISM: Artificial Sequence
<220> FEATURE:
<223> OTHER INFORMATION: oligonucleotide

<400> SEQUENCE: 529
ugacugccug gccuccuacc uggacaagg                              29

<210> SEQ ID NO 530
<211> LENGTH: 29
<212> TYPE: RNA
<213> ORGANISM: Artificial Sequence
<220> FEATURE:
<223> OTHER INFORMATION: oligonucleotide

<400> SEQUENCE: 530
gacugccugg ccuccuaccu ggacaaggu                              29

<210> SEQ ID NO 531
<211> LENGTH: 29
<212> TYPE: RNA
<213> ORGANISM: Artificial Sequence
<220> FEATURE:
<223> OTHER INFORMATION: oligonucleotide

<400> SEQUENCE: 531
acugccuggc cuccuaccug gacaaggug                              29

<210> SEQ ID NO 532
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 532
cugccuggcc uccuaccugg acaaggugc                                  29

<210> SEQ ID NO 533
<211> LENGTH: 29
<212> TYPE: RNA
<213> ORGANISM: Artificial Sequence
<220> FEATURE:
<223> OTHER INFORMATION: oligonucleotide

<400> SEQUENCE: 533
ugccuggccu ccuaccugga caaggugcg                                  29

<210> SEQ ID NO 534
<211> LENGTH: 98
<212> TYPE: DNA
<213> ORGANISM: Homo sapiens

<400> SEQUENCE: 534
tgggcttctg gtgggcagtg agaaggtgac catgcagaac ctcaatgacc gcctggcctc    60
ctacctggac aaggtgcgtg ctctggagga ggccaacg                            98

<210> SEQ ID NO 535
<211> LENGTH: 98
<212> TYPE: DNA
<213> ORGANISM: Homo sapiens

<400> SEQUENCE: 535
tgggcttctg gtgggcagtg agaaggtgac catgcagaac ctcaatgacc gcctggcctc    60
ctacccggac aaggtgcgtg ctctggagga ggccaacg                            98

<210> SEQ ID NO 536
<211> LENGTH: 29
<212> TYPE: RNA
<213> ORGANISM: Artificial Sequence
<220> FEATURE:
<223> OTHER INFORMATION: oligonucleotide

<400> SEQUENCE: 536
aaccucaaug accgccuggc cuccuaccc                                  29

<210> SEQ ID NO 537
<211> LENGTH: 29
<212> TYPE: RNA
<213> ORGANISM: Artificial Sequence
<220> FEATURE:
<223> OTHER INFORMATION: oligonucleotide

<400> SEQUENCE: 537
accucaauga ccgccuggcc uccuacccg                                  29

<210> SEQ ID NO 538
<211> LENGTH: 29
<212> TYPE: RNA
<213> ORGANISM: Artificial Sequence
<220> FEATURE:
<223> OTHER INFORMATION: oligonucleotide

<400> SEQUENCE: 538
ccucaaugac cgccuggccu ccuacccgg                                  29
```

```
<210> SEQ ID NO 539
<211> LENGTH: 29
<212> TYPE: RNA
<213> ORGANISM: Artificial Sequence
<220> FEATURE:
<223> OTHER INFORMATION: oligonucleotide

<400> SEQUENCE: 539
cucaaugacc gccuggccuc cuacccgga                                             29

<210> SEQ ID NO 540
<211> LENGTH: 29
<212> TYPE: RNA
<213> ORGANISM: Artificial Sequence
<220> FEATURE:
<223> OTHER INFORMATION: oligonucleotide

<400> SEQUENCE: 540
ucaaugaccg ccuggccucc uacccggac                                             29

<210> SEQ ID NO 541
<211> LENGTH: 29
<212> TYPE: RNA
<213> ORGANISM: Artificial Sequence
<220> FEATURE:
<223> OTHER INFORMATION: oligonucleotide

<400> SEQUENCE: 541
caaugaccgc cuggccuccu acccggaca                                             29

<210> SEQ ID NO 542
<211> LENGTH: 29
<212> TYPE: RNA
<213> ORGANISM: Artificial Sequence
<220> FEATURE:
<223> OTHER INFORMATION: oligonucleotide

<400> SEQUENCE: 542
aaugaccgcc uggccuccua cccggacaa                                             29

<210> SEQ ID NO 543
<211> LENGTH: 29
<212> TYPE: RNA
<213> ORGANISM: Artificial Sequence
<220> FEATURE:
<223> OTHER INFORMATION: oligonucleotide

<400> SEQUENCE: 543
augaccgccu ggccuccuac ccggacaag                                             29

<210> SEQ ID NO 544
<211> LENGTH: 29
<212> TYPE: RNA
<213> ORGANISM: Artificial Sequence
<220> FEATURE:
<223> OTHER INFORMATION: oligonucleotide

<400> SEQUENCE: 544
ugaccgccug gccuccuacc cggacaagg                                             29

<210> SEQ ID NO 545
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 545
gaccgccugg ccuccuaccc ggacaaggu                                29

<210> SEQ ID NO 546
<211> LENGTH: 29
<212> TYPE: RNA
<213> ORGANISM: Artificial Sequence
<220> FEATURE:
<223> OTHER INFORMATION: oligonucleotide

<400> SEQUENCE: 546
accgccuggc cuccuacccg gacaaggug                                29

<210> SEQ ID NO 547
<211> LENGTH: 29
<212> TYPE: RNA
<213> ORGANISM: Artificial Sequence
<220> FEATURE:
<223> OTHER INFORMATION: oligonucleotide

<400> SEQUENCE: 547
ccgccuggcc uccuacccgg acaaggugc                                29

<210> SEQ ID NO 548
<211> LENGTH: 29
<212> TYPE: RNA
<213> ORGANISM: Artificial Sequence
<220> FEATURE:
<223> OTHER INFORMATION: oligonucleotide

<400> SEQUENCE: 548
cgccuggccu ccuacccgga caaggugcg                                29

<210> SEQ ID NO 549
<211> LENGTH: 29
<212> TYPE: RNA
<213> ORGANISM: Artificial Sequence
<220> FEATURE:
<223> OTHER INFORMATION: oligonucleotide

<400> SEQUENCE: 549
gccuggccuc cuacccggac aaggugcgu                                29

<210> SEQ ID NO 550
<211> LENGTH: 29
<212> TYPE: RNA
<213> ORGANISM: Artificial Sequence
<220> FEATURE:
<223> OTHER INFORMATION: oligonucleotide

<400> SEQUENCE: 550
ccuggccucc uacccggaca aggugcgug                                29

<210> SEQ ID NO 551
<211> LENGTH: 29
<212> TYPE: RNA
<213> ORGANISM: Artificial Sequence
<220> FEATURE:
<223> OTHER INFORMATION: oligonucleotide

<400> SEQUENCE: 551
cuggccuccu acccggacaa ggugcgugc                                29
```

```
<210> SEQ ID NO 552
<211> LENGTH: 29
<212> TYPE: RNA
<213> ORGANISM: Artificial Sequence
<220> FEATURE:
<223> OTHER INFORMATION: oligonucleotide

<400> SEQUENCE: 552
uggccuccua cccggacaag gugcgugcu                                    29

<210> SEQ ID NO 553
<211> LENGTH: 29
<212> TYPE: RNA
<213> ORGANISM: Artificial Sequence
<220> FEATURE:
<223> OTHER INFORMATION: oligonucleotide

<400> SEQUENCE: 553
ggccuccuac ccggacaagg ugcgugcuc                                    29

<210> SEQ ID NO 554
<211> LENGTH: 29
<212> TYPE: RNA
<213> ORGANISM: Artificial Sequence
<220> FEATURE:
<223> OTHER INFORMATION: oligonucleotide

<400> SEQUENCE: 554
gccuccuacc cggacaaggu gcgugcucu                                    29

<210> SEQ ID NO 555
<211> LENGTH: 29
<212> TYPE: RNA
<213> ORGANISM: Artificial Sequence
<220> FEATURE:
<223> OTHER INFORMATION: oligonucleotide

<400> SEQUENCE: 555
ccuccuaccc ggacaaggug cgugcucug                                    29

<210> SEQ ID NO 556
<211> LENGTH: 29
<212> TYPE: RNA
<213> ORGANISM: Artificial Sequence
<220> FEATURE:
<223> OTHER INFORMATION: oligonucleotide

<400> SEQUENCE: 556
cuccuacccg gacaaggugc gugcucugg                                    29

<210> SEQ ID NO 557
<211> LENGTH: 29
<212> TYPE: RNA
<213> ORGANISM: Artificial Sequence
<220> FEATURE:
<223> OTHER INFORMATION: oligonucleotide

<400> SEQUENCE: 557
uccuacccgg acaaggugcg ugcucugga                                    29

<210> SEQ ID NO 558
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 558
ccuacccgga caaggugcgu gcucuggag                                      29

<210> SEQ ID NO 559
<211> LENGTH: 29
<212> TYPE: RNA
<213> ORGANISM: Artificial Sequence
<220> FEATURE:
<223> OTHER INFORMATION: oligonucleotide

<400> SEQUENCE: 559
cuacccggac aaggugcgug cucuggagg                                      29

<210> SEQ ID NO 560
<211> LENGTH: 29
<212> TYPE: RNA
<213> ORGANISM: Artificial Sequence
<220> FEATURE:
<223> OTHER INFORMATION: oligonucleotide

<400> SEQUENCE: 560
cuacccggac aaggugcgug cucuggagg                                      29

<210> SEQ ID NO 561
<211> LENGTH: 29
<212> TYPE: RNA
<213> ORGANISM: Artificial Sequence
<220> FEATURE:
<223> OTHER INFORMATION: oligonucleotide

<400> SEQUENCE: 561
acccggacaa ggugcgugcu cuggaggag                                      29

<210> SEQ ID NO 562
<211> LENGTH: 29
<212> TYPE: RNA
<213> ORGANISM: Artificial Sequence
<220> FEATURE:
<223> OTHER INFORMATION: oligonucleotide

<400> SEQUENCE: 562
cccggacaag gugcgugcuc uggaggagg                                      29

<210> SEQ ID NO 563
<211> LENGTH: 29
<212> TYPE: RNA
<213> ORGANISM: Artificial Sequence
<220> FEATURE:
<223> OTHER INFORMATION: oligonucleotide

<400> SEQUENCE: 563
ccggacaagg ugcgugcucu ggaggaggc                                      29

<210> SEQ ID NO 564
<211> LENGTH: 29
<212> TYPE: RNA
<213> ORGANISM: Artificial Sequence
<220> FEATURE:
<223> OTHER INFORMATION: oligonucleotide

<400> SEQUENCE: 564
cggacaaggu gcgugcucug gaggaggcc                                      29
```

```
<210> SEQ ID NO 565
<211> LENGTH: 80
<212> TYPE: DNA
<213> ORGANISM: Homo sapiens

<400> SEQUENCE: 565
ggctgctggc tggaggtgag aaggccacca tgcagaacct caatgaccgc ctggcctcct      60
acctggacaa ggtgcgtgcc                                                  80

<210> SEQ ID NO 566
<211> LENGTH: 80
<212> TYPE: DNA
<213> ORGANISM: Homo sapiens

<400> SEQUENCE: 566
ggctgctggc tggaggtgag aaggccacca tgcagaacct cagtgaccgc ctggcctcct      60
acctggacaa ggtgcgtgcc                                                  80

<210> SEQ ID NO 567
<211> LENGTH: 29
<212> TYPE: RNA
<213> ORGANISM: Artificial Sequence
<220> FEATURE:
<223> OTHER INFORMATION: oligonucleotide

<400> SEQUENCE: 567
ggugagaagg ccaccaugca gaaccucag                                        29

<210> SEQ ID NO 568
<211> LENGTH: 29
<212> TYPE: RNA
<213> ORGANISM: Artificial Sequence
<220> FEATURE:
<223> OTHER INFORMATION: oligonucleotide

<400> SEQUENCE: 568
gugagaaggc caccaugcag aaccucagu                                        29

<210> SEQ ID NO 569
<211> LENGTH: 29
<212> TYPE: RNA
<213> ORGANISM: Artificial Sequence
<220> FEATURE:
<223> OTHER INFORMATION: oligonucleotide

<400> SEQUENCE: 569
ugagaaggcc accaugcaga accucagug                                        29

<210> SEQ ID NO 570
<211> LENGTH: 29
<212> TYPE: RNA
<213> ORGANISM: Artificial Sequence
<220> FEATURE:
<223> OTHER INFORMATION: oligonucleotide

<400> SEQUENCE: 570
ugagaaggcc accaugcaga accucagug                                        29

<210> SEQ ID NO 571
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 571
agaaggccac caugcagaac cucagugac                                    29

<210> SEQ ID NO 572
<211> LENGTH: 29
<212> TYPE: RNA
<213> ORGANISM: Artificial Sequence
<220> FEATURE:
<223> OTHER INFORMATION: oligonucleotide

<400> SEQUENCE: 572
gaaggccacc augcagaacc ucagugacc                                    29

<210> SEQ ID NO 573
<211> LENGTH: 29
<212> TYPE: RNA
<213> ORGANISM: Artificial Sequence
<220> FEATURE:
<223> OTHER INFORMATION: oligonucleotide

<400> SEQUENCE: 573
aaggccacca ugcagaaccu cagugaccg                                    29

<210> SEQ ID NO 574
<211> LENGTH: 29
<212> TYPE: RNA
<213> ORGANISM: Artificial Sequence
<220> FEATURE:
<223> OTHER INFORMATION: oligonucleotide

<400> SEQUENCE: 574
aggccaccau gcagaaccuc agugaccgc                                    29

<210> SEQ ID NO 575
<211> LENGTH: 29
<212> TYPE: RNA
<213> ORGANISM: Artificial Sequence
<220> FEATURE:
<223> OTHER INFORMATION: oligonucleotide

<400> SEQUENCE: 575
ggccaccaug cagaaccuca gugaccgcc                                    29

<210> SEQ ID NO 576
<211> LENGTH: 29
<212> TYPE: RNA
<213> ORGANISM: Artificial Sequence
<220> FEATURE:
<223> OTHER INFORMATION: oligonucleotide

<400> SEQUENCE: 576
gccaccaugc agaaccucag ugaccgccu                                    29

<210> SEQ ID NO 577
<211> LENGTH: 29
<212> TYPE: RNA
<213> ORGANISM: Artificial Sequence
<220> FEATURE:
<223> OTHER INFORMATION: oligonucleotide

<400> SEQUENCE: 577
ccaccaugca gaaccucagu gaccgccug                                    29
```

```
<210> SEQ ID NO 578
<211> LENGTH: 29
<212> TYPE: RNA
<213> ORGANISM: Artificial Sequence
<220> FEATURE:
<223> OTHER INFORMATION: oligonucleotide

<400> SEQUENCE: 578
caccaugcag aaccucagug accgccugg                                              29

<210> SEQ ID NO 579
<211> LENGTH: 29
<212> TYPE: RNA
<213> ORGANISM: Artificial Sequence
<220> FEATURE:
<223> OTHER INFORMATION: oligonucleotide

<400> SEQUENCE: 579
accaugcaga accucaguga ccgccuggc                                              29

<210> SEQ ID NO 580
<211> LENGTH: 29
<212> TYPE: RNA
<213> ORGANISM: Artificial Sequence
<220> FEATURE:
<223> OTHER INFORMATION: oligonucleotide

<400> SEQUENCE: 580
ccaugcagaa ccucagugac cgccuggcc                                              29

<210> SEQ ID NO 581
<211> LENGTH: 29
<212> TYPE: RNA
<213> ORGANISM: Artificial Sequence
<220> FEATURE:
<223> OTHER INFORMATION: oligonucleotide

<400> SEQUENCE: 581
caugcagaac cucagugacc gccuggccu                                              29

<210> SEQ ID NO 582
<211> LENGTH: 29
<212> TYPE: RNA
<213> ORGANISM: Artificial Sequence
<220> FEATURE:
<223> OTHER INFORMATION: oligonucleotide

<400> SEQUENCE: 582
augcagaacc ucagugaccg ccuggccuc                                              29

<210> SEQ ID NO 583
<211> LENGTH: 29
<212> TYPE: RNA
<213> ORGANISM: Artificial Sequence
<220> FEATURE:
<223> OTHER INFORMATION: oligonucleotide

<400> SEQUENCE: 583
ugcagaaccu cagugaccgc cuggccucc                                              29

<210> SEQ ID NO 584
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 584
gcagaaccuc agugaccgcc uggccuccu                                    29

<210> SEQ ID NO 585
<211> LENGTH: 29
<212> TYPE: RNA
<213> ORGANISM: Artificial Sequence
<220> FEATURE:
<223> OTHER INFORMATION: oligonucleotide

<400> SEQUENCE: 585
cagaaccuca gugaccgccu ggccuccua                                    29

<210> SEQ ID NO 586
<211> LENGTH: 29
<212> TYPE: RNA
<213> ORGANISM: Artificial Sequence
<220> FEATURE:
<223> OTHER INFORMATION: oligonucleotide

<400> SEQUENCE: 586
agaaccucag ugaccgccug gccuccuac                                    29

<210> SEQ ID NO 587
<211> LENGTH: 29
<212> TYPE: RNA
<213> ORGANISM: Artificial Sequence
<220> FEATURE:
<223> OTHER INFORMATION: oligonucleotide

<400> SEQUENCE: 587
gaaccucagu gaccgccugg ccuccuacc                                    29

<210> SEQ ID NO 588
<211> LENGTH: 29
<212> TYPE: RNA
<213> ORGANISM: Artificial Sequence
<220> FEATURE:
<223> OTHER INFORMATION: oligonucleotide

<400> SEQUENCE: 588
aaccucagug accgccuggc cuccuaccu                                    29

<210> SEQ ID NO 589
<211> LENGTH: 29
<212> TYPE: RNA
<213> ORGANISM: Artificial Sequence
<220> FEATURE:
<223> OTHER INFORMATION: oligonucleotide

<400> SEQUENCE: 589
accucaguga ccgccuggcc uccuaccug                                    29

<210> SEQ ID NO 590
<211> LENGTH: 29
<212> TYPE: RNA
<213> ORGANISM: Artificial Sequence
<220> FEATURE:
<223> OTHER INFORMATION: oligonucleotide

<400> SEQUENCE: 590
ccucagugac cgccuggccu ccuaccugg                                    29
```

```
<210> SEQ ID NO 591
<211> LENGTH: 29
<212> TYPE: RNA
<213> ORGANISM: Artificial Sequence
<220> FEATURE:
<223> OTHER INFORMATION: oligonucleotide

<400> SEQUENCE: 591
cucagugacc gccuggccuc cuaccugga                                      29

<210> SEQ ID NO 592
<211> LENGTH: 29
<212> TYPE: RNA
<213> ORGANISM: Artificial Sequence
<220> FEATURE:
<223> OTHER INFORMATION: oligonucleotide

<400> SEQUENCE: 592
ucagugaccg ccuggccucc uaccuggac                                      29

<210> SEQ ID NO 593
<211> LENGTH: 29
<212> TYPE: RNA
<213> ORGANISM: Artificial Sequence
<220> FEATURE:
<223> OTHER INFORMATION: oligonucleotide

<400> SEQUENCE: 593
cagugaccgc cuggccuccu accuggaca                                      29

<210> SEQ ID NO 594
<211> LENGTH: 29
<212> TYPE: RNA
<213> ORGANISM: Artificial Sequence
<220> FEATURE:
<223> OTHER INFORMATION: oligonucleotide

<400> SEQUENCE: 594
agugaccgcc uggccuccua ccuggacaa                                      29

<210> SEQ ID NO 595
<211> LENGTH: 29
<212> TYPE: RNA
<213> ORGANISM: Artificial Sequence
<220> FEATURE:
<223> OTHER INFORMATION: oligonucleotide

<400> SEQUENCE: 595
gugaccgccu ggccuccuac cuggacaag                                      29

<210> SEQ ID NO 596
<211> LENGTH: 80
<212> TYPE: DNA
<213> ORGANISM: Artificial Sequence
<220> FEATURE:
<223> OTHER INFORMATION: oligonucleotide

<400> SEQUENCE: 596
gctggagcag gagattgcca cctaccgccg cctgctggag ggagaggatg cccacctgac    60
tcagtacaag aaagaaccgg                                                80

<210> SEQ ID NO 597
<211> LENGTH: 80
<212> TYPE: DNA
<213> ORGANISM: Artificial Sequence
```

```
<220> FEATURE:
<223> OTHER INFORMATION: oligonucleotide

<400> SEQUENCE: 597
gctggagcag gagattgcca cctaccgccg cctgccggag ggagaggatg cccacctgac    60
tcagtacaag aaagaaccgg                                                80

<210> SEQ ID NO 598
<211> LENGTH: 29
<212> TYPE: RNA
<213> ORGANISM: Artificial Sequence
<220> FEATURE:
<223> OTHER INFORMATION: oligonucleotide

<400> SEQUENCE: 598
caggagauug ccaccuaccg ccgccugcc                                      29

<210> SEQ ID NO 599
<211> LENGTH: 29
<212> TYPE: RNA
<213> ORGANISM: Artificial Sequence
<220> FEATURE:
<223> OTHER INFORMATION: oligonucleotide

<400> SEQUENCE: 599
aggagauugc caccuaccgc cgccugccg                                      29

<210> SEQ ID NO 600
<211> LENGTH: 29
<212> TYPE: RNA
<213> ORGANISM: Artificial Sequence
<220> FEATURE:
<223> OTHER INFORMATION: oligonucleotide

<400> SEQUENCE: 600
ggagauugcc accuaccgcc gccugccgg                                      29

<210> SEQ ID NO 601
<211> LENGTH: 29
<212> TYPE: RNA
<213> ORGANISM: Artificial Sequence
<220> FEATURE:
<223> OTHER INFORMATION: oligonucleotide

<400> SEQUENCE: 601
gagauugcca ccuaccgccg ccugccgga                                      29

<210> SEQ ID NO 602
<211> LENGTH: 29
<212> TYPE: RNA
<213> ORGANISM: Artificial Sequence
<220> FEATURE:
<223> OTHER INFORMATION: oligonucleotide

<400> SEQUENCE: 602
agauugccac cuaccgccgc cugccggag                                      29

<210> SEQ ID NO 603
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 603
gauugccacc uaccgccgcc ugccggagg                              29

<210> SEQ ID NO 604
<211> LENGTH: 29
<212> TYPE: RNA
<213> ORGANISM: Artificial Sequence
<220> FEATURE:
<223> OTHER INFORMATION: oligonucleotide

<400> SEQUENCE: 604
auugccaccu accgccgccu gccggaggg                              29

<210> SEQ ID NO 605
<211> LENGTH: 29
<212> TYPE: RNA
<213> ORGANISM: Artificial Sequence
<220> FEATURE:
<223> OTHER INFORMATION: oligonucleotide

<400> SEQUENCE: 605
uugccaccua ccgccgccug ccggaggga                              29

<210> SEQ ID NO 606
<211> LENGTH: 29
<212> TYPE: RNA
<213> ORGANISM: Artificial Sequence
<220> FEATURE:
<223> OTHER INFORMATION: oligonucleotide

<400> SEQUENCE: 606
ugccaccuac cgccgccugc cggagggag                              29

<210> SEQ ID NO 607
<211> LENGTH: 29
<212> TYPE: RNA
<213> ORGANISM: Artificial Sequence
<220> FEATURE:
<223> OTHER INFORMATION: oligonucleotide

<400> SEQUENCE: 607
gccaccuacc gccgccugcc ggagggaga                              29

<210> SEQ ID NO 608
<211> LENGTH: 29
<212> TYPE: RNA
<213> ORGANISM: Artificial Sequence
<220> FEATURE:
<223> OTHER INFORMATION: oligonucleotide

<400> SEQUENCE: 608
ccaccuaccg ccgccugccg gagggagag                              29

<210> SEQ ID NO 609
<211> LENGTH: 29
<212> TYPE: RNA
<213> ORGANISM: Artificial Sequence
<220> FEATURE:
<223> OTHER INFORMATION: oligonucleotide

<400> SEQUENCE: 609
caccuaccgc cgccugccgg agggagagg                              29
```

```
<210> SEQ ID NO 610
<211> LENGTH: 29
<212> TYPE: RNA
<213> ORGANISM: Artificial Sequence
<220> FEATURE:
<223> OTHER INFORMATION: oligonucleotide

<400> SEQUENCE: 610
accuaccgcc gccugccgga gggagagga                                29

<210> SEQ ID NO 611
<211> LENGTH: 29
<212> TYPE: RNA
<213> ORGANISM: Artificial Sequence
<220> FEATURE:
<223> OTHER INFORMATION: oligonucleotide

<400> SEQUENCE: 611
ccuaccgccg ccugccggag ggagaggau                                29

<210> SEQ ID NO 612
<211> LENGTH: 29
<212> TYPE: RNA
<213> ORGANISM: Artificial Sequence
<220> FEATURE:
<223> OTHER INFORMATION: oligonucleotide

<400> SEQUENCE: 612
cuaccgccgc cugccggagg gagaggaug                                29

<210> SEQ ID NO 613
<211> LENGTH: 29
<212> TYPE: RNA
<213> ORGANISM: Artificial Sequence
<220> FEATURE:
<223> OTHER INFORMATION: oligonucleotide

<400> SEQUENCE: 613
uaccgccgcc ugccggaggg agaggaugc                                29

<210> SEQ ID NO 614
<211> LENGTH: 29
<212> TYPE: RNA
<213> ORGANISM: Artificial Sequence
<220> FEATURE:
<223> OTHER INFORMATION: oligonucleotide

<400> SEQUENCE: 614
accgccgccu gccggaggga gaggaugcc                                29

<210> SEQ ID NO 615
<211> LENGTH: 29
<212> TYPE: RNA
<213> ORGANISM: Artificial Sequence
<220> FEATURE:
<223> OTHER INFORMATION: oligonucleotide

<400> SEQUENCE: 615
ccgccgccug ccggagggag aggaugccc                                29

<210> SEQ ID NO 616
<211> LENGTH: 29
<212> TYPE: RNA
<213> ORGANISM: Artificial Sequence
<220> FEATURE:
<223> OTHER INFORMATION: oligonucleotide
```

```
<400> SEQUENCE: 616
cgccgccugc cggagggaga ggaugccca                              29

<210> SEQ ID NO 617
<211> LENGTH: 29
<212> TYPE: RNA
<213> ORGANISM: Artificial Sequence
<220> FEATURE:
<223> OTHER INFORMATION: oligonucleotide

<400> SEQUENCE: 617
gccgccugcc ggagggagag gaugcccac                              29

<210> SEQ ID NO 618
<211> LENGTH: 29
<212> TYPE: RNA
<213> ORGANISM: Artificial Sequence
<220> FEATURE:
<223> OTHER INFORMATION: oligonucleotide

<400> SEQUENCE: 618
ccgccugccg gagggagagg augcccacc                              29

<210> SEQ ID NO 619
<211> LENGTH: 29
<212> TYPE: RNA
<213> ORGANISM: Artificial Sequence
<220> FEATURE:
<223> OTHER INFORMATION: oligonucleotide

<400> SEQUENCE: 619
cgccugccgg agggaggga ugcccaccu                               29

<210> SEQ ID NO 620
<211> LENGTH: 29
<212> TYPE: RNA
<213> ORGANISM: Artificial Sequence
<220> FEATURE:
<223> OTHER INFORMATION: oligonucleotide

<400> SEQUENCE: 620
gccugccgga gggagaggau gcccaccug                              29

<210> SEQ ID NO 621
<211> LENGTH: 29
<212> TYPE: RNA
<213> ORGANISM: Artificial Sequence
<220> FEATURE:
<223> OTHER INFORMATION: oligonucleotide

<400> SEQUENCE: 621
ccugccggag ggagaggaug cccaccuga                              29

<210> SEQ ID NO 622
<211> LENGTH: 29
<212> TYPE: RNA
<213> ORGANISM: Artificial Sequence
<220> FEATURE:
<223> OTHER INFORMATION: oligonucleotide

<400> SEQUENCE: 622
cugccggagg gagaggaugc ccaccugac                              29
```

```
<210> SEQ ID NO 623
<211> LENGTH: 29
<212> TYPE: RNA
<213> ORGANISM: Artificial Sequence
<220> FEATURE:
<223> OTHER INFORMATION: oligonucleotide

<400> SEQUENCE: 623
ugccggaggg agaggaugcc caccugacu                                   29

<210> SEQ ID NO 624
<211> LENGTH: 29
<212> TYPE: RNA
<213> ORGANISM: Artificial Sequence
<220> FEATURE:
<223> OTHER INFORMATION: oligonucleotide

<400> SEQUENCE: 624
gccggaggga gaggaugccc accugacuc                                   29

<210> SEQ ID NO 625
<211> LENGTH: 29
<212> TYPE: RNA
<213> ORGANISM: Artificial Sequence
<220> FEATURE:
<223> OTHER INFORMATION: oligonucleotide

<400> SEQUENCE: 625
ccggagggag aggaugccca ccugacuca                                   29

<210> SEQ ID NO 626
<211> LENGTH: 29
<212> TYPE: RNA
<213> ORGANISM: Artificial Sequence
<220> FEATURE:
<223> OTHER INFORMATION: oligonucleotide

<400> SEQUENCE: 626
cggagggaga ggaugcccac cugacucag                                   29

<210> SEQ ID NO 627
<211> LENGTH: 40
<212> TYPE: DNA
<213> ORGANISM: Homo sapiens

<400> SEQUENCE: 627
tgaacagatc aagaccctca acaacaagtt tgcctccttc                       40

<210> SEQ ID NO 628
<211> LENGTH: 40
<212> TYPE: DNA
<213> ORGANISM: Homo sapiens

<400> SEQUENCE: 628
tgaacagatc aagaccctca aaacaagtt tgcctccttc                        40

<210> SEQ ID NO 629
<211> LENGTH: 21
<212> TYPE: RNA
<213> ORGANISM: Artificial sequence
<220> FEATURE:
<223> OTHER INFORMATION: oligonucleotide

<400> SEQUENCE: 629
acagaucaag acccucaaau u                                           21
```

```
<210> SEQ ID NO 630
<211> LENGTH: 21
<212> TYPE: RNA
<213> ORGANISM: Artificial sequence
<220> FEATURE:
<223> OTHER INFORMATION: oligonuceotide

<400> SEQUENCE: 630
cagaucaaga cccucaaaau u                                              21

<210> SEQ ID NO 631
<211> LENGTH: 21
<212> TYPE: RNA
<213> ORGANISM: Artificial sequence
<220> FEATURE:
<223> OTHER INFORMATION: oligonuceotide

<400> SEQUENCE: 631
agaucaagac ccucaaaaau u                                              21

<210> SEQ ID NO 632
<211> LENGTH: 21
<212> TYPE: RNA
<213> ORGANISM: Artificial sequence
<220> FEATURE:
<223> OTHER INFORMATION: oligonucleotide

<400> SEQUENCE: 632
gaucaagacc cucaaaaacu u                                              21

<210> SEQ ID NO 633
<211> LENGTH: 21
<212> TYPE: RNA
<213> ORGANISM: Artificial sequence
<220> FEATURE:
<223> OTHER INFORMATION: oligonuceotide

<400> SEQUENCE: 633
aucaagaccc ucaaaaacau u                                              21

<210> SEQ ID NO 634
<211> LENGTH: 21
<212> TYPE: RNA
<213> ORGANISM: Artificial sequence
<220> FEATURE:
<223> OTHER INFORMATION: oligonucleotide

<400> SEQUENCE: 634
ucaagacccu caaaaacaau u                                              21

<210> SEQ ID NO 635
<211> LENGTH: 21
<212> TYPE: RNA
<213> ORGANISM: Artificial sequence
<220> FEATURE:
<223> OTHER INFORMATION: oligonucleotide

<400> SEQUENCE: 635
caagacccuc aaaaacaagu u                                              21

<210> SEQ ID NO 636
<211> LENGTH: 21
<212> TYPE: RNA
<213> ORGANISM: Artificial sequence
<220> FEATURE:
<223> OTHER INFORMATION: oligonucleotide
```

-continued

<400> SEQUENCE: 636
aagacccuca aaacaaguu u                                                    21

<210> SEQ ID NO 637
<211> LENGTH: 21
<212> TYPE: RNA
<213> ORGANISM: Artificial sequence
<220> FEATURE:
<223> OTHER INFORMATION: oligonucleotide

<400> SEQUENCE: 637
agacccucaa aacaaguuu u                                                    21

<210> SEQ ID NO 638
<211> LENGTH: 21
<212> TYPE: RNA
<213> ORGANISM: Artificial sequence
<220> FEATURE:
<223> OTHER INFORMATION: oligonucleotide

<400> SEQUENCE: 638
gacccucaaa aacaaguuuu u                                                   21

<210> SEQ ID NO 639
<211> LENGTH: 21
<212> TYPE: RNA
<213> ORGANISM: Artificial sequence
<220> FEATURE:
<223> OTHER INFORMATION: oligonucleotide

<400> SEQUENCE: 639
acccucaaaa acaaguuugu u                                                   21

<210> SEQ ID NO 640
<211> LENGTH: 21
<212> TYPE: RNA
<213> ORGANISM: Artificial sequence
<220> FEATURE:
<223> OTHER INFORMATION: oligonucleotide

<400> SEQUENCE: 640
cccucaaaaa caaguuugcu u                                                   21

<210> SEQ ID NO 641
<211> LENGTH: 21
<212> TYPE: RNA
<213> ORGANISM: Artificial sequence
<220> FEATURE:
<223> OTHER INFORMATION: oligonucleotide

<400> SEQUENCE: 641
ccucaaaaac aaguuugccu u                                                   21

<210> SEQ ID NO 642
<211> LENGTH: 21
<212> TYPE: RNA
<213> ORGANISM: Artificial sequence
<220> FEATURE:
<223> OTHER INFORMATION: oligonucleotide

<400> SEQUENCE: 642
cucaaaaaca aguuugccuu u                                                   21

```
<210> SEQ ID NO 643
<211> LENGTH: 21
<212> TYPE: RNA
<213> ORGANISM: Artificial sequence
<220> FEATURE:
<223> OTHER INFORMATION: oligonuceotide

<400> SEQUENCE: 643
ucaaaaacaa guuugccucu u                                              21

<210> SEQ ID NO 644
<211> LENGTH: 21
<212> TYPE: RNA
<213> ORGANISM: Artificial sequence
<220> FEATURE:
<223> OTHER INFORMATION: oligonuceotide

<400> SEQUENCE: 644
caaaaacaag uuugccuccu u                                              21

<210> SEQ ID NO 645
<211> LENGTH: 21
<212> TYPE: RNA
<213> ORGANISM: Artificial sequence
<220> FEATURE:
<223> OTHER INFORMATION: oligonuceotide

<400> SEQUENCE: 645
aaaaacaagu ugccuccuu u                                               21

<210> SEQ ID NO 646
<211> LENGTH: 21
<212> TYPE: RNA
<213> ORGANISM: Artificial sequence
<220> FEATURE:
<223> OTHER INFORMATION: oligonuceotide

<400> SEQUENCE: 646
aaaacaaguu ugccuccuuu u                                              21

<210> SEQ ID NO 647
<211> LENGTH: 21
<212> TYPE: RNA
<213> ORGANISM: Artificial sequence
<220> FEATURE:
<223> OTHER INFORMATION: oligonuceotide

<400> SEQUENCE: 647
aaacaaguuu gccuccuucu u                                              21

<210> SEQ ID NO 648
<211> LENGTH: 21
<212> TYPE: DNA
<213> ORGANISM: Artificial sequence
<220> FEATURE:
<223> OTHER INFORMATION: oligonuceotide

<400> SEQUENCE: 648
gaccctcaaa aacaagtttt t                                              21

<210> SEQ ID NO 649
<211> LENGTH: 21
<212> TYPE: DNA
<213> ORGANISM: Artificial sequence
<220> FEATURE:
<223> OTHER INFORMATION: oligonuceotide
```

-continued

<400> SEQUENCE: 649
cctgcaagac cctcaaaaat t					21

<210> SEQ ID NO 650
<211> LENGTH: 21
<212> TYPE: DNA
<213> ORGANISM: Artificial sequence
<220> FEATURE:
<223> OTHER INFORMATION: oligonuceotide

<400> SEQUENCE: 650
agaucaagac ccucaaaaau t					21

<210> SEQ ID NO 651
<211> LENGTH: 21
<212> TYPE: DNA
<213> ORGANISM: Artificial sequence
<220> FEATURE:
<223> OTHER INFORMATION: oligonuceotide

<400> SEQUENCE: 651
cagatcaaga ccctcaaaat t					21

<210> SEQ ID NO 652
<211> LENGTH: 21
<212> TYPE: DNA
<213> ORGANISM: Artificial sequence
<220> FEATURE:
<223> OTHER INFORMATION: oligonuceotide

<400> SEQUENCE: 652
acagatcaag accctcaaat t					21

<210> SEQ ID NO 653
<211> LENGTH: 21
<212> TYPE: DNA
<213> ORGANISM: Artificial sequence
<220> FEATURE:
<223> OTHER INFORMATION: oligonuceotide

<400> SEQUENCE: 653
aaaacaagtt tgcctccttt t					21

<210> SEQ ID NO 654
<211> LENGTH: 21
<212> TYPE: RNA
<213> ORGANISM: Artificial sequence
<220> FEATURE:
<223> OTHER INFORMATION: oligonuceotide

<400> SEQUENCE: 654
ucaagacccu caacaacaau u					21

<210> SEQ ID NO 655
<211> LENGTH: 21
<212> TYPE: RNA
<213> ORGANISM: Artificial sequence
<220> FEATURE:
<223> OTHER INFORMATION: oligonuceotide

<400> SEQUENCE: 655
caacaaguuu gccuccuucu u					21

<210> SEQ ID NO 656
<211> LENGTH: 21
<212> TYPE: RNA
<213> ORGANISM: Artificial sequence
<220> FEATURE:
<223> OTHER INFORMATION: oligonuceotide

<400> SEQUENCE: 656
gaucaagacc cucaacaacu u                                             21

<210> SEQ ID NO 657
<211> LENGTH: 21
<212> TYPE: RNA
<213> ORGANISM: Artificial sequence
<220> FEATURE:
<223> OTHER INFORMATION: oligonucleotide

<400> SEQUENCE: 657
acaacaaguu ugccuccuuu u                                             21

<210> SEQ ID NO 658
<211> LENGTH: 21
<212> TYPE: RNA
<213> ORGANISM: Artificial sequence
<220> FEATURE:
<223> OTHER INFORMATION: oligonuceotide

<400> SEQUENCE: 658
gacccucaac aacaaguuuu u                                             21

<210> SEQ ID NO 659
<211> LENGTH: 40
<212> TYPE: DNA
<213> ORGANISM: Homo sapiens

<400> SEQUENCE: 659
tgaacagatc aagaccctca acaacaagtt tgcctccttc                         40

<210> SEQ ID NO 660
<211> LENGTH: 37
<212> TYPE: DNA
<213> ORGANISM: Homo sapiens

<400> SEQUENCE: 660
tgaacagatc aagaccctca acaagtttgc ctccttc                            37

<210> SEQ ID NO 661
<211> LENGTH: 21
<212> TYPE: DNA
<213> ORGANISM: Artificial sequence
<220> FEATURE:
<223> OTHER INFORMATION: oligonuceotide

<400> SEQUENCE: 661
tcaagaccct caacaagttt t                                             21

<210> SEQ ID NO 662
<211> LENGTH: 21
<212> TYPE: DNA
<213> ORGANISM: Artificial sequence
<220> FEATURE:
<223> OTHER INFORMATION: oligonuceotide

<400> SEQUENCE: 662
caagaccctc aacaagtttt t                                             21

```
<210> SEQ ID NO 663
<211> LENGTH: 21
<212> TYPE: DNA
<213> ORGANISM: Artificial sequence
<220> FEATURE:
<223> OTHER INFORMATION: oligonucleotide

<400> SEQUENCE: 663
aagaccctca acaagtttgt t                                               21

<210> SEQ ID NO 664
<211> LENGTH: 59
<212> TYPE: DNA
<213> ORGANISM: Homo sapiens

<400> SEQUENCE: 664
taaagtgcgt ctgctagctc tcggtcccac agtcctcagg cccctctctg gctgcagag     59

<210> SEQ ID NO 665
<211> LENGTH: 59
<212> TYPE: DNA
<213> ORGANISM: Homo sapiens

<400> SEQUENCE: 665
tgaagtgctg ccgccagctc tcagtcccac agctctcagg cccctctctg gcagcagag     59

<210> SEQ ID NO 666
<211> LENGTH: 59
<212> TYPE: DNA
<213> ORGANISM: Homo sapiens

<400> SEQUENCE: 666
ccctctcctc aggttgcctg tcctctcctg gcctccagtc tccctgctg tcccaggta      59

<210> SEQ ID NO 667
<211> LENGTH: 59
<212> TYPE: DNA
<213> ORGANISM: Homo sapiens

<400> SEQUENCE: 667
ccctctcctc aggttgcttg tcctcccctg gcctccagtc tccctgccc tccgggta       59

<210> SEQ ID NO 668
<211> LENGTH: 54
<212> TYPE: DNA
<213> ORGANISM: Homo sapiens

<400> SEQUENCE: 668
gagctgggga tgaatgctta gtgccttcac ttcttctctc tctctctata ccat          54

<210> SEQ ID NO 669
<211> LENGTH: 44
<212> TYPE: DNA
<213> ORGANISM: Homo sapiens

<400> SEQUENCE: 669
gagctgggat gccctcactt ttcttctcat caatacctgt tcca                     44

<210> SEQ ID NO 670
<211> LENGTH: 59
<212> TYPE: DNA
<213> ORGANISM: Homo sapiens
```

<400> SEQUENCE: 670
ctgagcaccc attgctcacc atcagatcaa cctctgattt tacatcatga tgtaatcac    59

<210> SEQ ID NO 671
<211> LENGTH: 47
<212> TYPE: DNA
<213> ORGANISM: Homo sapiens

<400> SEQUENCE: 671
ctgagctcct gttgcttacc atcaagtcaa cagttatcag cactcag    47

<210> SEQ ID NO 672
<211> LENGTH: 54
<212> TYPE: DNA
<213> ORGANISM: Homo sapiens

<400> SEQUENCE: 672
cactggagct tcactttgtt actaaattat taatttcttg cctccagtgt tcta    54

<210> SEQ ID NO 673
<211> LENGTH: 41
<212> TYPE: DNA
<213> ORGANISM: Homo sapiens

<400> SEQUENCE: 673
acatgcgaat gtcctttta gttcccgtat tattacaggt a    41

<210> SEQ ID NO 674
<211> LENGTH: 51
<212> TYPE: DNA
<213> ORGANISM: Homo sapiens

<400> SEQUENCE: 674
tctctgaggc tgagcattat aagaaaatga cctctgctcc ttttcattgc a    51

<210> SEQ ID NO 675
<211> LENGTH: 52
<212> TYPE: DNA
<213> ORGANISM: Homo sapiens

<400> SEQUENCE: 675
tctgagtctg ccataattct gagaagaaaa tgacctatat ccccataaga ac    52

<210> SEQ ID NO 676
<211> LENGTH: 46
<212> TYPE: DNA
<213> ORGANISM: Homo sapiens

<400> SEQUENCE: 676
gaaaattgcc agggcttat ttcagaacaa cttccactta ctttcc    46

<210> SEQ ID NO 677
<211> LENGTH: 56
<212> TYPE: DNA
<213> ORGANISM: Homo sapiens

<400> SEQUENCE: 677
tgaaactcag tctaggtcca gctgcagatg aggagtcctc tctttaattg ctaacc    56

<210> SEQ ID NO 678
<211> LENGTH: 38
<212> TYPE: DNA
<213> ORGANISM: Homo sapiens

```
<400> SEQUENCE: 678
actggctctc aaactctcta acttataagt gttgtgaa                              38

<210> SEQ ID NO 679
<211> LENGTH: 58
<212> TYPE: DNA
<213> ORGANISM: Homo sapiens

<400> SEQUENCE: 679
atcctgccca ttatagctac actcaggagt tctcatctga caagtcagtt gtcctgat       58

<210> SEQ ID NO 680
<211> LENGTH: 57
<212> TYPE: DNA
<213> ORGANISM: Homo sapiens

<400> SEQUENCE: 680
cccccaccca ggcagtatcc atgaaagcac aagtgactag tcctatgatg tacaaag        57

<210> SEQ ID NO 681
<211> LENGTH: 49
<212> TYPE: DNA
<213> ORGANISM: Homo sapiens

<400> SEQUENCE: 681
cttctcttgc agtgtccctg aatggcaagt gatgtacctt ctgatgcag                 49

<210> SEQ ID NO 682
<211> LENGTH: 53
<212> TYPE: DNA
<213> ORGANISM: Homo sapiens

<400> SEQUENCE: 682
cctgtatctc tgtgatgatt tctgtgctct tcgctctttg caattgctaa ata            53

<210> SEQ ID NO 683
<211> LENGTH: 57
<212> TYPE: DNA
<213> ORGANISM: Homo sapiens

<400> SEQUENCE: 683
tctgcattcc tgcactgctt tctctgctct ctttgccttc ttttgttctg ttgaata        57

<210> SEQ ID NO 684
<211> LENGTH: 33
<212> TYPE: DNA
<213> ORGANISM: Homo sapiens

<400> SEQUENCE: 684
aagcagattt ataatacaat aaaaaaaaaa aaa                                  33

<210> SEQ ID NO 685
<211> LENGTH: 31
<212> TYPE: DNA
<213> ORGANISM: Homo sapiens

<400> SEQUENCE: 685
aagcatattg agaatgtgaa aaaaaaaaa a                                     31
```